US00RE46757E

(19) United States
(12) Reissued Patent
Baettig et al.

(10) Patent Number: US RE46,757 E
(45) Date of Reissued Patent: *Mar. 20, 2018

(54) PYRIDINE AND PYRAZINE DERIVATIVE FOR THE TREATMENT OF CF

(71) Applicant: Novartis AG, Basel (CH)

(72) Inventors: Urs Baettig, Horsham (GB); Kamlesh Jagdis Bala, Horsham (GB); Emma Budd, Horsham (GB); Lee Edwards, Horsham (GB); Catherine Howsham, Horsham (GB); Glyn Alan Hughes, Horsham (GB); Darren Mark Legrand, East Grinstead (GB); Katrin Spiegel, Horsham (GB)

(73) Assignee: Novartis AG, Basel (CH)

( * ) Notice: This patent is subject to a terminal disclaimer.

(21) Appl. No.: 14/755,691

(22) Filed: Jun. 30, 2015

Related U.S. Patent Documents

Reissue of:
(64) Patent No.: 8,476,269
Issued: Jul. 2, 2013
Appl. No.: 13/544,182
Filed: Jul. 9, 2012

U.S. Applications:
(63) Continuation of application No. 13/047,319, filed on Mar. 14, 2011, now Pat. No. 8,247,436.

(60) Provisional application No. 61/315,509, filed on Mar. 19, 2010, provisional application No. 61/441,853, filed on Feb. 11, 2011.

(51) Int. Cl.

| | |
|---|---|
| ***A61K 31/5355*** | (2006.01) |
| ***C07D 213/26*** | (2006.01) |
| ***A61K 31/4965*** | (2006.01) |
| ***A61K 31/4453*** | (2006.01) |
| ***C07D 241/16*** | (2006.01) |
| ***C07D 213/04*** | (2006.01) |
| ***C07D 213/61*** | (2006.01) |
| ***C07D 413/12*** | (2006.01) |
| ***C07D 211/06*** | (2006.01) |
| ***A61K 31/497*** | (2006.01) |
| ***C07D 213/22*** | (2006.01) |
| ***A61K 31/445*** | (2006.01) |
| ***A61K 31/444*** | (2006.01) |
| ***A61K 31/443*** | (2006.01) |
| ***A61K 31/454*** | (2006.01) |
| ***A61K 31/44*** | (2006.01) |
| ***A61K 31/4439*** | (2006.01) |
| ***A61K 31/4418*** | (2006.01) |
| ***A61K 31/4545*** | (2006.01) |
| ***A61K 31/4412*** | (2006.01) |
| ***A61K 31/5377*** | (2006.01) |

(Continued)

(52) U.S. Cl.
CPC ..... *A61K 31/44* (2013.01); *A61K 31/443* (2013.01); *A61K 31/444* (2013.01); *A61K 31/4412* (2013.01); *A61K 31/4418* (2013.01); *A61K 31/4439* (2013.01); *A61K 31/4545* (2013.01); *A61K 31/497* (2013.01); *A61K 31/4965* (2013.01); *A61K 31/5377* (2013.01); *A61K 45/06* (2013.01); *C07D 213/38* (2013.01); *C07D 213/81* (2013.01); *C07D 241/26* (2013.01); *C07D 241/28* (2013.01); *C07D 401/04* (2013.01); *C07D 401/12* (2013.01); *C07D 403/12* (2013.01); *C07D 405/04* (2013.01); *C07D 405/12* (2013.01); *C07D 413/04* (2013.01); *C07D 413/12* (2013.01)

(58) Field of Classification Search
CPC .. C07D 213/38; C07D 213/81; C07D 241/28; C07D 401/04; C07D 401/12; C07D 403/12; C07D 405/04; C07D 405/12; C07D 413/04; C07D 413/12; C07D 241/26; A61K 31/4418; A61K 31/4412; A61K 31/443; A61K 31/44; A61K 31/4545; A61K 31/5377; A61K 31/497; A61K 31/4965; A61K 31/444; A61K 31/4439; A61K 45/06
USPC ..... 514/235.8, 237.2, 255.05, 255.06, 318, 514/334, 336, 338, 341, 343, 346, 352; 544/120, 131, 405, 407; 546/193, 258, 546/271.4, 271.7, 276.4, 283.4, 309
See application file for complete search history.

(56) References Cited

U.S. PATENT DOCUMENTS

| | | | |
|---|---|---|---|
| 3,313,813 | A | 4/1967 | Cragoe |
| 3,527,758 | A | 9/1970 | Cragoe et al. |

(Continued)

FOREIGN PATENT DOCUMENTS

| | | |
|---|---|---|
| DE | 3 18 94 | 4/1965 |
| EP | 0 393 861 A1 | 10/1990 |

(Continued)

OTHER PUBLICATIONS

[No Author Listed] COPD: Causes and Prevention. NIH SeniorHealth. National Heart, Lung, and Blood Institute. 6 pages. Website. Accessed Apr. 6, 2009. <http://nihseniorhealth.gov/copd/causesandprevention/01.html>.

(Continued)

*Primary Examiner* — Dwayne Jones
(74) *Attorney, Agent, or Firm* — Laura K. Madden

(57) ABSTRACT

The present invention provides pyridine and pyrazine derivatives which restore or enhance the function of mutant and/or wild type CFTR to treat cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced). Pharmaceutical compositions comprising such derivatives are also encompassed.

21 Claims, No Drawings

(51) Int. Cl.

| | |
|---|---|
| ***A61K 45/06*** | (2006.01) |
| ***C07D 213/81*** | (2006.01) |
| ***C07D 241/28*** | (2006.01) |
| ***C07D 241/26*** | (2006.01) |
| ***C07D 213/38*** | (2006.01) |
| ***C07D 401/12*** | (2006.01) |
| ***C07D 401/04*** | (2006.01) |
| ***C07D 403/12*** | (2006.01) |
| ***C07D 405/04*** | (2006.01) |
| ***C07D 405/12*** | (2006.01) |
| ***C07D 413/04*** | (2006.01) |

(56) References Cited

U.S. PATENT DOCUMENTS 3,714,357 A 1/1973 Thevenot et al.
5,059,605 A 10/1991 Clough et al.
5,171,744 A 12/1992 Cross et al.
5,602,157 A 2/1997 Christensen, IV
5,605,923 A 2/1997 Christensen, IV et al.
5,658,933 A 8/1997 Weidmann et al.
6,136,821 A 10/2000 Hersperger
6,140,362 A 10/2000 Michelotti et al.
6,166,037 A 12/2000 Budhu et al.
6,288,055 B1 9/2001 Natarajan et al.
6,333,354 B1 12/2001 Schudt
6,391,865 B1 5/2002 Baroudy et al.
6,455,603 B1 9/2002 Fogg et al.
6,500,405 B1 12/2002 Young et al.
6,518,290 B1 2/2003 Sierra et al.
6,747,043 B2 6/2004 Moran et al.
6,750,226 B2 6/2004 Fernandez et al.
6,777,409 B2 8/2004 Jaroch et al.
6,844,362 B2 1/2005 Brown et al.
6,858,627 B2 2/2005 Bekkali et al.
6,914,160 B1 7/2005 Armour et al.
6,921,757 B2 7/2005 Cuenoud et al.
6,949,568 B2 9/2005 Moran et al.
6,951,888 B2 10/2005 Buettner et al.
7,045,658 B2 5/2006 Biggadike et al.
7,056,354 B2 6/2006 Fessmann et al.
7,056,916 B2 6/2006 Konetzki et al.
7,074,806 B2 7/2006 Kirrane, Jr. et al.
7,101,866 B2 9/2006 Biggadike et al.
7,109,202 B2 9/2006 Press et al.
7,112,595 B2 9/2006 Wagenen et al.
7,115,629 B2 10/2006 Farrerons et al.
7,125,892 B2 10/2006 Moran et al.
7,129,241 B2 10/2006 Eggenweiler et al.
7,135,471 B2 11/2006 Eggenweiler et al.
7,135,500 B2 11/2006 Konetzki et al.
7,135,600 B2 11/2006 Biggadike et al.
7,138,406 B2 11/2006 Chantigny et al.
7,144,908 B2 12/2006 Coe et al.
7,153,968 B2 12/2006 Dube et al.
7,166,637 B2 1/2007 Hofgen et al.
7,179,807 B2 2/2007 Yoon et al.
7,183,294 B2 2/2007 Brown et al.
7,186,735 B2 3/2007 Strobel et al.
7,186,864 B2 3/2007 Kirrane, Jr. et al.
7,192,978 B2 3/2007 Quinones
7,238,725 B2 7/2007 Balasubramanian et al.
7,268,152 B2 9/2007 Bekkali et al.
7,271,197 B2 9/2007 Box et al.
7,273,875 B2 9/2007 Denholm et al.
7,288,562 B2 10/2007 Mehta et al.
7,291,602 B2 11/2007 Tang et al.
7,291,608 B2 11/2007 Biggadike et al.
7,300,775 B2 11/2007 Madden et al.
7,329,676 B2 2/2008 Kautz et al.
7,361,668 B2 4/2008 Guyaux et al.
7,375,100 B2 5/2008 Brown et al.
7,402,598 B2 7/2008 Biggadike et al.
7,405,206 B2 7/2008 Biggadike et al.
7,423,046 B2 9/2008 Kautz et al.
7,442,839 B2 10/2008 Chapman et al.
7,452,904 B2 11/2008 Catena Ruiz et al.
7,553,966 B2 6/2009 Betageri et al.
7,625,937 B2 12/2009 Ali et al.
7,674,815 B2 3/2010 Faeh et al.
7,678,818 B2 3/2010 Conte et al.
7,704,995 B2 4/2010 Buhr et al.
7,709,478 B2 5/2010 Strobel et al.
7,732,432 B2 6/2010 Ali et al.
7,776,879 B2 8/2010 Buil Albero et al.
7,790,723 B2 9/2010 Eggenweiler et al.
7,893,087 B2 2/2011 Prat Quinones et al.
7,919,487 B2 4/2011 Sun et al.
7,928,105 B2 4/2011 Gangloff et al.
8,110,562 B2 2/2012 Dalton et al.
8,198,483 B2 6/2012 Box et al.
8,227,615 B2 7/2012 Hadida-Ruah et al.
8,247,436 B2 8/2012 Baettig et al.
8,263,590 B2 9/2012 Garcia-Echeverria et al.
8,268,834 B2 9/2012 Bruce et al.
8,278,337 B2 10/2012 Belanger et al.
8,283,356 B2 10/2012 Baenteli et al.
8,293,747 B2 10/2012 Reddy et al.
8,299,099 B2 10/2012 Ruah et al.
8,367,660 B2 2/2013 Binch et al.
8,372,885 B2 2/2013 Dobler et al.
8,377,923 B2 2/2013 Yoshimura et al.
8,415,358 B2 4/2013 Eriksen et al.
8,461,161 B2 6/2013 Burns et al.
8,476,269 B2 7/2013 Baettig et al.
8,481,734 B2 7/2013 Dorshow et al.
8,486,950 B2 7/2013 Goodacre et al.
8,513,242 B2 8/2013 Chiang et al.
8,518,952 B2 8/2013 Braganza et al.
8,541,421 B2 9/2013 Tachdjian et al.
8,552,006 B2 10/2013 Binch et al.
8,598,209 B2 12/2013 Burgey et al.
8,642,623 B2 2/2014 Frank et al.
8,664,228 B2 3/2014 Collingwood et al.
8,741,933 B2 6/2014 Hadida Ruah et al.
8,796,307 B2 8/2014 Cuenoud et al.
9,365,552 B2 * 6/2016 Baettig ..... C07D 213/81
2002/0022625 A1 2/2002 Walland
2002/0055651 A1 5/2002 Morgan et al.
2004/0097574 A1 5/2004 Marshall
2004/0110808 A1 6/2004 Strobel
2004/0167167 A1 8/2004 Mammen et al.
2004/0186113 A1 9/2004 Berg et al.
2004/0248867 A1 12/2004 Biggadike et al.
2005/0165028 A1 7/2005 Norman et al.
2005/0245588 A1 11/2005 Ali et al.
2005/0267114 A1 12/2005 Takaoka et al.
2006/0004056 A1 1/2006 Cote et al.
2006/0094879 A1 5/2006 Fonquerna et al.
2006/0113968 A1 6/2006 Flockerzi
2006/0116518 A1 6/2006 Flockerzi et al.
2006/0166995 A1 7/2006 Sterk
2006/0167001 A1 7/2006 Sterk
2006/0167048 A1 7/2006 Cumming et al.
2006/0205790 A1 9/2006 Coe et al.
2006/0241288 A1 10/2006 Roche et al.
2006/0252741 A1 11/2006 Colandrea et al.
2006/0276477 A1 12/2006 Klaus et al.
2007/0149547 A1 6/2007 Bonnefous et al.
2007/0249586 A1 10/2007 Cuenoud et al.
2007/0249630 A1 10/2007 Blake et al.
2008/0021024 A1 1/2008 Sucholeiki et al.
2008/0027044 A1 1/2008 Lewis et al.
2008/0108600 A1 5/2008 Wang et al.
2009/0017006 A1 1/2009 Freissmuth et al.
2010/0249071 A1 9/2010 Bannen et al.
2010/0280036 A1 11/2010 Ammendola et al.
2011/0046136 A1 2/2011 Almstead et al.
2011/0230483 A1 9/2011 Baettig et al.
2011/0311485 A1 12/2011 Matassa et al.
2012/0264760 A1 10/2012 Hedstrom et al.

(56) References Cited

U.S. PATENT DOCUMENTS

| | | | |
|---|---|---|---|
| 2012/0277232 | A1 | 11/2012 | Baettig et al. |
| 2013/0289083 | A1 | 10/2013 | Mautino et al. |
| 2014/0135329 | A1 | 5/2014 | Baettig et al. |

FOREIGN PATENT DOCUMENTS

| | | | |
|---|---|---|---|
| EP | 0 650 960 | A1 | 5/1995 |
| EP | 0834311 | A1 | 4/1998 |
| EP | 0 843 018 | A1 | 5/1998 |
| EP | 1 440 966 | A1 | 7/2004 |
| JP | 7-33729 | A | 2/1995 |
| JP | 10-183186 | A | 7/1998 |
| JP | 2004/107299 | A | 4/2004 |
| JP | 05-025045 | B2 | 9/2012 |
| WO | 92/019594 | A1 | 11/1992 |
| WO | 93/018007 | A1 | 9/1993 |
| WO | 93/019750 | A1 | 10/1993 |
| WO | 1995/009843 | A1 | 4/1995 |
| WO | 99/15129 | A2 | 4/1999 |
| WO | 99/016766 | A1 | 4/1999 |
| WO | 1999/015129 | A2 | 4/1999 |
| WO | 00/66559 | A1 | 11/2000 |
| WO | 03/048181 | A1 | 6/2003 |
| WO | 03/062259 | A2 | 7/2003 |
| WO | 03/064445 | A1 | 8/2003 |
| WO | 03/072592 | A1 | 9/2003 |
| WO | 2004/018449 | A1 | 3/2004 |
| WO | 2004/020414 | A1 | 3/2004 |
| WO | 2004/022547 | A1 | 3/2004 |
| WO | 2004/026841 | A1 | 4/2004 |
| WO | 2004/037768 | A2 | 5/2004 |
| WO | 2004/039762 | A1 | 5/2004 |
| WO | 2004/039766 | A1 | 5/2004 |
| WO | 2004/039827 | A2 | 5/2004 |
| WO | 2004/058733 | A1 | 7/2004 |
| WO | 2004/078163 | A2 | 9/2004 |
| WO | 2004/080980 | A1 | 9/2004 |
| WO | 2005/026158 | A1 | 3/2005 |
| WO | 2005/072681 | A2 | 8/2005 |
| WO | 2006/053109 | A1 | 5/2006 |
| WO | 2006/065721 | A2 | 6/2006 |
| WO | 2006/067445 | A2 | 6/2006 |
| WO | 2006/067446 | A1 | 6/2006 |
| WO | 2006/124874 | A2 | 11/2006 |
| WO | 2006/133391 | A2 | 12/2006 |
| WO | 2007/090749 | A2 | 8/2007 |
| WO | 2007/090752 | A1 | 8/2007 |
| WO | 2007/143557 | A2 | 12/2007 |
| WO | 2008/002671 | A2 | 1/2008 |
| WO | 2008/011072 | A2 | 1/2008 |
| WO | 2008/082487 | A2 | 7/2008 |
| WO | 2008/125296 | A1 | 10/2008 |
| WO | 2008/154221 | A2 | 12/2008 |
| WO | 2009/073620 | A2 | 6/2009 |
| WO | 2009/076593 | A1 | 6/2009 |
| WO | 2010/031750 | A1 | 3/2010 |
| WO | 2010/051188 | A1 | 5/2010 |
| WO | 2010/098488 | A1 | 9/2010 |
| WO | 2010/151747 | A2 | 12/2010 |
| WO | 2011/001931 | A1 | 1/2011 |
| WO | 2011/008931 | A2 | 1/2011 |

OTHER PUBLICATIONS

[No Author Listed] Prevention of Cystic Fibrosis. WrongDiagnosis.com. 4 pages. Website. Last Accessed Apr. 6, 2009.

Accurso et al., Effect of VX-770 in persons with cystic fibrosis and the G551D-CFTR mutation. N Engl J Med. Nov. 18, 2010;363(21):1991-2003.

Ambrogi et al., New Orgal Antidiabetic Drugs. Arzbeun-Forsch (Drug Res). 1971;21(2):200-4.

Baxter et al., A novel membrane potential-sensitive fluorescent dye improves cell-based assays for ion channels. J Biomol Screen. Feb. 2002;7(1):79-85.

Bicking et al., Pyrazine Diuretics. III. 5- and 6-Alky1, -Cycloalkyl, and -Aryl Derivatives of N-Arniclino-3-aminopyrazinecarboxanides. Pryzine Diuretics III. Jul. 1967;10:598-602.

Curran et al., Pteridine Chemistry. VI. The Synthesis and Alkaline Degradation of 3-(2-Cyanoethyl)-7-methyl-4(3H)-pteridinone and Some Related Reactions. J Org Chem. 1961;26(7):2364-8.

Davies et al., Study Group. Efficacy and safety of ivacaftor in patients aged 6 to 11 years with cystic fibrosis with a G551D mutation. Am J Respir Crit Care Med. Jun. 1, 2013;187(11):1219-25.

Finkel et al., Population patch clamp improves data consistency and success rates in the measurement of ionic currents. J Biomol Screen. Aug. 2006;11(5):488-96. Epub Jun. 7, 2006.

Hirsh et al., Evaluation of second generation amiloride analogs as therapy for cystic fibrosis lung disease. J Pharmacol Exp Ther. Dec. 2004;311(3):929-38. Epub Jul. 23, 2004.

Keir et al., Ethyl amidinoacetates in the synthesis of pyrazines. J Chem Soc Perkin I. 1978;9;1002-6.

Moody et al., Inositol polyphosphate derivative inhibits Na+ transport and improves fluid dynamics in cystic fibrosis airway epithelia. Am J Physiol Cell Physiol. Sep. 2005;289(3):C512-20. Epub Apr. 27, 2005.

Pigini et al., Analogues with a 1,20benzisoxazole nucleus of biologically active indole derivatives. III (*). Tryptamine and gramine isosters (**). Eur J Med Chem. 1975;10(1):29-32.

Ramsey et al., VX08-770-102 Study Group. CFTR potentiator in patients with cystic fibrosis and the G551D mutation. N Engl J Med. Nov. 3, 2011;365(18):1663-72.

Shepard et al., Pyrazine diuretics. VI. (Pyrazinecarboxamido)guanidines. J. Med. Chem. 1969;12(2);280-5.

Sugimoto et al., Imidazopteridines. I. Synthesis of Imidazo[1,2-c]pteridine and Its Alkyl Derivatives. Bull Chem Soc Japan. 1977-50(10):2744-7.

* cited by examiner

PYRIDINE AND PYRAZINE DERIVATIVE FOR THE TREATMENT OF CF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application *is a Reissue Application of U.S. Ser. No. 13/544,182, filed Jul. 9, 2012, now U.S. Pat. No. 8,476,269, which* is a Continuation of U.S. application Ser. No. 13/047,319, filed on Mar. 14, 2011, which claims benefit under 35 U.S.C. § 119(e) of US Provisional Application No. 61/315,509, filed Mar. 19, 2010, and U.S. Provisional Application No. 61/441,853, filed on Feb. 11, 2011, the contents of which are incorporated herein by reference in their entirety.

This invention relates to pyridine and pyrazine compounds, their preparation and use as pharmaceuticals.

Cystic fibrosis (CF) is a fatal genetic disease caused by mutations in the gene encoding the CF transmembrane conductance regulator (CFTR), a protein kinase A (PKA)-activated epithelial anion channel involved in salt and fluid transport in multiple organs, including the lung. Most CF mutations either reduce the number of CFTR channels at the cell surface (e.g., synthesis or processing mutations) or impair channel function (e.g., gating or conductance mutations) or both. There are currently no approved therapies that target CFTR directly. The present invention discloses compounds which restore or enhance the function of mutant and/or wild type CFTR to treat cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced).

In one aspect, the invention provides compounds according to Formula I:

I

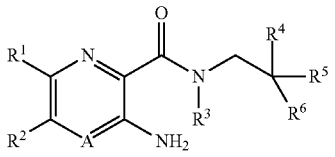

or pharmaceutically acceptable salts thereof, wherein:

A is N or $CR^{4a}$;

$R^1$ is H; $C_1$-$C_8$ alkyl optionally substituted by one or more halogen atoms; $C_2$-$C_9$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; halogen; $SO_2NR^8R^9$; $SO_2R^{19}$; S—$C_1$-$C_8$alkyl optionally substituted by one or more halogen atoms; S—$C_6$-$C_{14}$ aryl; CN; $NR^{11}R^{12}$; $C(O)NR^{13}R^{14}$; $NR^{13}SO_2R^{15}$; $NR^{13}C(O)R^{15}$, $CO_2R^{15}$, —($C_0$-$C_4$ alkyl)-$C_8$-$C_{1-4}$ aryl; or —($C_0$-$C_4$ alkyl)-3 to 14 membered heterocyclic group, wherein the heterocyclic group contains at least one heteroatom selected from N, O and S; wherein the cycloalkyl, cycloalkenyl, aryl and heterocyclyl groups are each optionally substituted by one or more Z substituents;

$R^2$ is $C_1$-$C_4$ haloalkyl;

$R^3$ and $R^{4a}$ are each independently H or $C_1$-$C_8$ alkyl optionally substituted by one or more halogen atoms;

$R^4$ is H, or $C_1$-$C_8$ alkyl optional substituted with one or more halogen;

$R^5$ is —($CH_2$), —$NR^{17}R^{18}$, —$(CH_2)_m$—OR'; $C_1$-$C_8$ alkoxy optionally substituted by one or more halogen atoms; —($C_0$-$C_4$ alkyl)-$CO_2R^{15}$; —($C_0$-$C_4$ alkyl)-$C_6$-$C_{14}$ aryl or -3 to 14 membered heterocyclic group, wherein the heterocyclic group contains at least one heteroatom selected from N, O and S; wherein the —($C_0$-$C_4$ alkyl)-$C_6$-$C_{14}$ aryl and —($C_0$-$C_4$ alkyl)-3 to 14 membered heterocyclic group are each optionally substituted by one or more Z substituents;

$R^6$ is $C_1$-$C_8$ alkyl optionally substituted by one or more halogen atoms; $C_3$-$C_{10}$ cycloalkyl; —$C_1$-$C_4$ alkyl-$C_3$-$C_8$ cycloalkyl; $C_1$-$C_8$ alkoxy optionally substituted by one or more halogen atoms; OH; CN; halogen; —($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S; wherein the cycloalkyl, cycloalkenyl, —($C_0$-$C_4$ alkyl)-$C_6$-$C_{14}$ aryl and —($C_0$-$C_4$ alkyl)-3 to 14 membered heterocyclic group are each optionally substituted by one or more Z substituents; or $R^6$ is H, and $R^5$ is —$(CH_2)_m$—$NR^{17}R^{18}$, —$(CH_2)_m$—OR', $C_1$-$C_8$ alkoxy optionally substituted by one or more halogen atoms; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; or —($C_0$-$C_4$ alkyl)-$CO_2R^{15}$, wherein —($C_0$-$C_4$ alkyl)-$C_6$-$C_{14}$ aryl and —($C_0$-$C_4$ alkyl)-3 to 14 membered heterocyclic group groups are each optionally substituted by one or more Z substituents; or $R^4$ and $R^6$ together with the carbon atoms to which they are bound form a 3 to 8 membered carbocyclic ring system; or $R^4$ and $R^5$ together form an oxo group (C═O) and $R^6$ is $C_1$-$C_4$ alkyl optionally substituted by one or more halogen atoms; $C_1$-$C_4$ alkoxy optionally substituted by one or more halogen atoms; —($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S, wherein the aryl and heterocyclyl groups are each optionally substituted by one or more Z substituents; or $R^5$ and $R^6$ together with the carbon atoms to which they are bound a 5 to 8 membered heterocyclic ring system containing one or more heteroatoms selected from N, O and S, wherein the ring system is optionally substituted by one or more Z substituents; or $R^4$ and $R^5$ and $R^6$ together with the carbon atoms to which they are bound form a 5 to 8 membered heterocyclic ring system containing one or more heteroatoms selected from N, O and S, wherein the ring system is optionally substituted by one or more Z substituents;

R' is H, or $C_1$-$C_8$ alkyl optional substituted with one or more halogen;

m is 0, 1, 2 or 3;

$R^8$, $R^{11}$, $R^{13}$ and $R^{17}$ are each independently H, $C_1$-$C_8$ alkyl optionally substituted by one or more halogen atoms, $C_3$-$C_{10}$ cycloalkyl or —($C_1$-$C_4$ alkyl)-$C_3$-$C_8$ cycloalkyl;

$R^9$, $R^{10}$, $R^{12}$, $R^{14}$, $R^{15}$, $R^{16}$ and $R^{18}$ are each independently H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; —($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S, wherein the cycloalkyl, cycloalkenyl, aryl and heterocyclyl groups are each optionally substituted by one or more Z substituents; or $R^8$ and $R^9$, $R^{11}$ and $R^{12}$, $R^{13}$ and $R^{14}$, and $R^{17}$ and $R^{18}$ together with the nitrogen atom to which they are attached may form a 4 to 14 membered heterocyclic group optionally substituted by one or more Z substituents;

Z is independently OH, aryl, O-aryl, benzyl, O-benzyl, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups or $C_1$-$C_4$ alkoxy, $NR^{18}(SO_2)R^{21}$, $(SO_2)NR^{19}R^{21}$, $(SO_2)R^{21}$, $NR^{18}C(O)R^{21}$, $C(O)NR^{19}R^{21}$, $NR^{18}C(O)NR^{19}R^{21}$, $NR^{18}C(O)OR^{19}$, $NR^{19}R^{21}$, $C(O)OR^{19}$, $C(O)R^{19}$, $SR^{19}$, $OR^{19}$, oxo, CN, $NO_2$, halogen or a 3 to 14 membered heterocyclic group, wherein the heterocyclic group contains at least one heteroatom selected from N, O and S;

$R^{19}$ and $R^{21}$ are each independently H; $C_1$-$C_8$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclic group, the heterocyclic group including one or more heteroatoms selected from N, O and S, optionally substituted by one or more groups selected from halogen, oxo, $C_1$-$C_6$ alkyl and $C(O)C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclic group, the heterocyclic group including one or more heteroatoms selected from N, O and S, optionally substituted by one or more groups selected from halogen, $C_1$-$C_6$ alkyl or $C(O)C_1$-$C_6$ alkyl; wherein the alkyl groups are optionally substituted by one or more halogen atoms, $C_1$-$C_4$ alkoxy, $C(O)NH_2$, $C(O)NHC_1$-$C_6$ alkyl or $C(O)N(C_1$-$C_6$ alkyl$)_2$; or $R^{19}$ and $R^{21}$ together with the nitrogen atom to which they attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy.

Various embodiments of the invention are described herein. It will be recognized that features specified in each embodiment may be combined with other specified features to provide further embodiments.

In an embodiment of the invention as described anywhere herein, A is N.

In an embodiment of the invention as described anywhere herein, A is $CR^{4a}$.

In an embodiment of the invention as described anywhere herein, $R^1$ is selected from H; $C_1$-$C_8$ alkyl optionally substituted by one or more halogen atoms; $C_1$-$C_8$ alkoxy optionally substituted by one or more halogen atoms; halogen; $C_6$-$C_{14}$ aryl; —($C_0$-$C_4$ alkyl)-3 to 14 membered heterocyclic group, wherein the heterocyclic group contains at least one heteroatom selected from N, O and S; and $NR^{11}R^{12}$, wherein the aryl and heterocyclic groups are each optionally substituted by one or more Z substituents.

In an embodiment of the invention as described anywhere herein, $R^1$ is $C_1$-$C_4$ alkyl optional substituted by one or more halogen atoms. For example, —$CH_3$ or $CF_3$.

In an embodiment of the invention as described anywhere herein, $R^1$ is $C_1$-$C_4$ alkoxy optional substituted by one or more halogen atoms. For example, —$OCH_3$ or —$OCF_3$.

In an embodiment of the invention as described anywhere herein, $R^1$ is aryl, wherein aryl is phenyl optionally substituted by one or more Z substituents, specific example are 4-fluorophenyl, 4-chloro-2-methylphenyl, or 2,4-dichlorophenyl.

In an embodiment of the invention as described anywhere herein, $R^1$ is 6 membered heterocyclyl group, wherein 6 membered heterocyclyl group is pyridyl optionally substituted by one or more Z substituents, specific example is 1-methyl-4-pyridyl.

In an embodiment of the invention as described anywhere herein, $R^1$ is Br, —$CH_3$, —$CF_3$, —$OCH_3$, —$OCF_3$, 4-fluorophenyl, 4-chloro-2-methylphenyl, or 2,4-dichlorophenyl.

In an embodiment of the invention as described anywhere herein, $R^2$ is $CF_3CF_2$—, $(CF_3)_2CH$—, $CH_3$—$CF_2$—, $CF_3CF_2$—, $CF_3$, $CF_2H$—, $CH_3$—$CCl_2$—, $CF_3CFClH$—, $CBr_3$, $CBr_2H$—$CF_3CF_2CHCF_3$ or $CF_3CF_2CF_2CF_2$—.

In an embodiment of the invention as described anywhere herein, $R^2$ is $CF_3$.

In an embodiment of the invention as described anywhere herein, $R^3$ is H or methyl.

In a further embodiment of the invention as described anywhere herein, $R^{4a}$ is H.

An embodiment of the invention, as defined above provides a compound, where $R^5$ provides a heteroatom two carbons from the amide nitrogen, wherein the heteroatom is oxygen or nitrogen.

An embodiment of the invention as defined above provides a compound according to Formula I, wherein $R^4$ is H, $C_1$-$C_4$ alkyl optionally substituted by one or more halogen atoms or not present;

$R^5$ is $C_1$-$C_4$ alkoxy optionally substituted by one or more halogen atoms; —$(CH_2)_m$—$NR^{17}R^{18}$; —$(CH_2)_m$—OR', or OH;

m is 0, or 1;

$R^6$ is $C_1$-$C_4$ alkyl optionally substituted by one or more halogen atoms; $C_1$-$C_4$ alkoxy optionally substituted by one or more halogen atoms; OH; CN; halogen; —($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S, wherein the aryl and heterocyclyl groups are each optionally substituted by one or more Z substituents; or $R^4$ and $R^5$ together form an oxo group (C═O); or $R^5$ and $R^6$ together with the carbon atoms to which they are bound form a 5 to 8 membered heterocyclic ring system containing one or more heteroatoms selected from N, O and S, wherein the ring system is optionally substituted by one or more Z substituents;

$R^{17}$ and $R^{18}$ are each independently H; or $C_1$-$C_4$ alkyl optionally substituted by one or more halogen atoms.

An embodiment of the invention as defined above provides compounds according to Formula I, wherein A is $CR^{4a}$;

$R^1$ is halogen, $C_1$-$C_4$ alkyl optionally substituted by one or more halogen atoms, or $C_1$-$C_4$ alkoxy optionally substituted by one or more halogen atoms;

$R^2$ is $C_1$-$C_4$ haloalkyl;

$R^3$ is H;

$R^4$ is H or Me;

$R^{4a}$ is H;

$R^5$ is —$(CH_2)_m$—$NR^{17}R^{18}$; —$(CH_2)_m$—OR'; or OH;

m is 0, or 1;

$R^6$ is $C_1$-$C_4$ alkyl optionally substituted by one or more halogen atoms; or $R^5$ and $R^6$ together with the carbon atoms to which they are bound form a 5 to 6 membered heterocyclic ring system containing one or more heteroatoms selected from N, O and S, wherein the ring system is optionally substituted by one or more Z substituents; and $R^{17}$ and $R^{18}$ are each independently H; or $C_1$-$C_4$ alkyl optionally substituted by one or more halogen atoms.

An embodiment of the invention as defined above provides compounds according to Formula I, wherein A is $CR^{4a}$;

$R^1$ is halogen, $C_1$-$C_4$ alkyl optionally substituted by one or more halogen atoms, or $C_1$-$C_4$ alkoxy optionally substituted by one or more halogen atoms;

$R^2$ is $C_1$-$C_4$ haloalkyl;

$R^3$ is H;

$R^{4a}$ is H;

$R^4$ and $R^5$ together form an oxo group (C═O); and $R^6$ is $C_1$-$C_4$ alkyl optionally substituted by one or more halogen atoms; $C_1$-$C_4$ alkoxy optionally substituted by one or more halogen atoms; —($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S, wherein the aryl and heterocyclyl groups are each optionally substituted by one or more Z substituents.

An embodiment of the invention as defined above provides compounds according to Formula I, wherein A is $CR^{4a}$;

$R^1$ is $C_1$-$C_4$ alkyl optionally substituted by one or more halogen atoms;

$R^2$ is $C_1$-$C_4$ haloalkyl;

$R^3$ is H;

$R^4$ is H or Me;

$R^{4a}$ is H;

$R^5$ is —$(CH_2)_m$—$NR^{17}R^{18}$; —$(CH_2)_m$ —OR'; or OH;

m is 0, or 1;

$R^6$ is $C_1$-$C_4$ alkyl optionally substituted by one or more halogen atoms; or $R^5$ and $R^6$ together with the carbon atoms to which they are bound form a 5 to 6 membered heterocyclic ring system containing one or more heteroatoms selected from N, O and S, wherein the ring system is optionally substituted by one or more Z substituents; and $R^{17}$ and $R^{18}$ are each independently H; or $C_1$-$C_4$ alkyl optionally substituted by one or more halogen atoms.

An embodiment of the invention as defined above provides compounds according to Formula I, wherein A is $CR^{4a}$;

$R^1$ is $C_1$-$C_4$ alkoxy optionally substituted by one or more halogen atoms;

$R^2$ is $C_1$-$C_4$ haloalkyl;

$R^3$ is H;

$R^4$ is H or Me;

$R^{4a}$ is H;

$R^5$ is —$(CH_2)_m$—$NR^{17}R^{18}$; —$(CH_2)_m$—OR; or OH;

m is 0, or 1;

$R^6$ is $C_1$-$C_4$ alkyl optionally substituted by one or more halogen atoms; or $R^5$ and $R^6$ together with the carbon atoms to which they are bound form a 5 to 6 membered heterocyclic ring system containing one or more heteroatoms selected from N, O and S, wherein the ring system is optionally substituted by one or more Z substituents; and $R^{17}$ and $R^{18}$ are each independently H; or $C_1$-$C_4$ alkyl optionally substituted by one or more halogen atoms.

An embodiment of the invention as defined above provides compounds according to Formula I, wherein A is $CR^{4a}$;

$R^1$ is $C_1$-$C_4$ alkoxy optionally substituted by one or more halogen atoms;

$R^2$ is $C_1$-$C_4$ haloalkyl;

$R^3$ is H;

$R^4$ is H or Me;

$R^{4a}$ is H;

$R^5$ is —$NR^{17}R^{18}$; or OH;

$R^6$ is $C_1$-$C_4$ alkyl optionally substituted by one or more halogen atoms; or $R^5$ and $R^6$ together with the carbon atoms to which they are bound form a 5 to 6 membered heterocyclic ring system containing one or more heteroatoms selected from N, O and S, wherein the ring system is optionally substituted by one or more Z substituents; and $R^{17}$ and $R^{18}$ are each independently H; or $C_1$-$C_4$ alkyl optionally substituted by one or more halogen atoms.

An embodiment of the invention as defined above provides compounds according to Formula I, wherein A is $CR^{4a}$;

$R^1$ is $C_1$-$C_4$ alkyl optionally substituted by one or more halogen atoms;

$R^2$ is $C_1$-$C_4$ haloalkyl;

$R^3$ is H;

$R^4$ is H or Me;

$R^{4a}$ is H;

$R^5$ is —$NR^{17}R^{18}$; or OH;

$R^6$ is $C_1$-$C_4$ alkyl optionally substituted by one or more halogen atoms; and $R^{17}$ and $R^{18}$ are each independently H; or $C_1$-$C_4$ alkyl optionally substituted by one or more halogen atoms.

An embodiment of the invention as defined above provides compounds according to Formula I, wherein A is $CR^{4a}$;

$R^1$ is $C_1$-$C_4$ alkoxy optionally substituted by one or more halogen atoms;

$R^2$ is $C_1$-$C_4$ haloalkyl;

$R^3$ is H;

$R^4$ is H or Me;

$R^{4a}$ is H;

$R^5$ is —$NR^{17}R^{18}$; or OH;

$R^6$ is $C_1$-$C_4$ alkyl optionally substituted by one or more halogen atoms; and $R^{17}$ and $R^{18}$ are each independently H; or $C_1$-$C_4$ alkyl optionally substituted by one or more halogen atoms.

In an embodiment of the invention as described anywhere herein, wherein

Z is independently OH, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $NR^{19}R^{21}$, $C(O)OR^{19}$, $C(O)R^{19}$, $SR^{19}$, $OR^{19}$, CN, $NO_2$, or halogen;

$R^{19}$ and $R^{21}$ are each independently H; $C_1$-$C_4$ alkyl; $C_3$-$C_6$ cycloalkyl; or $C_1$-$C_4$ alkoxy-$C_1$-$C_4$ alkyl, wherein all alkyls are optionally substituted with halogens.

In an embodiment of the invention as described anywhere herein, wherein

Z is independently OH, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $C(O)OR^{19}$, $C(O)R^{19}$, $OR^{19}$, CN, or halogen;

$R^{19}$ is H; $C_1$-$C_4$ alkyl; $C_3$-$C_6$ cycloalkyl; or $C_1$-$C_4$ alkoxy-$C_1$-$C_4$ alkyl, wherein all alkyl are optionally substituted with halogens.

In an embodiment of the invention as described anywhere herein, wherein

Z is independently, $C_1$-$C_4$ alkyl optionally substituted by one or more halogen atoms, $C_1$-$C_4$ alkoxy or halogen.

Another embodiment of the invention as defined above provides compounds with substantially pure enantiomers with the R configuration.

Another embodiment of the invention as defined above provides compounds with substantially pure enantiomers with the S configuration.

Certain compounds of Formula I include compounds of Formula II:

II

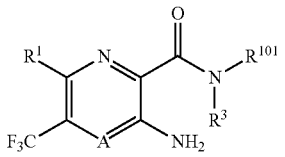

or a pharmaceutically acceptable salt thereof, wherein A, $R^1$, $R^2$ and $R^3$ have the definitions of Formula I and $R^{101}$ is

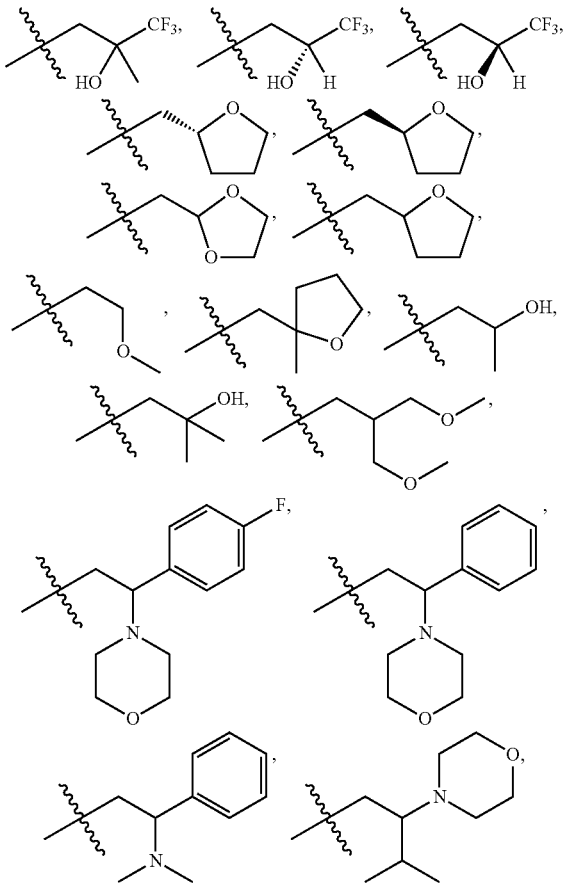

-continued

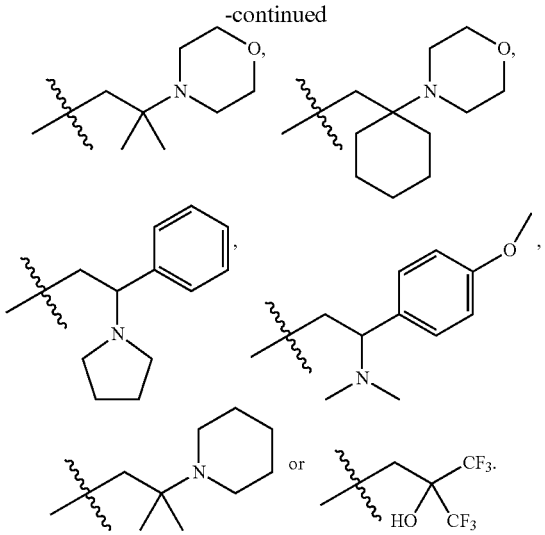

In a further embodiment of Formula II of the invention herein, A is $CR^{4a}$, wherein $R^{4a}$ is H.

In a further embodiment of Formula II of the invention herein, $R^1$ is selected from H; $C_1$-$C_4$ alkyl optionally substituted by one or more halogen atoms; $C_1$-$C_4$ alkoxy optionally substituted by one or more halogen atoms; halogen; $C_6$-$C_{14}$ aryl; —($C_0$-$C_4$ alkyl)-3 to 14 membered heterocyclic group, wherein the heterocyclic group contains at least one heteroatom selected from N, O and S; and $NR^{11}R^{12}$, wherein the aryl and heterocyclic groups are each optionally substituted by one or more Z substituents.

In a further embodiment of Formula II of the invention wherein, $R^1$ is $C_1$-$C_4$ alkyl optional substituted by one or more halogen atoms, $C_1$-$C_4$ alkoxy optionally substituted by one or more halogen atoms; halogen; $C_6$ aryl; or 6 membered heterocyclic group, wherein the heterocyclic group contains at least one heteroatom selected from N, O and S, wherein the aryl and heterocyclic groups are each optionally substituted by one or more Z substituents.

In a further embodiment of Formula II of the invention wherein, $R^1$ is $C_1$-$C_4$ alkyl optional substituted by one or more halogen atoms, $C_1$-$C_4$ alkoxy optionally substituted by one or more halogen atoms; or halogen.

In a further embodiment of Formula II of the invention herein, $R^3$ is H or methyl.

An embodiment of the invention as defined above provides compounds according to Formula II, wherein A is $CR^{4a}$;

$R^1$ is halogen;

$R^3$ is H;

$R^{4a}$ is H;

$R^{101}$ is

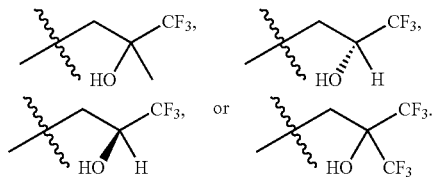

An embodiment of the invention as defined above provides compounds according to Formula II, wherein A is $CR^{4a}$;

$R^1$ is $C_1$-$C_4$ alkyl optionally substituted by one or more halogen atoms;

$R^3$ is H;
$R^{4a}$ is H;
$R^{101}$ is

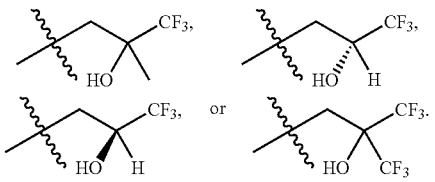

An embodiment of the invention as defined above provides compounds according to Formula II, wherein
A is $CR^{4a}$;
$R^1$ is $C_1$-$C_4$ alkoxy optionally substituted by one or more halogen atoms;
$R^3$ is H;
$R^{4a}$ is H;
$R^{101}$ is

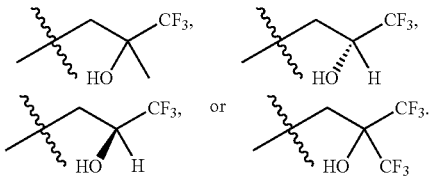

An embodiment of the invention as defined above provides compounds according to Formula II, wherein
A is $CR^{4a}$;
$R^1$ is halogen, $C_1$-$C_4$ alkyl optionally substituted by one or more halogen atoms, or $C_1$-$C_4$ alkoxy optionally substituted by one or more halogen atoms;
$R^3$ is H;
$R^{4a}$ is H;
$R^{101}$ is

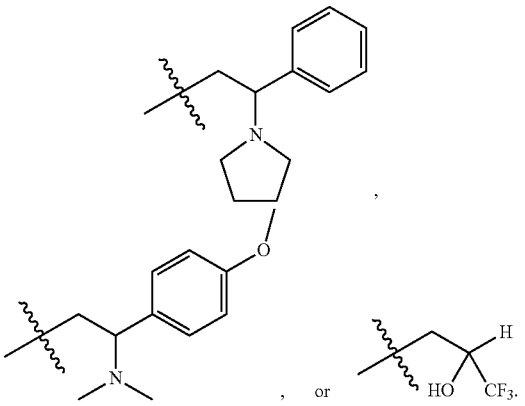

An embodiment of the invention as defined above provides compounds according to Formula II, wherein
A is $CR^{4a}$;
$R^1$ is halogen, $C_1$-$C_4$ alkyl optionally substituted by one or more halogen atoms, or $C_1$-$C_4$ alkoxy optionally substituted by one or more halogen atoms;
$R^3$ is H;
$R^{4a}$ is H;
$R^{101}$ is

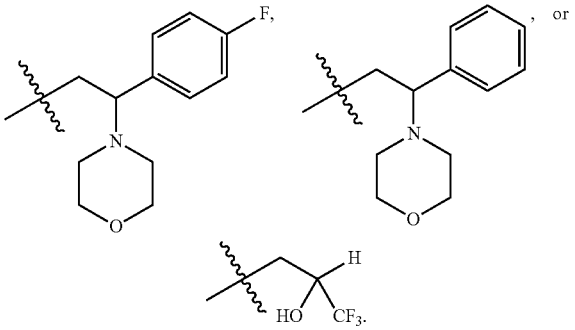

An embodiment of the invention as defined above provides compounds according to Formula II, wherein
A is $CR^{4a}$;
$R^1$ is halogen, $C_1$-$C_4$ alkyl optionally substituted by one or more halogen atoms, or $C_1$-$C_4$ alkoxy optionally substituted by one or more halogen atoms;
$R^3$ is H;
$R^{4a}$ is H;
$R^{101}$ is

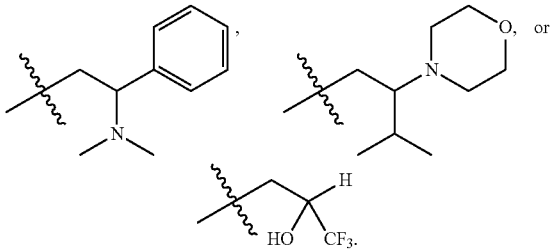

Another embodiment of the invention as defined above provides compounds according to Formula I and Formula II, represented by 3-amino-6-bromo-N-(imidazo[1,2-a]pyridin-2-ylmethyl)-5-(trifluoromethyl)pyrazine-2-carboxamide;
3-amino-6-bromo-N-((1-methyl-1H-imidazol-4-yl)methyl)-5-(trifluoromethyl)pyrazine-2-carboxamide;
3-amino-6-bromo-N-((1-methyl-1H-pyrazol-3-yl)methyl)-5-(trifluoromethyl)pyrazine-2-carboxamide;
3-amino-N-(2-(4-fluorophenyl)-2-oxoethyl)-6-(1-methyl-1H-indol-6-yl)-5-(trifluoromethyl)picolinamide;
3-amino-6-bromo-N-((1-methyl-1H-imidazol-2-yl)methyl)-5-(trifluoromethyl)pyrazine-2-carboxamide;
3-amino-6-(6-(3-(dimethylamino)propoxy)pyridin-3-yl)-N-(2-(4-fluorophenyl)-2-oxoethyl)-5-(trifluoromethyl)pyrazine-2-carboxamide;
(R)-3-amino-6-bromo-N-((4-methylpiperazin-2-yl)methyl)-5-(trifluoromethyl)pyrazine-2-carboxamide;
3-amino-6-bromo-N-((1-methyl-1H-imidazol-5-yl)methyl)-5-(trifluoromethyl)pyrazine-2-carboxamide;
3-amino-6-(3-(N,N-dimethylsulfamoyl)phenyl)-N-(2-(4-fluorophenyl)-2-oxoethyl)-5-(trifluoromethyl)picolinamide;
3-amino-6-bromo-N-isobutyl-N-methyl-5-(trifluoromethyl)pyrazine-2-carboxamide;
3-amino-6-bromo-N-((1-methyl-1H-pyrazol-5-yl)methyl)-5-(trifluoromethyl)pyrazine-2-carboxamide;

(3-amino-6-bromo-5-(trifluoromethyl)pyrazin-2-yl)(4-methylpiperazin-1-yl)methanone;

3-amino-6-bromo-N-(2-(pyridin-4-yl)ethyl)-5-(trifluoromethyl)pyrazine-2-carboxamide;

3-amino-N-(2-(4-fluorophenyl)-2-oxoethyl)-6-(1-oxo-1,2,3,4-tetrahydroisoquinolin-6-yl)-5-(trifluoromethyl)picolinamide;

3-amino-6-(4-carbamoyl-2-methylphenyl)-N-(2-(4-fluorophenyl)-2-oxoethyl)-5-(trifluoromethyl)picolinamide;

3-amino-6-bromo-N-(2-(pyridin-3-yl)ethyl)-5-(trifluoromethyl)pyrazine-2-carboxamide;

3-amino-6-(3,4-dimethylphenyl)-N-(2-(4-fluorophenyl)-2-oxoethyl)-5-(trifluoromethyl)picolinamide;

3-amino-N-benzyl-6-bromo-N-methyl-5-(trifluoromethyl)pyrazine-2-carboxamide;

(S)-3-amino-6-bromo-N-((1-ethylpyrrolidin-2-yl)methyl)-5-(trifluoromethyl)pyrazine-2-carboxamide; or 3-amino-6-bromo-N-(imidazo[1,5-a]pyridin-1-ylmethyl)-5-(trifluoromethyl)pyrazine-2-carboxamide.

Another embodiment of the invention as defined above provides compounds according to Formula I, represented by 3-Amino-6-methoxy-5-trifluoromethyl-pyridine-2-carboxylic acid ((S)-3,3,3-trifluoro-2-hydroxy-2-methyl-propyl)-amide;

3-Amino-6-methoxy-5-trifluoromethyl-pyridine-2-carboxylic acid ((R)-3,3,3-trifluoro-2-hydroxy-2-methyl-propyl)-amide;

Methyl 3-(3-amino-6-bromo-5-(trifluoromethyl)picolinamido)propanoate;

3-Amino-N-(benzo[d]isoxazol-3-ylmethyl)-6-bromo-5-(trifluoromethyl) picolinamide;

3-Amino-6-(oxazol-2-yl)-N-(3,3,3-trifluoro-2-hydroxy-2-methylpropyl)-5-(trifluoromethyl)picolinamide;

3-Amino-6-bromo-N-(3,3,3-trifluoro-2-methoxy-2-methylpropyl)-5-(trifluoromethyl)picolinamide;

3-amino-N-(2-hydroxy-3-methyl-2-(trifluoromethyl)butyl)-6-methoxy-5-(trifluoromethyl)picolinamide;

3-Amino-6-cyclopropyl-N-(3,3,3-trifluoro-2-hydroxy-2-methylpropyl)-5-(trifluoromethyl)picolinamide;

3-Amino-6-methoxy-N-(3,3,3-trifluoro-2-hydroxy-2-(trifluoromethyl)propyl)-5-(trifluoro methyl)picolinamide;

5-amino-N-(3,3,3-trifluoro-2-hydroxy-2-methylpropyl)-3-(trifluoromethyl)-2,4'-bipyridine-6-carboxamide;

3-Amino-6-bromo-5-trifluoromethyl-pyridine-2-carboxylic acid (3-methyl-2-oxo-butyl)-amide;

3-Amino-6-bromo-5-trifluoromethyl-pyrazine-2-carboxylic acid [2-(4-fluoro-phenyl)-2-oxo-ethyl]-amide;

3-Amino-6-furan-2-yl-5-trifluoromethyl-pyrazine-2-carboxylic acid [2-(2-methoxy-phenyl)-ethyl]-amide;

3-Amino-6-(1-methyl-1H-pyrazol-4-yl)-N-(3,3,3-trifluoro-2-hydroxy-2-methylpropyl)-5-(trifluoromethyl)picolinamide;

3-amino-N-(3,3,3-trifluoro-2-hydroxy-2-methylpropyl)-5,6-bis(trifluoromethyl)pyrazine-2-carboxamide;

N-(2-(1H-imidazol-2-yl)propyl)-3-amino-6-bromo-5-(trifluoromethyl)pyrazine-2-carboxamide;

3-Amino-6-bromo-N-(2-morpholinoethyl)-5-(trifluoromethyl)pyrazine-2-carboxamide;

(S)-3-amino-6-ethoxy-N-(3,3,3-trifluoro-2-hydroxy-2-methylpropyl)-5-(trifluoro methyl)picolinamide;

3-Amino-6-(pyrrolidin-1-yl)-N-(3,3,3-trifluoro-2-hydroxy-2-methylpropyl)-5-(trifluoromethyl)picolinamide;

3-Amino-N-(2-amino-3,3,3-trifluoro-2-methylpropyl)-6-methoxy-5-(trifluoromethyl) picolinamide; or 3-Amino-6-methoxy-N-(3,3,3-trifluoro-2-(4-methoxybenzylamino)-2-methylpropyl)-5-(trifluoromethyl)picolinamide.

It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments. It is understood by those skilled in the art that combinations of substituents where not possible are not an aspect of the present invention.

Especially preferred specific compounds of formula (I) or formula (II) are those described hereinafter in the Examples.

DEFINITIONS

Terms used in the specification have the following meanings:

"Optionally substituted" means the group referred to can be substituted at one or more positions by any one or any combination of the radicals listed thereafter.

"Optionally substituted by one or more Z groups" denotes that the relevant group may include one or more substituents, each independently selected from the groups included within the definition of Z. Thus, where there are two or more Z group substituents, these may be the same or different.

"Halo" or "halogen", as used herein, may be fluorine, chlorine, bromine or iodine.

"$C_1$-$C_8$-Alkyl", as used herein, denotes straight chain or branched alkyl having 1-8 carbon atoms. If a different number of carbon atoms is specified, such as $C_6$ or $C_3$, then the definition is to be amended accordingly, such as "$C_1$-$C_4$-Alkyl" will represent methyl, ethyl, propyl, isopropyl, butyl, isobutyl, sec-butyl and tert-butyl.

"$C_1$-$C_8$-Alkoxy", as used herein, denotes straight chain or branched alkoxy having 1-8 carbon atoms. If a different number of carbon atoms is specified, such as $C_6$ or $C_3$, then the definition is to be amended accordingly, such as "$C_1$-$C_4$-Alkoxy" will represent methoxy, ethoxy, propoxy, isopropoxy, butoxy, isobutoxy, sec-butoxy and tert-butoxy.

"$C_1$-$C_4$-Haloalkyl", as used herein, denotes straight chain or branched alkyl having 1-4 carbon atoms with at least one hydrogen substituted with a halogen. If a different number of carbon atoms is specified, such as $C_6$ or $C_3$, then the definition is to be amended accordingly, such as "$C_1$-$C_4$-Haloalkyl" will represent methyl, ethyl, propyl, isopropyl, butyl, isobutyl, sec-butyl and tert-butyl that have at least one hydrogen substituted with halogen, such as where the halogen is fluorine: $CF_3CF_2$—, $(CF_3)_2CH$—, $CH_3$—$CF_2$—, $CF_3CF_2$—, $CF_3$, $CF_2H$—, $CF_3CF_2CHCF_3$ or $CF_3CF_2CF_2CF_2$—.

"$C_3$-$C_{15}$-Cycloalkyl group", as used herein, denotes a cycloalkyl group having 3-to 15-ring carbon atoms that is saturated or partially saturated, such as a $C_3$-$C_8$-cycloalkyl. Examples of $C_3$-$C_{15}$-cycloalkyl groups include but are not limited to cyclopropyl, cyclobutyl, cyclopentyl, cyclohexyl, cycloheptyl or cyclooctyl or a bicyclic group, such as bicyclooctyl, bicyclononyl including indanyl and indenyl and bicyclodecyl. If a different number of carbon atoms is specified, such as $C_6$, then the definition is to be amended accordingly.

"aryl" or "$C_6$-$C_{15}$-Aromatic carbocyclic group", as used herein, denotes an aromatic group having 6- to 15-ring carbon atoms. Examples of $C_6$-$C_{15}$-aromatic carbocyclic groups include, but are not limited to, phenyl, phenylene, benzenetriyl, naphthyl, naphthylene, naphthalenetriyl or anthrylene. If a different number of carbon atoms is specified, such as $C_{10}$, then the definition is to be amended accordingly.

"4- to 8-Membered heterocyclic group", "5- to 6-membered heterocyclic group", "3- to 10-membered heterocyclic group", "3- to 14-membered heterocyclic group", "4- to 14-membered heterocyclic group" and "5- to 14-membered heterocyclic group", refers, respectively, to 4- to 8-membered, 5- to 6-membered, 3- to 10-membered, 3- to 14-membered, 4- to 14-membered and 5- to 14-membered heterocyclic rings containing at least one ring heteroatom selected from the group consisting of nitrogen, oxygen and sulphur, which may be saturated, partially saturated or unsaturated (aromatic). The heterocyclic group includes single ring groups, fused ring groups and bridged groups. Examples of such heterocyclic groups include, but are not limited to, furan, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, pyrrolidinone, morpholine, triazine, oxazine, tetrahydrofuran, tetrahydrothiophene, tetrahydrothiopyran, tetrahydropyran, 1,4-dioxane, 1,4-oxathiane, indazole, quinoline, indazole, indole, 8-aza-bicyclo[3.2.1]octane or thiazole.

A second aspect of the invention provides a compound of Formula (I), (II) or (III) as defined anywhere herein for use as a pharmaceutical.

A further aspect of the invention provides a compound of Formula (I), (II) or (III) for use in the treatment of an inflammatory or allergic condition, particularly an inflammatory or obstructive airways disease or mucosal hydration. Such conditions include, for example, cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced).

A still further aspect of the present invention provides for the use of a compound of formula (I), (II) or (III), as defined in any of the aforementioned embodiments, in free or pharmaceutically acceptable salt form, for the manufacture of a medicament for the treatment of an inflammatory or allergic condition, particularly an inflammatory or obstructive airways disease or mucosal hydration.

An embodiment of the present invention provides for the use of a compound of formula (I), (II) or (III), as defined in any of the aforementioned embodiments, in free or pharmaceutically acceptable salt form, for the manufacture of a medicament for the treatment of an inflammatory or allergic condition selected from cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced).

An embodiment of the present invention provides method for the prevention or treatment of a CFTR mediated condition or disease comprising administering an effective amount of at least one compound as described herein to a subject in need of such treatment. Such CFTR mediated condition or disease are selected from cystic fibrosis, primary ciliary dyskinesia, chronic bronchitis, chronic obstructive pulmonary disease, asthma, respiratory tract infections, lung carcinoma, xerostomia and keratoconjunctivitis sire, or constipation (IBS, IBD, opioid induced).

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, and sulfosalicylic acid.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds of the present invention, including their salts, can also be obtained in the form of their hydrates, or include other solvents used for their crystallization.

Compounds of the invention, i.e. compounds of formula (I), (II) or (III) that contain groups capable of acting as donors and/or acceptors for hydrogen bonds may be capable of forming co-crystals with suitable co-crystal formers. These co-crystals may be prepared from compounds of formula (I), (II) or (III) by known co-crystal forming procedures. Such procedures include grinding, heating, co-subliming, co-melting, or contacting in solution compounds of formula (I), (II) or (III) with the co-crystal former under crystallization conditions and isolating co-crystals thereby formed. Suitable co-crystal formers include those described in WO 2004/078163. Hence the invention further provides co-crystals comprising a compound of formula (I), (II) or (III).

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis- (Z)- or trans- (E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O' p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$, $^{13}C$, and $^{14}C$ are present. Such isotopically labeled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I), (II) or (III). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of formula (I), (II) or (III) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Synthesis

Generally, compounds according to Formula I, II or III can be synthesized by the routes described in Scheme 1, 2 and 3 and the Examples.

When A is CH the pyridinyl moiety may be synthesized according to the general scheme 1 shown below.

Scheme 1

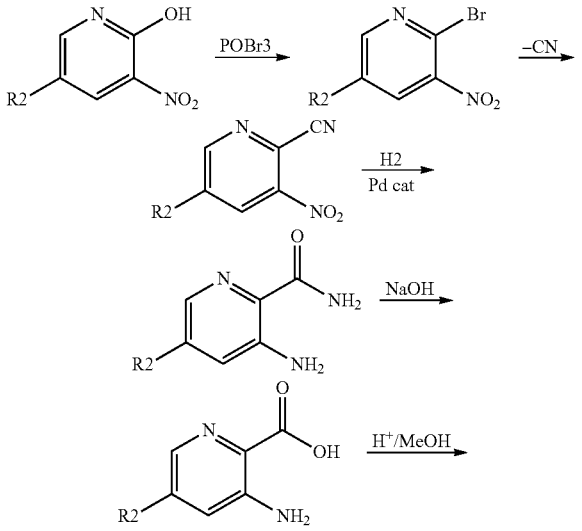

-continued

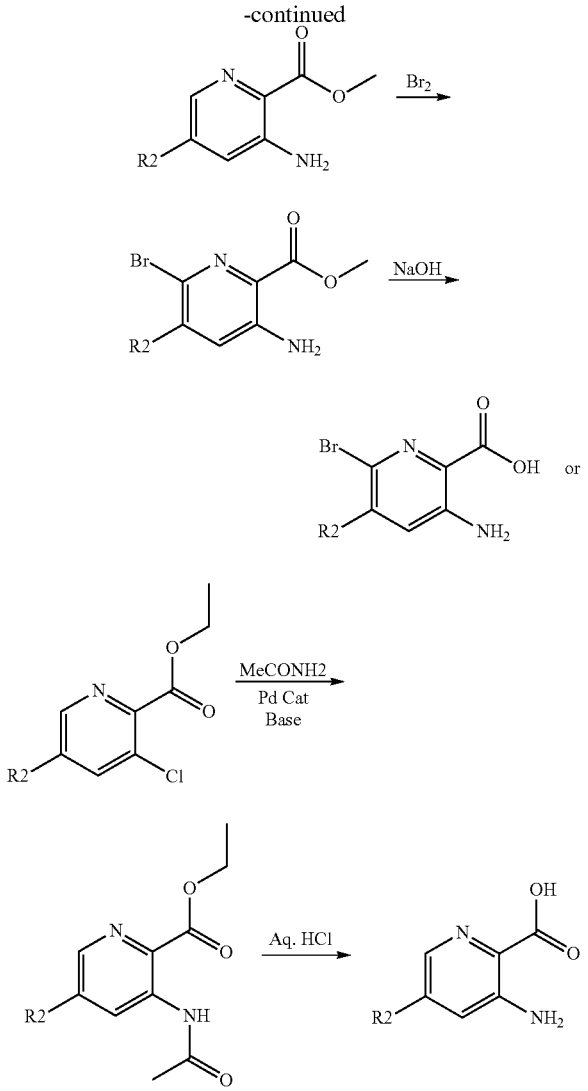

When A is nitrogen, the pyrazine moiety may be synthesized according to the general scheme 2 shown below.

Scheme 2

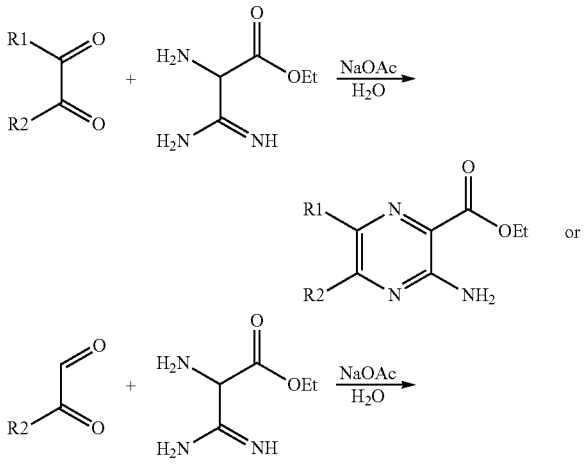

-continued

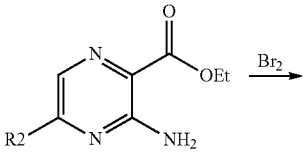

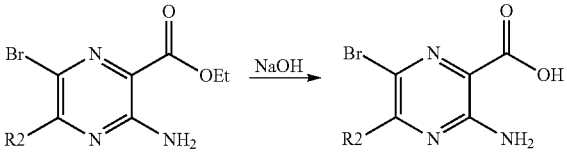

The right hand side of the moiety is typically added via an amide formation reaction as shown below in general scheme 3.

Scheme 3

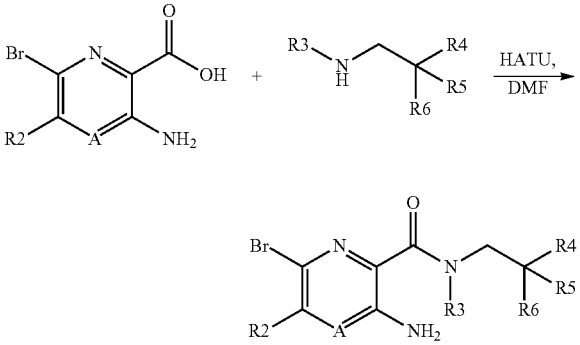

HATU (2-(1H-7-Azabenzotriazol-1-yl)-1,1,3,3-tetramethyl uronium hexafluorophosphate Methanaminium) is a peptide coupling agent. A skilled artisan would understand that other coupling agents cold possibly work. The halogen group in the above schemes can be replaced with other groups by choosing the appropriate nucleophile and catalyst. Protection of the Aryl NH2 group may be required and is represented by P. The schemes 4-7 below are some representative examples.

Scheme 4

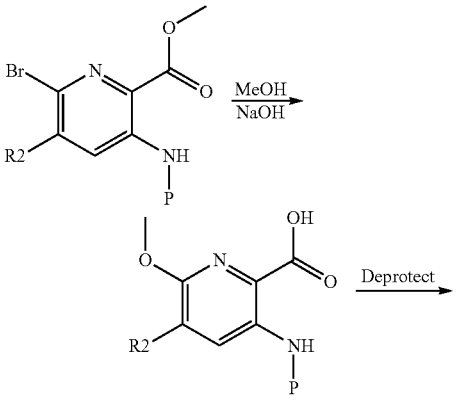

-continued

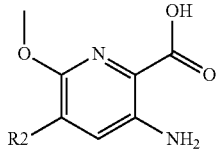

Scheme 5

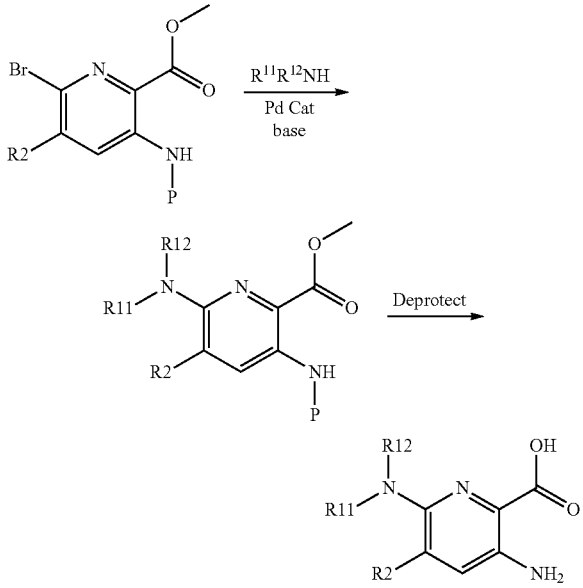

Scheme 6

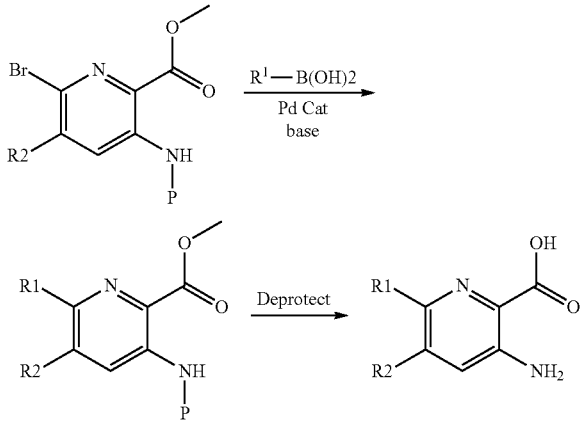

Scheme 7

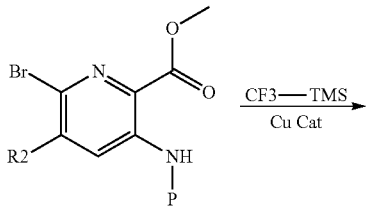

-continued

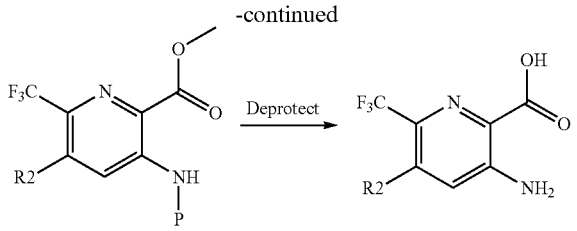

The skilled person will appreciate that the general synthetic routes detailed above show common reactions to transform the starting materials as required. The specific reaction conditions are not provided, but these are well known to those skilled in the art and appropriate conditions considered to be within the skilled person's common general knowledge.

The starting materials are either commercially available compounds or are known compounds and can be prepared from procedures described in the organic chemistry art.

Compounds of formula (I), (II) or (III), in free form, may be converted into salt form, and vice versa, in a conventional manner understood by those skilled in the art. The compounds in free or salt form can be obtained in the form of hydrates or solvates containing a solvent used for crystallisation. Compounds of formula (I), (II) or (III) can be recovered from reaction mixtures and purified in a conventional manner. Isomers, such as stereoisomers, may be obtained in a conventional manner, e.g., by fractional crystallisation or asymmetric synthesis from correspondingly asymmetrically substituted, e.g., optically active, starting materials.

The compounds of formula (I), (II) or (III) can be prepared, e.g., using the reactions and techniques described below and in the Examples. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula (I), (II) or (III) into another compound of formula (I), (II) or (III). Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are March's Organic Chemistry, 5$^{th}$ Edition, Wiley and Chichester, Eds. (2001); Comprehensive Organic Transformations, Larock, Ed., VCH (1989); Comprehensive Organic Functional Group Transformations, Katritzky et al. (series editors), Pergamon (1995); and Comprehensive Organic Synthesis, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is Greene and Wuts, Protective Groups in Organic Synthesis, Wiley and Sons (1999).

Pharmacological Activity

Having regard to their modulation of CFTR activity, compounds of formula (I), in free or pharmaceutically acceptable salt form, hereinafter alternately referred to as "agents of the invention", are useful in the treatment of conditions which respond to the modulation of CFTR activity, particularly conditions benefiting from mucosal hydration such as cystic fibrosis.

Diseases mediated by modulation of CFTR activity, include diseases associated with the regulation of fluid volumes across epithelial membranes. For example, the volume of airway surface liquid is a key regulator of mucociliary clearance and the maintenance of lung health. The modulation of CFTR activity will promote fluid accumulation on the mucosal side of the airway epithelium thereby promoting mucus clearance and preventing the accumulation of mucus and sputum in respiratory tissues (including lung airways). Such diseases include respiratory diseases, such as cystic fibrosis, primary ciliary dyskinesia, chronic bronchitis, chronic obstructive pulmonary disease (COPD), asthma, respiratory tract infections (acute and chronic; viral and bacterial) and lung carcinoma. Diseases mediated by modulation of CFTR activity also include diseases other than respiratory diseases that are associated with abnormal fluid regulation across an epithelium, perhaps involving abnormal physiology of the protective surface liquids on their surface, e.g., Sjögren's Syndrome, xerostomia (dry mouth) or keratoconjunctivitis sire (dry eye). Furthermore, modulation of CFTR activity in the kidney could be used to promote diuresis and thereby induce a hypotensive effect.

Treatment in accordance with the invention may be symptomatic or prophylactic.

Asthma includes intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g., of acute asthmatic or bronchoconstrictor attack, improvements in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4-6 am, i.e., at a time normally substantially distant from any previously administered symptomatic asthma therapy.

Chronic obstructive pulmonary disease includes chronic bronchitis or dyspnea associated therewith, emphysema, as well as exacerbation of airways hyperreactivity consequent to other drug therapy, in particular, other inhaled drug therapy. The invention is also applicable to the treatment of bronchitis of whatever type or genesis including, e.g., acute, arachidic, catarrhal, croupus, chronic or phthinoid bronchitis.

Dry eye disease is characterized by a decrease in tear aqueous production and abnormal tear film lipid, protein and mucin profiles. There are many causes of dry eye, some of which include age, laser eye surgery, arthritis, medications, chemical/thermal burns, allergies and diseases, such as cystic fibrosis and Sjögren's Syndrome. Increasing anion secretion via CFTR would enhance fluid transport from the corneal endothelial cells and secretory glands surrounding the eye to increase corneal hydration. This would help to alleviate the symptoms associated with dry eye disease.

Sjögren's Syndrome is an autoimmune disease in which the immune system attacks moisture-producing glands throughout the body, including eye, mouth, skin, respiratory tissue, liver, vagina and gut. Symptoms include dry eye, dry mouth and dry vagina, as well as lung disease. The disease is also associated rheumatoid arthritis, systemic lupus, systemic sclerosis and polymypositis/dermatomyositis. Defective protein trafficking is believed to cause the disease, for which treatment options are limited. Modulators of CFTR activity may hydrate the various organs affected by the disease and help to alleviate the associated symptoms.

The suitability of CFTR activity modulators as a treatment of a disease benefiting from mucosal hydration may be tested by determining the movement of chloride ions in a suitable cell-based assay. For example single cells or confluent epithelia, endogenously expressing or engineered to overexpress CFTR can be used to assess channel function using electrophysiological techniques or ion flux studies. See methods described in: Hirsh et al., J Pharm Exp Ther (2004); Moody et al., Am J Physiol Cell Physiol (2005).

CFTR activity modulators, including the compounds of formula (I), are also useful as co-therapeutic agents for use in combination with other drug substances, such as anti-inflammatory, bronchodilatory, antihistamine or anti-tussive drug substances, particularly in the treatment of cystic fibrosis or obstructive or inflammatory airways diseases such as those mentioned hereinbefore, e.g., as potentiators of therapeutic activity of such drugs or as a means of reducing required dosaging or potential side effects of such drugs.

The compounds of Formula (I), (II) or (III) may be mixed with the other drug substance in a fixed pharmaceutical composition or it may be administered separately, before, simultaneously with or after the other drug substance.

Accordingly, the invention includes as a further aspect a combination of a CFTR activity modulator with osmotic agents (hypertonic saline, dextran, mannitol, Xylitol), ENaC blockers, an anti-inflammatory, bronchodilatory, antihistamine, anti-tussive, antibiotic and/or DNase drug substance, wherein the CFTR activity modulator and the further drug substance may be in the same or different pharmaceutical composition.

Suitable antibiotics include macrolide antibiotics, e.g., tobramycin (TOBI™).

Suitable DNase drug substances include dornase alfa (Pulmozyme™), a highly-purified solution of recombinant human deoxyribonuclease I (rhDNase), which selectively cleaves DNA. Dornase alfa is used to treat cystic fibrosis.

Other useful combinations of CFTR activity modulators with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl] tetrahydro-N,N-dimethyl-2H-pyran-4-amin-ium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, in particular, glucocorticosteroids, such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), Sel-CID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine A2B receptor antagonists such as those described in WO 02/42298; and beta-2 adrenoceptor agonists, such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula (I) of WO 0075114, which document is incorporated herein by reference, preferably compounds of the Examples thereof, especially indacaterol and pharmaceutically acceptable salts thereof, as well as compounds (in free or salt or solvate form) of formula (I) of WO 04/16601, and also compounds of EP 1440966, JP 05025045, WO 93/18007, WO 99/64035, USP 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618, WO 04/46083, WO 04/80964, WO 04/108765 and WO 04/108676.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285.

Suitable dual anti-inflammatory and bronchodilatory drugs include dual beta-2 adrenoceptor agonist/muscarinic antagonists such as those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

In accordance with the foregoing, the invention also provides as a further aspect a method for the treatment of a condition responsive to modulation of CFTR activity, e.g., diseases associated with the regulation of fluid volumes across epithelial membranes, particularly an obstructive airways disease, which comprises administering to a subject, particularly a human subject, in need thereof a compound of formula (I), (II) or (III), in free form or in the form of a pharmaceutically acceptable salt.

In another aspect the invention provides a compound of formula (I), (II) or (III), in free form or in the form of a pharmaceutically acceptable salt, for use in the manufacture of a medicament for the treatment of a condition responsive to modulation of CFTR activity, particularly an obstructive airways disease, e.g., cystic fibrosis and COPD.

The agents of the invention may be administered by any appropriate route, e.g. orally, e.g., in the form of a tablet or capsule; parenterally, e.g., intravenously; by inhalation, e.g., in the treatment of an obstructive airways disease; intranasally, e.g., in the treatment of allergic rhinitis; topically to the skin; or rectally. In a further aspect, the invention also provides a pharmaceutical composition comprising a compound of formula (I), in free form or in the form of a pharmaceutically acceptable salt, optionally together with a pharmaceutically acceptable diluent or carrier therefor. The composition may contain a co-therapeutic agent, such as an anti-inflammatory, broncho-dilatory, antihistamine or antitussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

When the composition comprises an aerosol formulation, it preferably contains, e.g., a hydro-fluoro-alkane (HFA) propellant, such as HFA134a or HFA227 or a mixture of these, and may contain one or more co-solvents known in the art, such as ethanol (up to 20% by weight), and/or one or more surfactants, such as oleic acid or sorbitan trioleate, and/or one or more bulking agents, such as lactose. When the composition comprises a dry powder formulation, it preferably contains, e.g., the compound of formula (I), (II) or (III) having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulised formulation, it preferably contains, e.g., the compound of formula (I), (II) or (III) either dissolved, or suspended, in a vehicle containing water, a co-solvent, such as ethanol or propylene glycol and a stabilizer, which may be a surfactant.

Further aspects of the invention include:

(a) a compound of formula (I), (II) or (III) in inhalable form, e.g., in an aerosol or other atomisable composition or in inhalable particulate, e.g., micronised form;

(b) an inhalable medicament comprising a compound of formula (I), (II) or (III) in inhalable form;

(c) a pharmaceutical product comprising a compound of formula (I) in inhalable form in association with an inhalation device; and (d) an inhalation device containing a compound of formula (I), (II) or (III) in inhalable form.

Dosages of compounds of formula (I), (II) or (III) employed in practicing the present invention will of course vary depending, e.g., on the particular condition to be treated, the effect desired and the mode of administration. In general, suitable daily dosages for administration by inhalation are of the order of 0.005-10 mg, while for oral administration suitable daily doses are of the order of 0.05-100 mg.

Pharmaceutical Use and Assay

Compounds of formula (I), (II) or (III) and their pharmaceutically acceptable salts, hereinafter referred to alternatively as "agents of the invention", are useful as pharmaceuticals. In particular, the compounds are suitable CFTR activity modulators and may be tested in the following assays.

Membrane Potential Assay

CFTR activity can be quantified by measuring the transmembrane potential. The means for measuring the transmembrane potential in a biological system can employ a number of methods including electrophysiological and optical fluorescence-based membrane potential assays.

The optical membrane potential assay utilises a negatively charged potentiometric dye, such as the FLIPR membrane potential dye (FMP) (see Baxter D F, Kirk M, Garcia A F, Raimondi A, Holmqvist M H, Flint K K, Bojanic D, Distefano P S, Curtis R, Xie Y. 'A novel membrane potential-sensitive fluorescent dye improves cell-based assays for ion channels.' J Biomol Screen. 2002 February; 7(1):79-85) which when extracellular is bound to a quenching agent. Upon cellular depolarisation the negatively charged dye redistributes to the intracellular compartment, unbinding from the membrane impermeant quench agent, yielding an increase in fluorescence. This change in fluorescence is proportional to the change in transmembrane potential which can result from the activity of CFTR. The changes in fluorescence can be monitored in real time by an appropriately equipped fluorescence detector such as the FLIPR (fluorometric imaging plate reader) in 96 or 384-well microtitre plates.

Cell Culture:

Chinese hamster ovary (CHO) cells stably expressing the ΔF508-CFTR channel were used for membrane potential experiments. Cells were maintained at 37° C. in 5% v/v $CO_2$ at 100% humidity in Modified Eagles medium (MEM) supplemented with 8% v/v foetal calf serum, 100 μg/ml methotrexate and 100 U/ml penicillin/streptomycin. Cells were grown in 225 $cm^2$ tissue culture flasks. For membrane potential assays cells were seeded into 96 well plates at 40,000 cells per well, allowed to adhere and then maintained at 26° C. for 48 h to facilitate channel insertion.

Potentiator Assay:

The membrane potential screening assay utilised a low chloride ion containing extracellular solution (~5 mM) combined with a double addition protocol. The first addition was of buffer with or without test compound followed 5 minutes later by an addition of forskolin (1-20 μM)—this protocol favours maximum chloride efflux in response to ΔF508-CFTR activation. The ΔF508-CFTR mediated chloride ion efflux leads to a membrane depolarisation which is optically monitored by the FMP dye.

Solutions:

Low chloride extracellular (mM): 120 Na-gluconate, 1.2 $CaCl_2$, 3.3 $KH_2PO_4$, 0.8 $K_2H$ $PO_4$, 1.2 $MgCl_2$, 10.0 D-glucose, 20.0 HEPES, pH 7.4 with NaOH FMP dye: made up as per manufacturers' instructions in low chloride extracellular solution detailed above, at 10× final concentration, and stored as 1 mL aliquots at −20° C.

Ion Works Quattro assay:

CFTR activity can also be quantified electrophysiologically using the whole-cell configuration of the patch clamp technique (Hamill et al Pflugers Archive 1981). This assay directly measures the currents associated with chloride flow through CFTR channels whilst either maintaining or adjusting the transmembrane voltage. This assay can use either single glass micropipettes or parallel planar arrays to measure CFTR activity from native or recombinant cell systems. Currents measured using parallel planar arrays can be quantified using an appropriately equipped instrument such as the Ion-Works Quattro (Molecular Devices) or the Qpatch (Sophion). The Quattro system can measure CFTR currents from either a single cell per recording well (HT configuration) or alternatively from a population of 64 cells per well (Population Patch Clamp PPC) (Finkel A, Wittel A, Yang N, Handran S, Hughes J, Costantin J. 'Population patch clamp improves data consistency and success rates in the measurement of ionic currents.' J Biomol Screen. 2006 August; 11(5):488-96).

Cell Culture:

Chinese hamster ovary (CHO) cells stably expressing the ΔF508-CFTR channel were used for IonWorks Quattro experiments. Cells were maintained at 37° C. in 5% v/v $CO_2$ at 100% humidity in D-MEM supplemented with 10% (v/v) FCS, 100 U/mL Penicillin/Streptomycin, 1% (v/v) NEAA, 1 mg/ml Zeocin and 500 ug/ml Hygromycin B. For experiments cells were grown in 225 $cm^2$ tissue culture flasks until near confluence and then cultured at 26° C. for 48-72 h to facilitate channel insertion. Cells were removed from the flask and resuspended in either extracellular recording solution for immediate experimentation or alternatively in growth medium supplemented with 10% v/v DMSO and frozen to −80° C. as 1-2 mL aliquots for use at a later date.

Potentiator Assay:

Cells, at a density of 1.5-3 million per mL, were placed on the Quattro system, added to the planar patch array and seals allowed to establish for 5-10 mins. After assessing seal resistances (commonly >50 MΩ), whole-cell access was obtained by perforation with 100 μg/mL amphotericin B. Baseline currents were measured by a pre-compound scan obtained by application of a voltage ramp from −100 to +100 mV. This was followed by addition of either buffer or test compound diluted in the extracellular solution supplemented with 20 μM forskolin, to each of the 384 wells of the planar parch array. After incubation step (5-20 minutes) the post-compound currents were measured again by application of a voltage ramp from −100 to +100 mV. The difference in currents between the pre- and post-compound scans defined the efficacy of CFTR potentiation.

Solutions:

Extracellular solution (ECS): 145 mM NaCl, 4 mM CsCl, 5 mM D-glucose, 10 mM TES, 1 mM $CaCl_2$, 1 mM $MgCl_2$, pH 7.4 NaOH Intracellular buffer (ICS): 113 mM L-Aspartic acid, 113 mM CsOH, 27 mM CsCl, 1 mM NaCl, 1 mM $MgCl_2$, 1 mM EGTA, 10 mM TES. pH 7.2 with CsOH. Filter sterilized before use.

Ion Transport Assay:

Another method to measure CFTR function is Ussings chamber short circuit current measurement. Engineered or native epithelial cells are grown to confluent monolayer on a semi-permeable filter and sandwiched between two perspex blocks. The flow of chloride ions via CFTR from one side of the epithelia to the other can be quantified by measuring the flow of current whilst maintaining the transepithelial potential at 0 mV. This is achieved using KCl filled agar-based electrodes to both clamp the cellular monolayer and measure the flow of currents.

Cell Culture:

FRT cells stably expressing ΔF508-CFTR were cultured on plastic in Coon's modified F-12 medium supplemented with 32 mM $NaHCO_3$, 10% v/v fetal bovine serum, 2 mM L-glutamine, 100 U/mL penicillin, 100 μg/mL streptomycin and 30 μg/mL hygromycin B as the growth medium. For Ussing chamber experiments, the cells were grown as polarized epithelia on Snapwell permeable support inserts (500000 cells/insert in growth medium) and cultured for 7 to 9 days. The inserts were fed with fresh Coon's modified F-12 growth medium every 48 hours, and 24 hours prior to Ussing chamber experiment. To increase the ΔF508 CFTR protein expression at the cell surface, plates were incubated at 27° C. for 48 h before performing an Ussing chamber experiment.

Potentiator Assay:

Fischer Rat Thyroid (FRT) epithelial cells, stably expressing human ΔF508-CFTR were used as monolayer cultures on permeable supports. $Cl^-$ current was measured using the short circuit current technique, under an imposed basolateral to apical $Cl^-$ gradient in Ussing chambers. To measure stable $Cl^-$ currents, FRT cells were cultured for 48 h at 27° C. to facilitate the insertion of ΔF508 CFTR into the plasma membrane. Ussing chamber studies were likewise conducted at 27° C. Under these conditions, the effects of cumulative additions of test compounds on ΔF508 CFTR currents could be quantitated with both potency and efficacy endpoints. Compounds were added to both the apical and basloalteral sides subsequent to addition of 10 μM forskolin. Efficacy of compounds was compared to a known potentiator such as gensitein.

Solutions:

Basolateral Ringer solution (mM): 126 NaCl, 24 $NaHCO_3$, 0.38 $KH_2PO_4$, 2.13 $K_2HPO_4$, 1 $MgSO_4$, 1 $CaCl_2$ and 10 glucose.

Apical Ringer solution (mM): 140 Na-gluconate, 1 $MgSO_4$, 2 $CaCl_2$, 1 HCl, 10 glucose and 24 $NaHCO_3$.

Compounds can also be tested for their ability to stimulate insertion of ΔF508 CFTR into the cell membrane using the above assays. For these assays the protocols were identical other than cells were not cultured at low temperature (26 or 27° C.) but instead incubated with test compounds for 12-24 h prior to assay.

Compounds of the Examples, herein below, generally have $EC_{50}$ values in the data measurements described above below 10 μM. Table 1 provides a list of representative compounds with their $EC_{50}$ value.

TABLE 1

| Example No | $EC_{50}$ μM |
|---|---|
| 2 | 0.015 |
| 3 | 0.055 |
| 4 | 0.076 |
| 5 | 0.05 |
| 6 | 0.426 |
| 7 | 0.040 |
| 8 | 0.060 |
| 9 | 0.090 |
| 10 | 0.112 |
| 11 | 0.037 |
| 12 | 0.035 |
| 14 | 0.115 |
| 15 | 0.051 |
| 16 | 0.008 |
| 17 | 0.010 |

Compounds listed below are within the scope of the broadest claim and the CFTR $EC_{50}$ values in the data measurements described above were above 5 μM:

3-amino-6-bromo-N-(imidazo[1,2-a]pyridin-2-ylmethyl)-5-(trifluoromethyl)pyrazine-2-carboxamide;

3-amino-6-bromo-N-((1-methyl-1H-imidazol-4-yl)methyl)-5-(trifluoromethyl)pyrazine-2-carboxamide;

2-(3-amino-6-bromo-5-(trifluoromethyl)picolinamido)acetic acid;

3-amino-6-bromo-N-((1-methyl-1H-pyrazol-3-yl)methyl)-5-(trifluoromethyl)pyrazine-2-carboxamide;

3-amino-N-(2-(4-fluorophenyl)-2-oxoethyl)-6-(1-methyl-1H-indol-6-yl)-5-(trifluoromethyl)picolinamide;

3-amino-6-bromo-N-((1-methyl-1H-imidazol-2-yl)methyl)-5-(trifluoromethyl)pyrazine-2-carboxamide;

6-((3H-[1,2,3]triazolo[4,5-b]pyridin-3-yl)oxy)-3-(2,5-dimethyl-1H-pyrrol-1-yl)-N-(3,3,3-trifluoro-2-hydroxy-2-methylpropyl)-5-(trifluoromethyl)picolinamide;

3-amino-6-(6-(3-(dimethylamino)propoxy)pyridin-3-yl)-N-(2-(4-fluorophenyl)-2-oxoethyl)-5-(trifluoromethyl)pyrazine-2-carboxamide;

(R)-3-amino-6-bromo-N-((4-methylpiperazin-2-yl)methyl)-5-(trifluoromethyl)pyrazine-2-carboxamide;

3-amino-6-bromo-N-((1-methyl-1H-imidazol-5-yl)methyl)-5-(trifluoromethyl)pyrazine-2-carboxamide;

3-amino-6-(3-(N,N-dimethylsulfamoyl)phenyl)-N-(2-(4-fluorophenyl)-2-oxoethyl)-5-(trifluoromethyl)picolinamide;

3-amino-6-bromo-N-isobutyl-N-methyl-5-(trifluoromethyl)pyrazine-2-carboxamide;

3-amino-6-bromo-N-((1-methyl-1H-pyrazol-5-yl)methyl)-5-(trifluoromethyl)pyrazine-2-carboxamide;

6-bromo-3-(methylamino)-N-(3,3,3-trifluoro-2-hydroxy-2-methylpropyl)-5-(trifluoromethyl)picolinamide;

(3-amino-6-bromo-5-(trifluoromethyl)pyrazin-2-yl)(4-methylpiperazin-1-yl)methanone;

3-amino-6-bromo-N-(2-(pyridin-4-yl)ethyl)-5-(trifluoromethyl)pyrazine-2-carboxamide;

3-amino-N-(2-(4-fluorophenyl)-2-oxoethyl)-6-(1-oxo-1,2,3,4-tetrahydroisoquinolin-6-yl)-5-(trifluoromethyl)picolinamide;

3-amino-6-(4-carbamoyl-2-methylphenyl)-N-(2-(4-fluorophenyl)-2-oxoethyl)-5-(trifluoromethyl)picolinamide;

3-amino-6-bromo-N-(2-(pyridin-3-yl)ethyl)-5-(trifluoromethyl)pyrazine-2-carboxamide;

3-amino-6-(3,4-dimethylphenyl)-N-(2-(4-fluorophenyl)-2-oxoethyl)-5-(trifluoromethyl)picolinamide;

3-amino-N-benzyl-6-bromo-N-methyl-5-(trifluoromethyl)pyrazine-2-carboxamide;

3-amino-6-hydroxy-N-(3,3,3-trifluoro-2-hydroxy-2-methylpropyl)-5-(trifluoromethyl)picolinamide;

3-amino-6-hydroxy-N-(3,3,3-trifluoro-2-hydroxy-2-methylpropyl)-5-(trifluoromethyl)picolinamide;

(3-amino-6-bromo-5-(trifluoromethyl)pyrazin-2-yl)(4-methyl-3-phenylpiperazin-1-yl)methanone;

(S)-3-amino-6-bromo-N-((1-ethylpyrrolidin-2-yl)methyl)-5-(trifluoromethyl)pyrazine-2-carboxamide; and 3-amino-6-bromo-N-(imidazo[1,5-a]pyridin-1-ylmethyl)-5-(trifluoromethyl)pyrazine-2-carboxamide.

The invention is illustrated by the following Examples.

EXAMPLES

General Conditions

Mass spectra were run on LC-MS systems using electrospray ionization. These were either Agilent 1100 HPLC/Micromass Platform Mass Spectrometer combinations or Waters Acquity HPLC with SQD Mass Spectrometer. $[M+H]^+$ refers to mono-isotopic molecular weights.

NMR spectra were run on open access Bruker AVANCE 400 NMR spectrometers using ICON-NMR. Spectra were measured at 298K and were referenced using the solvent peak.

Optical rotations were measured at 589 nm and 546 nm using an Optical activity AA-1000 polarimeter at 21° C.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, and NMR. Abbreviations used are those conventional in the art. If not defined, the terms have their generally accepted meanings.

ABBREVIATIONS app apparent
ATP adenosine 5'-triphosphate
BI NAP racemic 2,2'-bis(diphenylphosphino)-1,1'-binaphthyl
BOC tertiary butyl carboxy
br broad
d doublet
dd doublet of doublets
DCM dichloromethane
DIEA diethylisopropylamine
DIPEA diisopropylethylamine
DMF N,N-dimethylformamide
DMSO dimethylsulfoxide
DTT dithiothreitol
ESI electrospray ionization EtOAc ethyl acetate
eq equivalent
h hour(s)
HATU 2-(7-Aza-1H-benzotriazole-1-yl)-1,1,3,3-tetramethyluronium hexafluorophosphate
HPLC high pressure liquid chromatography
IR infrared spectroscopy
LCMS liquid chromatography and mass spectrometry
MeOH methanol
MS mass spectrometry
MW microwave
m multiplet
min minutes
ml milliliter(s)
m/z mass to charge ratio
NMR nuclear magnetic resonance
ppm parts per million
PS polymer supported
rac racemic
RT room temperature
Rt retention time
s singlet
SCX-2 strong cation exchange (e.g. Isolute® SCX-2 columns from Biotage)
t triplet
TEA triethylamine
TFA trifluoroacetic acid
THF tetrahydrofuran Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

If not indicated otherwise, the analytical HPLC conditions are as follows:

| Method 10 min LC_v001 | |
|---|---|
| Column | Waters BEH C18 100 × 2.1 mm, 1.7 μm |
| Column Temp. | 50° C. |
| Eluents | A: $H_2O$, B: acetonitrile, both containing 0.1% TFA |
| Flow Rate | 0.7 ml/min |
| Gradient | 0.25 min 5% B; 5% to 95% B in 7.75 min, 1.00 min 95% B |

| Method 10 min LC_v002 | |
|---|---|
| Column | Waters BEH C18 50 × 2.1 mm, 1.7 μm |
| Column Temperature | 50° C. |
| Eluents | A: $H_2O$, B: methanol, both containing 0.1% TFA |
| Flow Rate | 0.8 ml/min |
| Gradient | 0.20 min 5% B; 5% to 95% B in 7.80 min, 1.00 min 95% B |

-continued

| Method 10 min LC_v003 | |
|---|---|
| Column | Waters BEH C18 50 × 2.1 mm, 1.7 μm |
| Column Temperature | 50° C. |
| Eluents | A: $H_2O$, B: acetonitrile, both containing 0.1% TFA |
| Flow Rate | 0.8 ml/min |
| Gradient | 0.20 min 5% B; 5% to 95% B in 7.80 min, 1.00 min 95% B |

| Method 2 min LC_v001 | |
|---|---|
| Column | Waters BEH C18 100 × 2.1 mm, 1.7 μm |
| Column Temp. | 50° C. |
| Eluents | A: $H_2O$, B: acetonitrile, both containing 0.1% TFA |
| Flow Rate | 0.7 ml/min |
| Gradient | 0.25 min 5% B; 5% to 95% B in 1.00 min, 0.25 min 95% B |

| Method 2 min LC_v002 | |
|---|---|
| Column | Waters BEH C18 50 × 2.1 mm, 1.7 μm |
| Column Temperature | 50° C. |
| Eluents | A: $H_2O$, B: methanol, both containing 0.1% TFA |
| Flow Rate | 0.8 ml/min |
| Gradient | 0.20 min 5% B; 5% to 95% B in 1.30 min, 0.25 min 95% B |

| Method 2 min LC_v003 | |
|---|---|
| Column | Waters BEH C18 50 × 2.1 mm, 1.7 μm |
| Column Temperature | 50° C. |
| Eluents | A: $H_2O$, B: acetonitrile, both containing 0.1% TFA |
| Flow Rate | 0.8 ml/min |
| Gradient | 0.20 min 5% B; 5% to 95% B in 1.30 min, 0.25 min 95% B |

| Method 10 min C18 | |
|---|---|
| Column: | Gemini C18 100 × 3 mm, 3 micron |
| Column Temperature | 50° C. |
| Eluents: | A: H2O, B: Methanol, 0.1% formic acid |
| Flow rate: | 1 ml/min |
| Gradient: | 0.00 min 0% B, 10.00 min 95% B |

| Method AD25IPA_DEA | |
|---|---|
| Mobile Phase: | 25% isopropanol + 0.1% v/v DEA/75% $CO_2$ |
| Column: | Chiralpak AD-H, 250 × 10 mm id, 5 μm |
| Detection: | UV @ 220 nm |
| Flow rate: | 10 ml/min |

Example compounds of the present invention include

Preparation of Final Compounds

Example 1.0

3-Amino-6-bromo-5-trifluoromethyl-pyridine-2-carboxylic acid (3,3,3-trifluoro-2-hydroxy-2-methyl-propyl)-amide

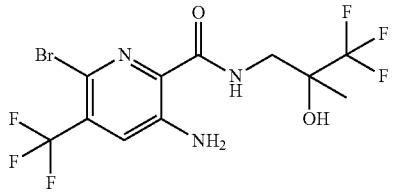

3-Amino-6-bromo-5-trifluoromethyl-pyridine-2-carboxylic acid (Intermediate A) (397 mg, 1.392 mmol), 3-amino-1,1,1-trifluoro-2-methyl-propan-2-ol hydrochloride (250 mg, 1.392 mmol) and HATU (529 mg, 1.392 mmol) were dissolved in DMF (10 ml) and stirred at RT for 2 min. 4-Methylmorpholine (0.413 ml, 4.18 mmol) was added and stirring continued at RT for 3 h. The reaction mixture was poured onto ice/water (100 ml) and extracted with EtOAc (250 ml). The organic extract was washed with sat $NH_4Cl$ solution (~50 ml), dried over $MgSO_4$ and concentrated in vacuo to give a pale brown oil. The oil was dissolved in $CHCl_3$ (~3 ml) and loaded onto a 24 g ISCO (silica) column eluting with iso-hexane:EtOAc to afford the title product; LC-MS Rt=1.46 mins; $[M+H]^+$ 410.1, Method 2 min-LC_v002. $^1H$ NMR (400 MHz, DMSO-d6) δ 8.30 (NH, t), 7.72 (1H, s), 7.29 (NH2, b s), 6.28 (OH, s), 3.68 (1H, dd), 3.47 (1H, dd), 1.24 (3H, s). $^{19}F$ NMR (400 MHz, DMSO-d6) δ −62.71 (CF3, s), −80.48 (CF3, s).

The compounds of the following tabulated Examples (Table 2) were prepared by a similar method to that of Example 1 from the appropriate starting compound and amine. Single enantiomers were prepared by using chiral amines or by separation of the product by Supercritical Fluid Chromatography. The preparations of the starting compounds and amines are described in the Intermediates section, unless they are commercially available. DIPEA or TEA may have been used in place of 4-methylmorpholine in some reactions.

TABLE 2

| Ex. | Structure | Name | Retention Time, $[M + H]^+$, 1H NMR |
|---|---|---|---|
| 1.1 | 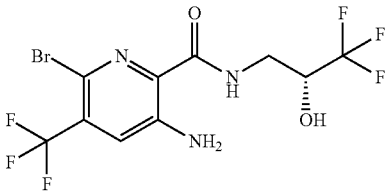 | 3-Amino-6-bromo-5-trifluoromethyl-pyridine-2-carboxylic acid ((R)-3,3,3-trifluoro-2-hydroxy-propyl)-amide (Separated by SFC, second eluted peak) | R.t 3.26 mins; Method = AD25IPA_DEA 1H NMR (DMSO) δ 3.4 (1H, m), 3.6 (1H, m), 4.3 (1H, m), 6.5 (1H, s), 7.3 (2H, s), 7.7 (1H, s), 8.6 (1H, t), |
| 1.2 | 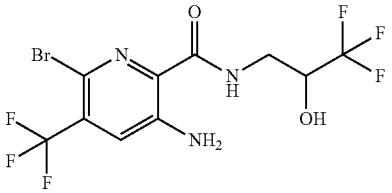 | 3-Amino-6-bromo-5-trifluoromethyl-pyridine-2-carboxylic acid (3,3,3-trifluoro-2-hydroxy-propyl)-amide (Racemate) | Rt 1.42 mins; $[M + H]^+$ 398 Method: 2minLC_v002 1H NMR (DMSO) δ 3.4 (1H, m), 3.6 (1H, m), 4.3 (1H, m), 6.5 (1H, d), 7.3 (2H, s), 7.7 (1H, s), 8.6 (1H, t), |
| 1.3 | 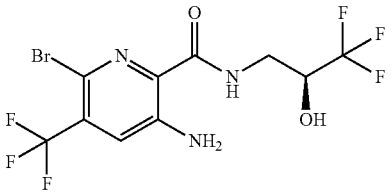 | 3-Amino-6-bromo-5-trifluoromethyl-pyridine-2-carboxylic acid ((S)-3,3,3-trifluoro-2-hydroxy-propyl)-amide Prepared using (S)-3-Amino-1,1,1-trifluoro-propan-2-ol | Rt 1.41 mins; $[M + H]^+$ 398 Method: 2minLC_v002 1H NMR (DMSO) δ 3.4 (1H, m), 3.6 (1H, m), 4.3 (1H, m), 6.5 (1H, d), 7.3, (2H, s), 7.7 (1H, s), 8.6 (1H, t) |
| 1.4 | 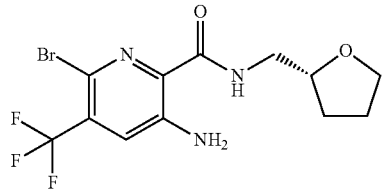 | 3-Amino-6-bromo-5-trifluoromethyl-pyridine-2-carboxylic acid [(R)-1-(tetrahydro-furan-2-yl)methyl]-amide Prepared using (R)-(−)-tetrahydrofurfuryl amine | Rt 1.51 mins; $[M + H]^+$ 370 Method: 2minLC_v002 1H NMR (DMSO) δ 1.6 (1H, m), 1.9, (3H, m), 3.4, (2H, m), 3.7, (1H, m), 3.8, (1H, m), 4.1, (1H, m), 7.3, (2H, s), 7.7, (1H, s), 8.4, (1H, t) |
| 1.5 | 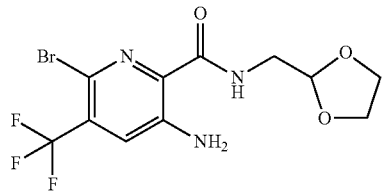 | 3-Amino-6-bromo-5-trifluoromethyl-pyridine-2-carboxylic acid ([1,3]dioxolan-2-ylmethyl)-amide | Rt 1.42 mins; $[M + H]^+$ 370 Method: 2minLC_v002 1H NMR (DMSO) δ 3.4, (2H, t), 3.8, (2H, m), 3.9, (2H, m), 5.0, (1H, t), 7.3, (2H, br), 7.7, (1H, s), 8.4, (1H, t), |
| 1.6 | 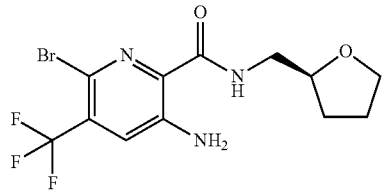 | 3-Amino-6-bromo-5-trifluoromethyl-pyridine-2-carboxylic acid [(S)-1-(tetrahydro-furan-2-yl)methyl]-amide Prepared using (S)-(+)-Tetrahydrofurfurylamine | Rt 1.52 mins; $[M + H]^+$ 370 Method: 2minLC_v002. 1H NMR (DMSO) 1.6, (1H, m), 1.9, (3H, m), 3.3, (2H, m), 3.6, (1H, m), 3.8, (1H, m), 4.0, (1H, m), 7.4, (2H, s), 7.7, (1H, s), 8.4, (1H, d) |

TABLE 2-continued

| Ex. | Structure | Name | Retention Time, [M + H]$^+$, 1H NMR |
|---|---|---|---|
| 1.7 | 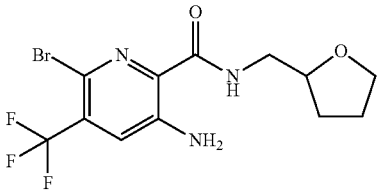 | 3-Amino-6-bromo-5-trifluoromethyl-pyridine-2-carboxylic acid (tetrahydro-furan-2-ylmethyl)-amide | Rt 1.49 mins; [M + H]$^+$ 368 Method: 2minLC_v002. 1H NMR (DMSO) δ 1.55, (1H, m), 1.8, (3H, m), 3.3, (2H, m), 3.6, (1H, m), 3.8, (1H, m), 4.0, (1H, m), 7.3, (2H, s), 7.7, (1H, s), 8.4, (1H, t) |
| 1.8 | 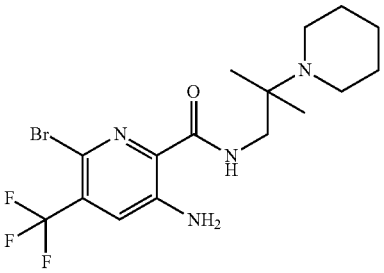 | 3-Amino-6-bromo-5-trifluoromethyl-pyridine-2-carboxylic acid (2-methyl-2-piperidin-1-yl-propyl)-amide | Rt 1.14 mins; [M + H]$^+$ 423 Method: 2minLC_v002 1H NMR (DMSO) δ 1.3, (6H, s), 1.4, (1H, m), 1.7, (3H, m), 1.9, (2H, m), 2.9, (2H, m), 3.6, (2H, m), 3.7, (2H, m), 7.3, (2H, s), 7.7, (1H, s), 8.7, (1H, t) |
| 1.9 | 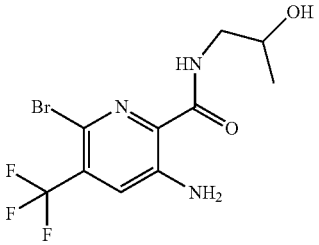 | 3-Amino-6-bromo-5-trifluoromethyl-pyridine-2-carboxylic acid (2-hydroxy-propyl)-amide | Rt 4.06 mins; [M + H]$^+$ 344. Method: 10minLC_v002 1H NMR. ([400 MHz], [DMSO-d6]) δ 8.30 (1H, t), 7.69 (1H, s), 7.28 (2H, br s), 4.84 (1H, d), 3.78 (1H, m), 3.29 (1H, m), 3.14 (1H, m), 1.05 (3H, d). |
| 1.10 | 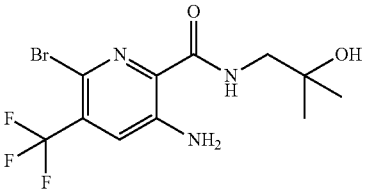 | 3-Amino-6-bromo-5-trifluoromethyl-pyridine-2-carboxylic acid (2-hydroxy-2-methyl-propyl)-amide | Rt 4.35 mins; [M + H]$^+$ 338. Method: 10minLC_v002 1H NMR. ([400 MHz], [DMSO-d6]) δ 8.14 (1H, t), 7.70 (1H, s), 7.29 (2H, br s), 4.70 (1H, s), 3.24 (1H, d), 1.10 (6H, s). |
| 1.11 | 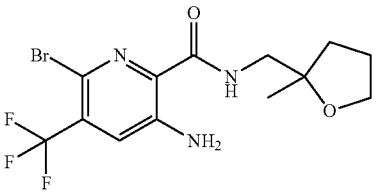 | 3-Amino-6-bromo-5-trifluoromethyl-pyridine-2-carboxylic acid (2-methyl-tetrahydro-furan-2-ylmethyl)-amide | Rt 1.53 mins; [M + H]$^+$ 384 Method: 2minLC_v002. 1H NMR. ([400 MHz], [DMSO-d6]) δ 8.12 (1H, t), 7.70 (1H, s), 7.28 (2H, br s), 3.76 (2H, t), 3.33 (2H, d), 1.88 (2H, m), 1.80 (1H, m), 1.60 (1H, m), 1.13 (3H, s). |
| 1.12 | 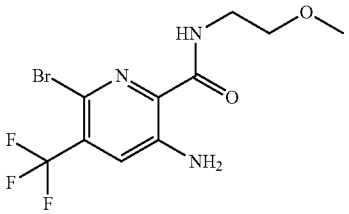 | 3-Amino-6-bromo-5-trifluoromethyl-pyridine-2-carboxylic acid (2-methoxy-ethyl)-amide | Rt 1.43 mins; [M + H]$^+$ 342; Method: 2minLC_v002. 1H NMR. ([400 MHz], [DMSO-d6]) δ 8.41 (1H, t), 7.69 (1H, s), 7.28 (2H, br s), 3.44 (4H, m), 3.27 (3H, s). |
| 1.13 | 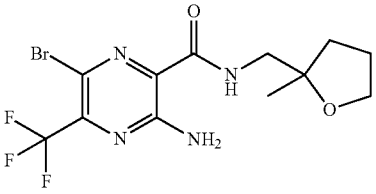 | 3-Amino-6-bromo-5-trifluoromethyl-pyrazine-2-carboxylic acid (2-methyl-tetrahydro-furan-2-ylmethyl)-amide | Rt 1.52 mins; [M + H]$^+$ 385; Method: 2minLC_v002. 1H NMR. ([400 MHz], [DMSO-d6]) δ 8.35 (1H, t), 8.09 (2H, br s), 3.76 (2H, t), 3.34 (2H, d), 1.86 (3H, m), 1.58 (1H, m), 1.13 (3H, s). |

TABLE 2-continued

| Ex. | Structure | Name | Retention Time, [M + H]$^+$, 1H NMR |
|---|---|---|---|
| 1.14 | 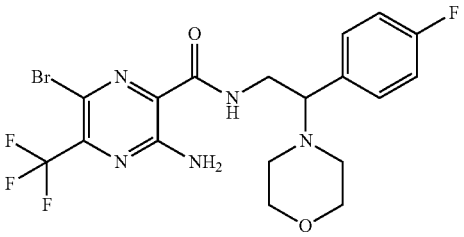 | 3-Amino-6-bromo-5-trifluoromethyl-pyrazine-2-carboxylic acid [2-(4-fluoro-phenyl)-2-morpholin-4-yl-ethyl]-amide | Rt 4.29 mins; [M + H]$^+$ 492. Method: 10minLC_v002. $^1$H NMR (400 MHz, MeOD) $\delta_H$ 7.61-7.64 (2H, m, 2 × Ar'H (AA'BB'X system)), 7.28-7.32 (2H, m, 2 × Ar'H (AA'BB'X system)), 4.65-4.73 (1H, br m, NHCH$_A$H$_B$CH$_X$N (Ar')), 4.31 (1H, dd$_{ABX}$, J = 6.5/14.4 Hz, NHCH$_A$H$_B$CH$_X$N(Ar')), 3.70-4.14 (6H, m, NHCH$_A$H$_B$CH$_X$N (Ar') + 5 × morpholine CH), 3.00-3.30 (3H, m, 3 × morpholine CH). |
| 1.15 | 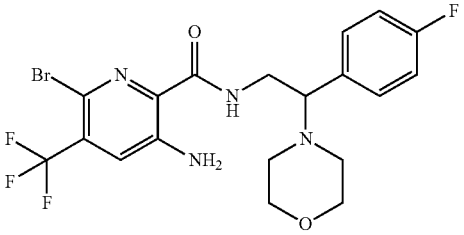 | 3-Amino-6-bromo-5-trifluoromethyl-pyridine-2-carboxylic acid [2-(4-fluoro-phenyl)-2-morpholin-4-yl-ethyl]-amide | Rt 4.39 mins; [M + H]$^+$ 491 Method: 10minLC_v002. $^1$H NMR (400 MHz, MeOD) $\delta_H$ 8.37-8.38 (1H, m, ArC(O)NHCH$_2$), 7.68 (1H, s, ArH-1), 7.35 (2H, m (AA'BB'X system), 2 × Ar'H-2), 7.17-7.25 (4H, br s + m (AA'BB'X system), ArNH$_2$ + 2 × Ar'H-3), 3.73-3.81 (2H, m, NHCH$_A$H$_B$CH(N)Ar' + NHCH$_A$H$_B$CH(N)Ar'), 3.53-3.58 (5H, morpholine 2 × CH$_2$ + NHCH$_A$H$_B$CH(N)Ar'), 2.34-2.43 (4H, m, 2 × morpholine CH$_2$). |
| 1.16 | 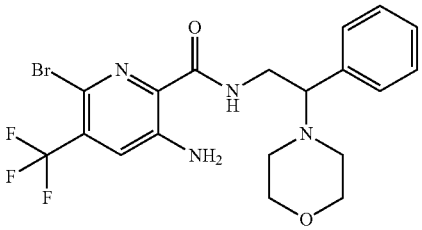 | 3-Amino-6-bromo-5-trifluoromethyl-pyridine-2-carboxylic acid (2-morpholin-4-yl-2-phenyl-ethyl)-amide | Rt 4.20 mins; [M + H]$^+$ 473 Method 10minLC_v002. 1H NMR (400 MHz, DMSO-d6) δ 8.46 (1H, s broad), 7.70 (1H, s), 7.32 (7H, m broad), 3.75 (2H, m broad), 3.59 (4H, broad), 2.40 (2H, broad), 2.30 (2H, broad). |
| 1.17 | 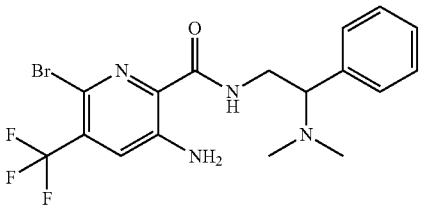 | 3-Amino-6-bromo-5-trifluoromethyl-pyridine-2-carboxylic acid (2-dimethylamino-2-phenyl-ethyl)-amide | Rt 4.25 mins; [M + H]$^+$ 431; Method; 10minLC_v002. 1H NMR (400 MHz, DMSO-d6) δ 10.20 (1H, s), 8.72 (1H, t), 7.71 (1H, s), 7.60 (2H, s broad), 7.50 (3H, s broad) 7.30 (2H, s broad), 4.67 (1H, m), 4.19 (1H, qui), 3.83 (m), 2.80 (3H, d), 2.61 (3H, d). |
| 1.18 | 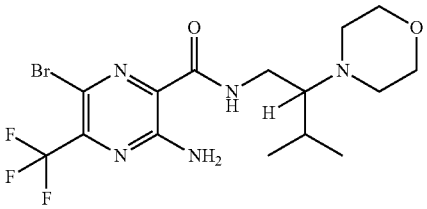 | 3-Amino-6-bromo-5-trifluoromethyl-pyrazine-2-carboxylic acid (3-methyl-2-morpholin-4-yl-butyl)-amide | Rt 3.39 mins; [M + H]$^+$ 442. Method 10minLC_v002. 1H NMR (400 MHz, DMSO-d6) δ 9.03 (1H, s), 9.10 (1H, s), 8.12 (2H, s), 4.00-3.20 (12H, broad), 1.10 (3H, broad), 1.00 (3H, broad). |
| 1.19 | 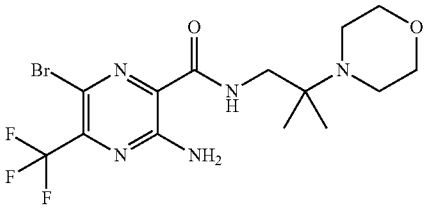 | 3-Amino-6-bromo-5-trifluoromethyl-pyrazine-2-carboxylic acid (2-methyl-2-morpholin-4-yl-propyl)-amide | Rt 2.83 mins; [M + H]$^+$ 428; Method 10minLC_v002. 1H NMR (400 MHz, DMSO-d6) δ 9.04 (1H, s), 8.95 (1H, s), 8.10 (2H, s), 4.04 (2H, d), 3.75 (2H, t), 3.60 (4H + broad water signal underneath), 3.20 (2H, q), 1.35 (6H, s). |

TABLE 2-continued

| Ex. | Structure | Name | Retention Time, [M + H]$^+$, 1H NMR |
|---|---|---|---|
| 1.20 | 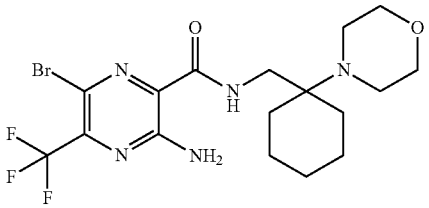 | 3-Amino-6-bromo-5-trifluoromethyl-pyrazine-2-carboxylic acid (1-morpholin-4-yl-cyclohexylmethyl)-amide | Rt 3.59 mins; [M + H]$^+$ 466. Method 10minLC_v002. 1H NMR (400 MHz, DMSO-d6) δ 9.00 (1H, broad), 8.90 (1H, broad), 8.10 (1H, s), 4.02-3.35 (20H, very broad) |
| 1.21 | 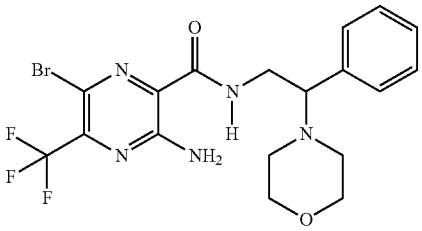 | 3-Amino-6-bromo-5-trifluoromethyl-pyrazine-2-carboxylic acid (2-morpholin-4-yl-2-phenyl-ethyl)-amide | Rt 6.09 mins; [M + H]$^+$ 474 Method 10minC18 |
| 1.22 | 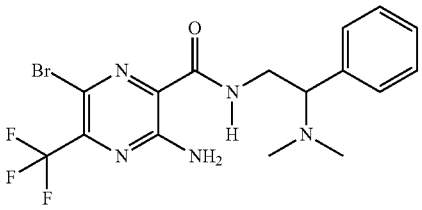 | 3-Amino-6-bromo-5-trifluoromethyl-pyrazine-2-carboxylic acid (2-dimethylamino-2-phenyl-ethyl)-amide | Rt 5.42 mins; [M + H]$^+$ 432 Method 10minC18 |
| 1.23 | 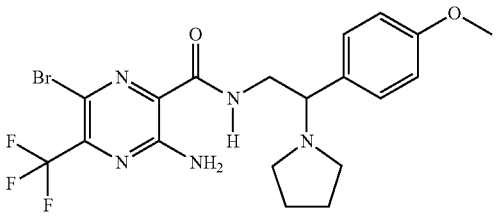 | 3-Amino-6-bromo-5-trifluoromethyl-pyrazine-2-carboxylic acid [2-(4-methoxy-phenyl)-2-pyrrolidin-1-yl-ethyl]-amide | Rt 5.64 mins; [M + H]$^+$ 488 Method 10minC18 |
| 1.24 | 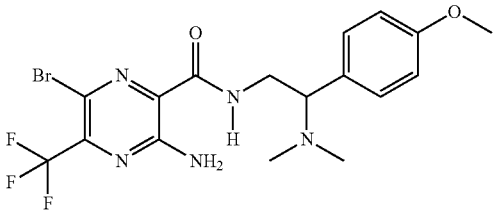 | 3-Amino-6-bromo-5-trifluoromethyl-pyrazine-2-carboxylic acid [2-dimethylamino-2-(4-methoxy-phenyl)-ethyl]-amide | Rt 5.51 mins; [M + H]$^+$ 462; Method 10minC18 |
| 1.25 | 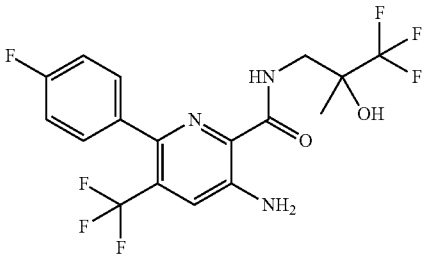 | 3-Amino-6-(4-fluoro-phenyl)-5-trifluoromethyl-pyridine-2-carboxylic acid (3,3,3-trifluoro-2-hydroxy-2-methyl-propyl)-amide | Rt 5.41 mins; [M + H]$^+$ 426; Method 10minLC_v002. $^1$H NMR δ 8.42 (1H, m), 7.72 (1H, s), 7.5 (2H, m), 7.3 (2H, t), 7.22 (2H, br s), 6.24 (1H, s), 3.68 (1H, m), 3.46 (1H, m), 1.24 (3H, s) |
| 1.26 | 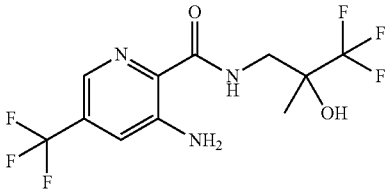 | 3-Amino-5-trifluoromethyl-pyridine-2-carboxylic acid (3,3,3-trifluoro-2-hydroxy-2-methyl-propyl)-amide | Rt 4.18 mins; [M + H]$^+$ 332; Method 10minLC_v002. $^1$H NMR δ 8.58 (1H, t), 8.1 (1H, s), 7.56 (1H, s), 7.2 (2H, br s), 6.29 (1H, s), 3.61-3.7 (1H, m), 3.42-3.5 (1H, m), 1.26 (3H, s). |

TABLE 2-continued

| Ex. | Structure | Name | Retention Time, [M + H]$^+$, 1H NMR |
|---|---|---|---|
| 1.27 | 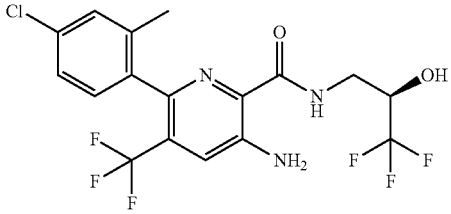 | 3-Amino-6-(4-chloro-2-methyl-phenyl)-5-trifluoromethyl-pyridine-2-carboxylic acid ((R)-3,3,3-trifluoro-2-hydroxy-propyl)-amide Prepared using (R)-3-amino-1,1,1-trifluoropropan-2-ol | Rt 1.59 mins; [M + H]$^+$ 442 Method: 2minLC_v002. 1H NMR. ([400 MHz], [DMSO-d6]) δ 8.54 (1H, br), 7.69 (1H, s), 7.41 (1H, d), 7.30 (1H, dd), 7.24 (2H, br s), 7.20 (1H, d), 6.40 (1H, br), 4.19 (1H, m), 3.54 (1H, m), 3.36 (1H, m), 2.01 (3H, s). |
| 1.28 | 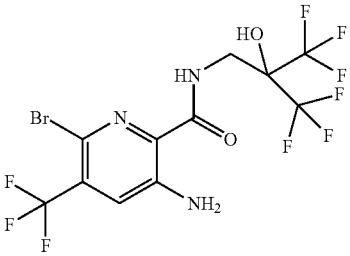 | 3-Amino-6-bromo-5-trifluoromethyl-pyridine-2-carboxylic acid (3,3,3-trifluoro-2-hydroxy-2-trifluoromethyl-propyl)-amide | Rt 1.59 mins; [M + H]$^+$ 466; Method 2minLC_v002. $^1$H NMR (400 MHz, DMSO-d6) δ 8.50 (1H, t), 8.30 (1H, s), 7.72 (1H, s), 7.30 (2H, s), 4.00 (2H, d) |
| 1.29 | 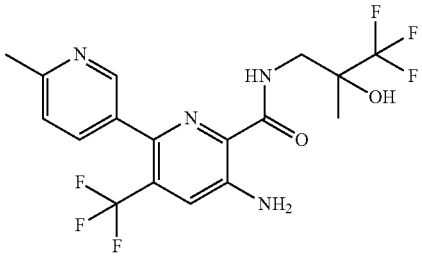 | 5-Amino-6'-methyl-3-trifluoromethyl-[2,3']bipyridinyl-6-carboxylic acid (3,3,3-trifluoro-2-hydroxy-2-methyl-propyl)-amide | Rt 1.16 mins; [M + H]$^+$ 423; Method 2minLC_v002. $^1$H NMR (400 MHz, DMSO-d6) δ 8.53 (1H, d), 8.45 (1H, t), 7.75 (1H, d), 7.71 (1H, s), 7.34 (1H, d), 7.25 (2H, s), 6.21 (1H, s), 3.69 (1H, dd), 3.42 (1H, dd), 2.54 (3H, s), 1.22 (3H, s). |
| 1.30 | 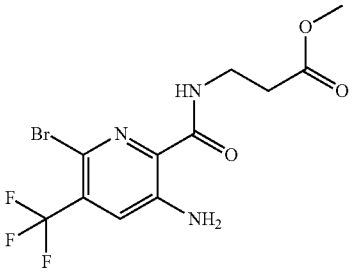 | Methyl 3-(3-amino-6-bromo-5-(trifluoromethyl) picolinamido)propanoate. | Rt 4.64 mins; [M + H]$^+$ 372.1; Method 10minLC_v002. $^1$H NMR (400 MHz, DMSO-d6) δ 8.56 (1H, t), 7.68 (1H, s), 7.27 (2H, br s), 3.61 (3H, s) 3.50 (2H, q), 2.60 (2H, t). |
| 1.31 | 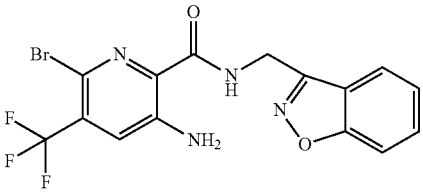 | 3-Amino-N-(benzo[d]isoxazol-3-ylmethyl)-6-bromo-5-(trifluoromethyl) picolinamide | Rt 4.18 mins; [M + H]$^+$ 417.1; Method 10minLC_v002. $^1$H NMR (400 MHz, DMSO-d6) δ 9.32 (NH, t), 7.96 (1H, dt), 7.74 (1H, dt), 7.70 (1H, s), 7.65-7.62 (1H, m), 7.40-7.36 (1H, m), 7.29 (NH2, b s), 4.88 (2H, d) |
| 1.32 | 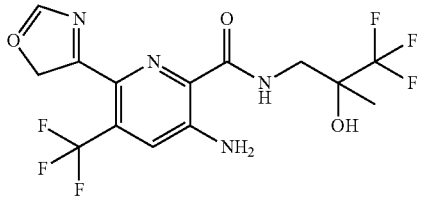 | 3-Amino-6-(oxazol-2-yl)-N-(3,3,3-trifluoro-2-hydroxy-2-methylpropyl)-5-(trifluoromethyl) picolinamide | Rt 3.44 mins; [M + H]$^+$ 399.1; Method 10minLC_v003. |

TABLE 2-continued

| Ex. | Structure | Name | Retention Time, [M + H]+, 1H NMR |
|---|---|---|---|
| 1.33 | 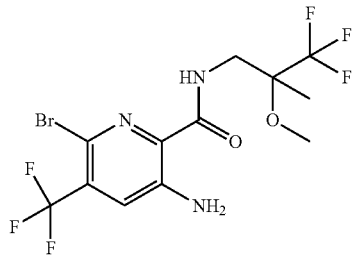 | Single enantiomer of 3-Amino-6-bromo-N-(3,3,3-trifluoro-2-methoxy-2-methylpropyl)-5-(trifluoromethyl) picolinamide (Separated by SFC, second eluted peak) | 1H NMR (400 MHz, DMSO-d6) δ 8.24 (1H, t), 7.72 (1H, s), 7.29 (2H, s), 3.65 (2H, m), 3.37 (3H, s), 1.35 (3H, s) |
| 1.34 | 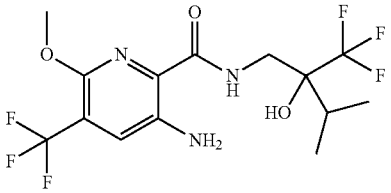 | Single enantiomer of 3-amino-N-(2-hydroxy-3-methyl-2-(trifluoromethyl)butyl)-6-methoxy-5-(trifluoromethyl) picolinamide (Separated by SFC, first eluted peak) | Rt 4.48 mins; [M + H]+ 390.3; Method 10minLC_v003. 1H NMR (400 MHz, DMSO-d6) δ 8.21 (1H, m), 7.69 (1H, s), 6.59 (2H, s), 6.26 (1H, s), 3.91 (3H, s), 3.68 (2H, m), 2.02 (1H, m), 1.02 (6H, m) |
| 1.35 | 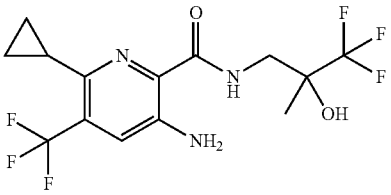 | 3-Amino-6-cyclopropyl-N-(3,3,3-trifluoro-2-hydroxy-2-methylpropyl)-5-(trifluoromethyl) picolinamide | Rt 1.23 mins; [M + H]+ 372.2; Method 2minLC_v003. 1H NMR (400 MHz, DMSO-d6) δ 8.29 (1H, m), 7.56 (1H, s), 6.9 (2H, br s), 6.3 (1H, s), 3.62 (1H, m), 3.48 (1H, m), 2.1 (1H, m), 1.24 (3H, s), 0.9-1.1 (4H, m) |
| 1.36 | 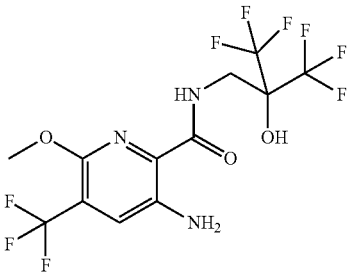 | 3-Amino-6-methoxy-N-(3,3,3-trifluoro-2-hydroxy-2-(trifluoromethyl)propyl)-5-(trifluoro methyl) picolinamide | Rt 4.27 mins; [M + H]+ 416.3; Method 10minLC_v003. 1H NMR (400 MHz, DMSO-d6) δ 8.39 (1H, t), 8.32 (1H, br s), 7.69 (1H, s), 6.70 (2H, br s), 3.99 (2H, d), 3.93 (3H, s), |
| 1.37 | 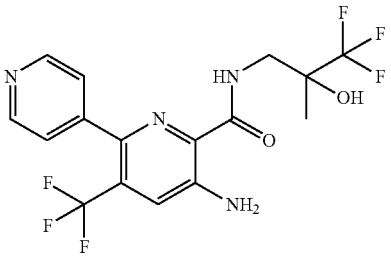 | Single enantiomer of 5-amino-N-(3,3,3-trifluoro-2-hydroxy-2-methylpropyl)-3-(trifluoromethyl)-2,4'-bipyridine-6-carboxamide (Separated by SFC, first eluted peak) | Rt 0.86 mins; [M + H]+ 409.1; Method 2minLC_v003. 1H NMR (400 MHz, DMSO-d6) δ 8.70 (2H, d), 8.45 (1H, t), 7.75 (1H, s), 7.50 (2H, d), 7.33 (2H, s), 6.22 (1H, s), 3.69 (1H, dd), 3.43 (1H, dd), 1.21 (3H, s). |
| 1.38 | 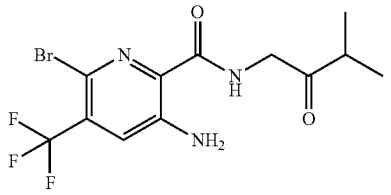 | 3-Amino-6-bromo-5-trifluoromethyl-pyridine-2-carboxylic acid (3-methyl-2-oxo-butyl)-amide | Rt 1.18 mins; [M + H]+ 368; Method 2minLC_v003. 1H NMR (400 MHz, DMSO-d6) δ 8.64 (1H, t), 7.71 (1H, s), 7.29 (2H, broad s), 4.2 (2H, d), 2.7-2.8 (1H, m), 1.08 (6H, d, 2 × CH3). |

TABLE 2-continued

| Ex. | Structure | Name | Retention Time, [M + H]+, 1H NMR |
|---|---|---|---|
| 1.39 | 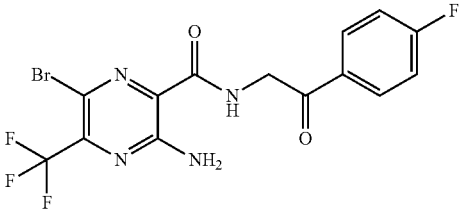 | 3-Amino-6-bromo-5-trifluoromethyl-pyrazine-2-carboxylic acid [2-(4-fluoro-phenyl)-2-oxo-ethyl]-amide | $^{1}$H NMR (400 MHz, DMSO-d6) δ 9.0 (1H, t, NH), 8.1 (4H, m, NH2, Ar—H), 7.4 (2H, t, Ar—H), 4.8 (2H, 5, CH2) |

Example 2 and 3

These compounds namely, 3-Amino-6-bromo-5-trifluoromethyl-pyridine-2-carboxylic acid ((R)-3,3,3-trifluoro-2-hydroxy-2-methyl-propyl)-amide. (Ex. 2)

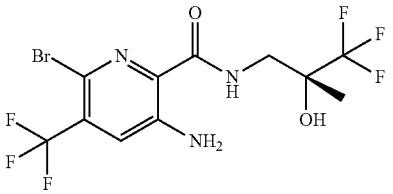

and 3-Amino-6-bromo-5-trifluoromethyl-pyridine-2-carboxylic acid ((S)-3,3,3-trifluoro-2-hydroxy-2-methyl-propyl)-amide. (Ex. 3)

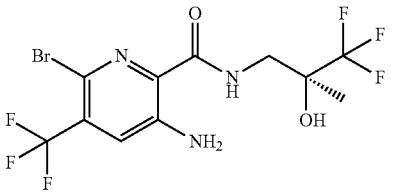

are prepared by chiral separation of 3-amino-6-bromo-5-trifluoromethyl-pyridine-2-carboxylic acid (3,3,3-trifluoro-2-hydroxy-2-methyl-propyl)-amide. (Example 1) using Supercritical Fluid Chromatography under the following conditions:

Mobile Phase: 12% isopropanol+0.1% DEA/88% $CO_2$

Column: Chiralpak OJ-H, 250×10 mm id, 5 μm

Detection: UV@220 nm

Flow rate: 10 ml/min

Sample concentration: 347 mg in 5 ml EtOH.

Injection volume: 50 μl

Example 2

First eluted peak: 3-Amino-6-bromo-5-trifluoromethyl-pyridine-2-carboxylic acid ((R)-3,3,3-trifluoro-2-hydroxy-2-methyl-propyl)-amide.

LC-MS: Rt=4.97 min [M+H]+ 410.1/412.2 (Method 10 minLC_v002).

1H NMR (400 MHz, DMSO-d6) δ 8.30 (NH, t), 7.72 (1H, s), 7.29 (NH2, b s), 6.28 (OH, s), 3.68 (1H, dd), 3.47 (1H, dd), 1.24 (3H, s)

$^{19}$F NMR (400 MHz, DMSO-d6) d −62.70 ($CF_3$, s), −80.47 (CF3, s)

Optical rotation $[\alpha]^{21}{}_{D}$ at 589 nm+14.4° (c=0.522, MeOH).

Example 3

Second eluted peak: 3-Amino-6-bromo-5-trifluoromethyl-pyridine-2-carboxylic acid ((S)-3,3,3-trifluoro-2-hydroxy-2-methyl-propyl)-amide.

LC-MS Rt=4.94 min [M+H]+ 412.1 (Method 10 minLC_v002).

1H NMR (400 MHz, DMSO-d6) δ 8.30 (NH, t), 7.72 (1H, s), 7.29 (NH2, b s), 6.28 (OH, s), 3.68 (1H, dd), 3.47 (1H, dd), 1.24 (3H, s)

$^{19}$F NMR (400 MHz, DMSO-d6) d −62.70 ($CF_3$, s), −80.48 ($CF_3$, s).

The stereochemistry of this compound was confirmed by X-ray crystallography.

Example 4, 5 and 6

This compound namely, 3-Amino-6-methoxy-5-trifluoromethyl-pyridine-2-carboxylic acid (3,3,3-trifluoro-2-hydroxy-2-methyl-propyl)-amide. (Ex. 4),

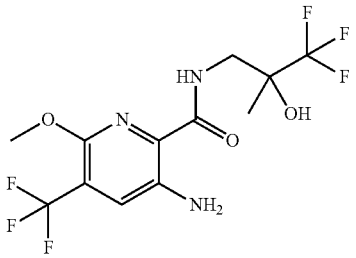

was prepared according to the following procedure:

A solution comprising 3-amino-6-methoxy-5-trifluoromethyl-pyridine-2-carboxylic acid (Intermediate D)(4 g, 16.94 mmol) and 3-amino-1,1,1-trifluoro-2-methylpropan-2-ol hydrochloride (Intermediate R) (3.04 g, 16.94 mmol) in NMP (188 ml) was treated with HATU (7.73 g, 20.33 mmol) followed by dropwise addition (2 ml portions) of DIPEA (8.88 ml, 50.8 mmol) over 1 hour. After stirring for a further hour, the reaction mixture was poured into water (450 ml) and EtOAc (450 ml). The aqueous phase was acidified with 5M HCl (50 ml) and the layers were separated. The organic portion was washed with 2M NaOH (200 ml), water (4×200 ml), brine (2×100 ml), dried over $MgSO_4$, filtered and concentrated in vacuo to afford a brown solid. Purification of the solid by chromatography on silica (220 g pre-packed silica cartridge) eluting with 0-50% EtOAc in iso-hexane afforded the racemate, 3-amino-6-methoxy-5-trifluoromethyl-pyridine-2-carboxylic acid (3,3,3-trifluoro-2-hydroxy-2-methyl-propyl)-amide (Ex. 4) as a yellow solid;

1H NMR (400 MHz, DMSO-d6) δ 8.3 (1H, t), 7.7 (1H, s), 6.7 (2H, s), 6.2 (1H, s), 3.9 (3H, s), 3.7 (1H, m), 3.5 (1H, m), 1.2 (3H, s).

LC-MS: Rt 1.24 min; MS m/z 362.4 [M+H]+; Method 2 minLC_v003.

Chiral separation of the racemate by Supercritical Fluid Chromatography was carried out using the following conditions to afford the compounds listed hereinafter:

Mobile Phase: 12% 2-propanol+0.1% DEA/50% $CO_2$

Column: Chiralcel OD-H. 250×10 mm id. 5 μm (2 columns linked in series)

Detection: UV@ 220 nm

Flow rate: 10 ml/min

Sample concentration: 3.5 g in 30 ml EtOH

Injection volume: 100 μl

Examples 5 and 6 are entantiomers.

Example 5

First eluted peak Rt=7.30 minutes. 3-Amino-6-methoxy-5-trifluoromethyl-pyridine-2-carboxylic acid ((S)-3,3,3-trifluoro-2-hydroxy-2-methyl-propyl)-amide:

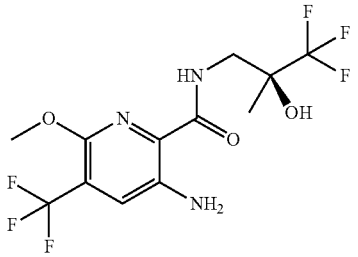

1H NMR (400 MHz, DMSO-d6) δ 8.3 (1H, t), 7.6 (1H, s), 6.6 (2H, broad), 6.2 (1H, s), 3.9 (3H, s), 3.6 (1H, m), 3.5 (1H, m), 1.3 (3H, s);

LC-MS Rt=1.15 mins, [M+H]+ 362.4 (Method 2 minLC_v003).

Optical rotation $[\alpha]^{21}{}_{D}$ at 589 nm −20.83° (c=0.513, MeOH).

The stereochemistry of this compound was confirmed by X-ray crystallography.

Example 6

Second eluted peak Rt=8.29 minutes. 3-Amino-6-methoxy-5-trifluoromethyl-pyridine-2-carboxylic acid ((R)-3,3,3-trifluoro-2-hydroxy-2-methyl-propyl)-amide

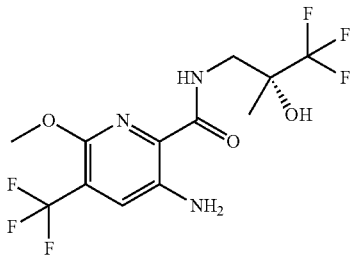

1H NMR (400 MHz, DMSO-d6) δ 8.3 (1H, t), 7.6 (1H, s), 6.6 (2H, broad), 6.2 (1H, s), 3.9 (3H, s), 3.6 (1H, m), 3.5 (1H, m), 1.3 (3H, s);

LC-MS Rt=1.15 mins [M+H]+ 362.4 (Method 2 minLC_v003).

Alternatively, Example 5 may be prepared according to the following method:

To a solution of 3-amino-6-methoxy-5-trifluoromethyl-pyridine-2-carboxylic acid (Intermediate D) (10 g, 42.3 mmol) and (S)-3-amino-1,1,1-trifluoro-2-methylpropan-2-ol hydrochloride (Intermediate RA)(7.60 g, 42.3 mmol) in NMP (400 ml) was added HATU (19.3 g, 50.8 mmol) followed by dropwise addition of DIPEA (22.19 ml, 127 mmol) over ~1 hr. After stirring at room temperature for 30 min, the mixture was added to EtOAc (2 L), washed with 1M NaOH (2×1 L), water (1 L), brine (1 L), dried ($MgSO_4$) and evaporated under reduced pressure to give the crude product as a dark brown oil. Purification by chromatography on silica eluting with a gradient of 1 to-25% of EtOAc in iso-hexane afforded a yellow oil. Recrystallisation of the oil from iso-hexane/DCM afforded 3-amino-6-methoxy-5-trifluoromethyl-pyridine-2-carboxylic acid ((S)-3,3,3-trifluoro-2-hydroxy-2-methyl-propyl)-amide as a crystalline solid;

$^{1}$H NMR (400 MHz, DMSO-d6) δ 8.28 (1H, t), 7.66 (1H, s), 6.67 (2H, s), 6.27 (1H, s), 3.91 (3H, s), 3.65 (1H, m), 3.45 (1H, m), 1.24 (3H, s).

$^{19}$F NMR (376 MHz, DMSO-d6)−62.58 ppm (s), −80.43 ppm (s)

Example 7

3-Amino-6-(4-fluoro-phenyl)-5-trifluoromethyl-pyridine-2-carboxylic acid ((S)-3,3,3-trifluoro-2-hydroxy-2-methyl-propyl)-amide

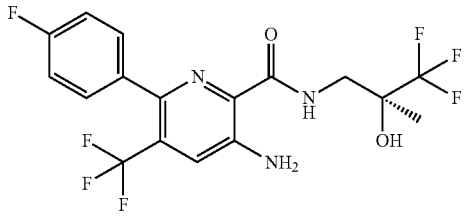

A mixture comprising 3-amino-6-bromo-5-trifluoromethyl-pyridine-2-carboxylic acid ((S)-3,3,3-trifluoro-2-hydroxy-2-methyl-propyl)-amide (Ex. 3)(100 mg, 0.244 mmol), 4-fluorophenylboronic acid (37.5 mg, 0.268 mmol) and 1,1' bis(diphenylphosphoshio) ferrocenepalladium dichloride (19.90 mg, 0.024 mmol) was suspended in THF (2 ml) and 1M $Cs_2CO_3$ (0.667 ml). The vial was flushed with $N_2$, sealed and heated at 160° C. using microwave radiation for 15 minutes. The mixture was partitioned between EtOAc (50 ml) and water (50 ml). The organic portion was separated and washed with brine (30 ml), dried ($MgSO_4$), filtered through Celite® (filter material) and concentrated in vacuo. The crude residue was dissolved in DMSO (2 ml) and purified by mass directed LCMS using MeCN/Water/0.1% TFA eluent to afford clean product. The product fraction obtained as MeCN/Water/0.1% TFA solution was poured into EtOAc (50 ml) and washed with saturated $NaHCO_3$ (50 ml) to free base the product. The organic portion were combined, dried ($MgSO_4$) and concentrated in vacuo to afford the title compound as a pale orange crystalline solid; 1H NMR (400 MHz, DMSO-d6) δ 8.4 (1H, m), 7.7 (1H, s), 7.49 (2H, m), 7.29 (2H, t), 7.2 (2H, br s), 6.22 (1H, s), 3.68 (1H, m), 3.44 (1H, m), 1.22 (3H, s); LC-MS Rt 4.41 mins [M+H]+ 426 (Method 10 minLC_v003).

Example 8

3-Amino-6-(4-fluoro-phenyl)-5-trifluoromethyl-pyridine-2-carboxylic acid ((R)-3,3,3-trifluoro-2-hydroxy-2-methyl-propyl)-amide

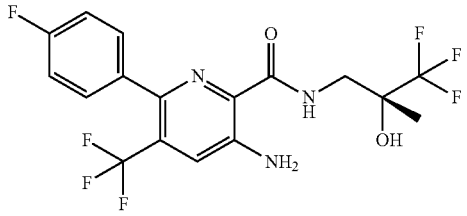

This compound was prepared from 3-Amino-6-bromo-5-trifluoromethyl-pyridine-2-carboxylic acid ((R)-3,3,3-trifluoro-2-hydroxy-2-methyl-propyl)-amide (Ex. 2) analogously to Example 8. 1H NMR (400 MHz, DMSO-d6) δ 8.42 (1H, m), 7.7 (1H, s), 7.5 (2H, m), 7.3 (2H, t), 7.21 (2H, br s), 6.24 (1H, s), 3.68 (1H, m), 3.44 (1H, m), 1.22 (3H, s); LC-MS Rt=4.39 mins [M+H]+ 426 (Method 10 min-LC_v003).

Example 9 and 10

The enantiomers of 3-amino-6-(2,4-dichloro-phenyl)-5-trifluoromethyl-pyridine-2-carboxylic acid (3,3,3-trifluoro-2-hydroxy-2-methyl-propyl)-amide were prepared from 3-Amino-6-(2,4-dichloro-phenyl)-5-trifluoromethyl-pyridine-2-carboxylic acid (Intermediate II) and 3-amino-1,1,1-trifluoro-2-methylpropan-2-ol hydrochloride analogously to Example 1 and separated by chiral separation using Supercritical Fluid Chromatography:

Example 9

First eluted peak. Entantiomer 1 of 3-Amino-6-(2,4-dichloro-phenyl)-5-trifluoromethyl-pyridine-2-carboxylic acid (3,3,3-trifluoro-2-hydroxy-2-methyl-propyl)-amide:

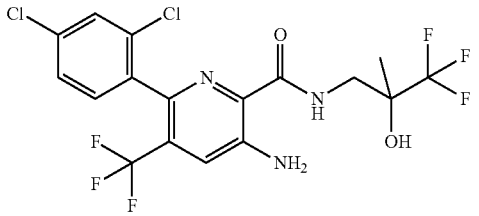

1H NMR (400 MHz, DMSO-d6) δ 8.38 (t, 1H), 7.83 (s, 1H), 7.78 (s, 1H), 7.60 (d, 1H), 7.54 (d, 1H), 7.39 (br s, 2H), 6.25 (br s, 1H). 3.71 (dd, 1H), 3.48 (dd, 1H), 1.26 (s, 3H); LC-MS Rt=1.65 mins [M+H]+ 476 (Method 2 min-LC_v002).

Example 10

Second Eluted peak. Enantiomer 2 of 3-Amino-6-(2,4-dichloro-phenyl)-5-trifluoromethyl-pyridine-2-carboxylic acid (3,3,3-trifluoro-2-hydroxy-2-methyl-propyl)-amide.

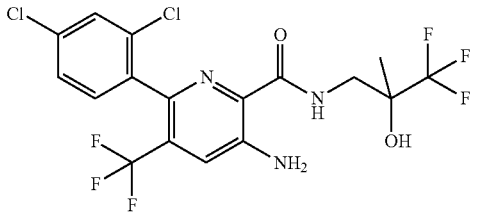

1H NMR (400 MHz, DMSO-d6) δ 8.38 (t, 1H), 7.83 (s, 1H), 7.78 (s, 1H), 7.60 (d, 1H), 7.54 (d, 1H), 7.39 (br s, 2H), 6.25 (br s, 1H). 3.71 (dd, 1H), 3.48 (dd, 1H), 1.26 (s, 3H); LC-MS Rt 1.65 mins [M+H]+=476.1 (Method 2 min-LC_v002).

Example 11

3-Amino-6-(4-fluoro-phenyl)-5-trifluoromethyl-pyridine-2-carboxylic acid (2-hydroxy-2-methyl-propyl)-amide

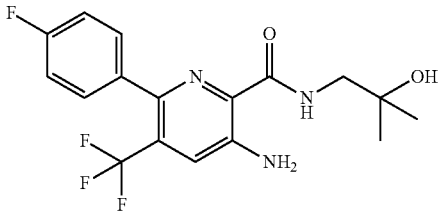

To a stirred suspension of 3-amino-6-bromo-5-trifluoromethyl-pyridine-2-carboxylic acid (2-hydroxy-2-methyl-propyl)-amide (Ex. 1.10) (180 mg, 0.505 mmol) and 4-fluorophenylboronic acid (106 mg, 0.758 mmol) in a 2:1 mixture of toluene:EtOH (12 ml) under nitrogen was added 2M $Na_2CO_3$(aq) (1.011 ml, 2.022 mmol) followed by Pd(dppf) $Cl_2.CH_2Cl_2$ adduct (41 mg, 0.051 mmol). The reaction mixture was heated using microwave radiation at 140° C. for 1 hour and then allowed to cool to RT. The mixture was diluted with EtOAc (100 ml) and washed with water (100 ml). The organic phase was separated, filtered through Celite® (filter material) dried ($MgSO_4$) and concentrated in vacuo to yield a brown oil/solid. Purification by chromatography on silica eluting with MeOH/DCM yielded a yellow oil/solid. This was passed through a 500 mg Isolute® Si-TMT cartridge (2,4,6-trimercaptotriazine silica, pre-wetted with DCM) eluting with 30% MeOH/DCM (50 ml) to afford a yellow oil/solid. The crude product was dried in vacuo and slurried in ~0.5 ml DCM. The resulting suspension was removed by filtration and the filtrate was evaporated to yield the title compound as a light yellow/brown foam-like solid; LC-MS Rt=5.30 mins [M+H]+ 372 (Method 10 minLC_v002).

1H NMR (400 MHz, DMSO-d6), δ 8.29 (1H, t), 7.69 (1H, s), 7.49 (2H, t), 7.29 (2H, t), 7.22 (2H, s), 4.63 (1H, s), 3.24 (2H, d), 1.08 (6H, s).

Example 12

3-Amino-6-methoxy-5-trifluoromethyl-pyridine-2-carboxylic acid (3,3,3-trifluoro-2-hydroxy-propyl)-amide

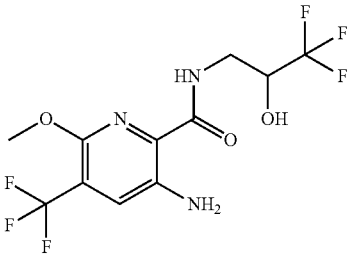

Step 1: 3-(2,5-Dimethyl-pyrrol-1-yl)-6-methoxy-5-trifluoromethyl-pyridine-2-carboxylic acid (3,3,3-trifluoro-2-hydroxy-propyl)-amide This compound was prepared from 3-(2,5-Dimethyl-pyrrol-1-yl)-6-methoxy-5-trifluoromethyl-pyridine-2-carboxylic acid (Intermediate D2) and 3-amino-1,1,1-trifluoropropan-2-ol analogously to Example 1; LC-MS Rt=1.50 mins [M+H]+ 426 (Method 2 minLC_v002).

Step 2: 3-Amino-6-methoxy-5-trifluoromethyl-pyridine-2-carboxylic acid (3,3,3-trifluoro-2-hydroxy-propyl)-amide 3-(2,5-Dimethyl-pyrrol-1-yl)-6-methoxy-5-trifluoromethyl-pyridine-2-carboxylic acid (3,3,3-trifluoro-2-hydroxy-propyl)-amide (350 mg, 0.823 mmol) was dissolved in EtOH (14 ml) and water (7 ml). Hyroxylamine hydrochloride (572 mg, 8.23 mmol) was added followed by TEA (167 mg, 1.646 mmol) and the mixture was heated at reflux overnight. After cooling the RT, the mixture was purified by reverse phase chromatography eluting with MeOH; water (0.1% TFA) to afford the title compound as a pale yellow solid; LC-MS Rt—4.20 min [M+H]+ 348.2 (Method 10 minLC_v002)

1H NMR (400 MHz, DMSO-d6) δ 8.47 (NH, t), 7.66 (1H, s), 6.68 (NH2, b s), 6.51 (OH, d), 4.27-4.20 (1H, m), 3.93 (3H, s), 3.64-3.58 (1H, m), 3.44-3.37 (1H, m)

19F NMR (400 MHz, DMSO-d6) d −62.67 ($CF_3$, s), −77.05 (CF3, s), Trace TFA.

Example 14

5-Amino-6'-methyl-3-trifluoromethyl-[2,3']bipyridinyl-6-carboxylic acid (3,3,3-trifluoro-2-hydroxy-2-trifluoromethyl-propyl)-amide

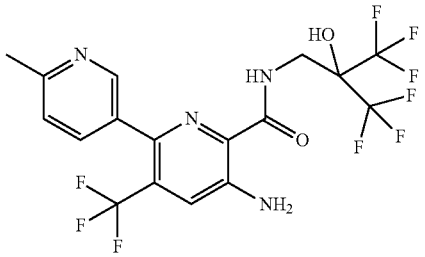

This compound was prepared from 3-Amino-6-bromo-5-trifluoromethyl-pyridine-2-carboxylic acid (3,3,3-trifluoro-2-hydroxy-2-trifluoromethyl-propyl)-amide (Ex. 1.28) and 2-methylpyridine-5-boronic acid analogously to Example 8. LC-MS Rt 1.28 min; 477 [M+H]+; (Method 2 minLC_v002); $^1$H NMR (400 MHz, MeOD) δ 8.50 (1H, s), 7.85 (1H, dd), 7.69 (1H, s), 7.40 (1H, d), 4.00 (2H, s), 2.62 (3H, s).

Example 15

5-Amino-6'-methyl-3-trifluoromethyl-[2,3']bipyridinyl-6-carboxylic acid (3,3,3-trifluoro-2-hydroxy-2-methyl-propyl)-amide

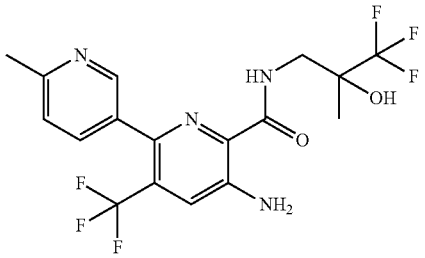

This compound was prepared by chiral separation of 5-amino-6'-methyl-3-trifluoromethyl-[2,3]bipyridinyl-6-carboxylic acid (3,3,3-trifluoro-2-hydroxy-2-methyl-propyl)-amide (Example 1.29) using Supercritical Fluid Chromatography; LC-MS Rt 3.15 min [M+H]+ 423; (Method 10 minLC_v002); 1H NMR (400 MHz, DMSO-d6) δ 8.53 (1H, s), 8.49 (1H, t), 7.75 (1H, d), 7.71 (1H, s), 7.35 (1H, d), 7.25 (2H, s), 6.22 (1H, s), 3.69 (1H, dd), 3.42 (1H, dd), 2.54 (3H, s), 1.22 (3H, s). SFC Retention Time: 4.87 min.

Example 16 and 17

3-Amino-5,6-bis-trifluoromethyl-pyridine-2-carboxylic acid ((S)-3,3,3-trifluoro-2-hydroxy-2-methyl-propyl)-amide and 3-Amino-5,6-bis-trifluoromethyl-pyridine-2-carboxylic acid ((R)-3,3,3-trifluoro-2-hydroxy-2-methyl-propyl)-amide

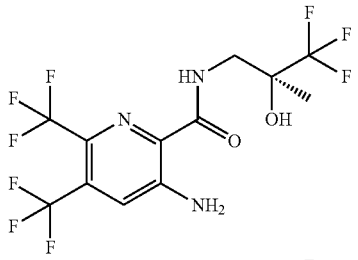

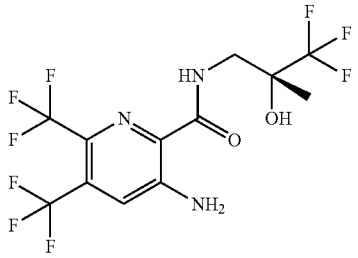

Step 1: 3-(2,5-Dimethyl-pyrrol-1-yl)-5,6-bis-trifluoromethyl-pyridine-2-carboxylic acid (3,3,3-trifluoro-2-hydroxy-2-methyl-propyl)-amide To a stirred solution of 3-(2,5-dimethyl-pyrrol-1-yl)-5,6-bis-trifluoromethyl-pyridine-2-carboxylic acid (Intermediate M) (1.16 g, 3.29 mmol) in NMP (32 ml) was added 3-Amino-1,1,1-trifluoro-2-methyl-propan-2-ol hydrochloride (commercially available) (591 mg, 3.29 mmol) followed by HATU (1.25 g, 3.29 mmol) and $NEt_3$ (918 ul, 6.59 mmol) and the reaction mixture was left to stir at RT. After 1 h a further 0.2 equiv. $NEt_3$ was added. After 15 min a further 0.4 equiv. $NEt_3$ and 0.2 equiv. amine were added. After 30 min a further 0.1 equiv HATU was added. After 30 min most of the starting material had been consumed. The reaction mixture was added to EtOAc (50 ml), washed with 0.1M NaOH and the aqueous layer was back extracted with EtOAc (2×50 ml). The combined organic extracts were washed with water (2×150 ml), brine (100 ml), dried ($MgSO_4$) and concentrated in vacuo to give the crude product as an orange oil.

The crude material was purified by chromatography on silica eluting with 0-15% EtOAc in iso-hexane to afford the title product as a yellow solid; LC-MS Rt 1.32 min; MS m/z 478.2 [M+H]+; Method 2 minLC_v003.

Step 2: 3-Amino-5,6-bis-trifluoromethyl-pyridine-2-carboxylic acid (3,3,3-trifluoro-2-hydroxy-2-methyl-propyl)-amide To a stirred solution of 3-(2,5-dimethyl-pyrrol-1-yl)-5,6-bis-trifluoromethyl-pyridine-2-carboxylic acid (3,3,3-trifluoro-2-hydroxy-2-methyl-propyl)-amide (985 mg, 2.064 mmol) in 2:1 EtOH/$H_2O$ (7.5 ml) was added hydroxylamine hydrochloride (1.43 g, 20.64 mmol) followed by $NEt_3$ (575 ml, 4.13 mmol). The reaction mixture was heated to reflux (~98° C.) for 11.5 hours and then allowed to cool to RT. The solvent was removed in vacuo and the resulting residue was partitioned between EtOAc (25 ml) and water (25 ml). The aqueous layer was separated and extracted with EtOAc (2×25 ml) and the combined organic extracts were washed with brine (50 ml), dried ($MgSO_4$) and concentrated in vacuo. The crude material was purified by chromatography on silica eluting with 0-25% EtOAc in iso-hexane to afford the title product as a pale yellow solid; LC-MS: Rt 1.24 min; MS m/z 400.0 [M+H]+; Method 2 minLC_v003.

Step 3: 3-Amino-5,6-bis-trifluoromethyl-pyridine-2-carboxylic acid ((S)-3,3,3-trifluoro-2-hydroxy-2-methyl-propyl)-amide and 3-Amino-5,6-bis-trifluoromethyl-pyridine-2-carboxylic acid ((R)-3,3,3-trifluoro-2-hydroxy-2-methyl-propyl)-amide

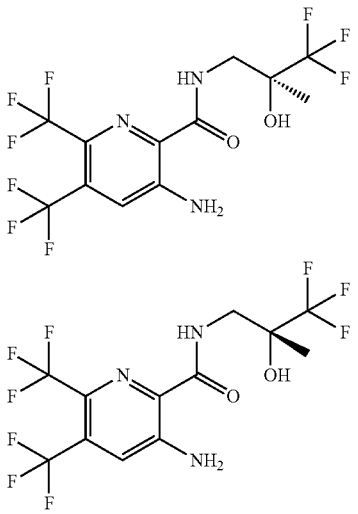

These compounds were prepared by chiral separation of 3-amino-5,6-bis-trifluoromethyl-pyridine-2-carboxylic acid (3,3,3-trifluoro-2-hydroxy-2-methyl-propyl)-amide;
Enantiomer 1: LC-MS Rt 1.23 min; MS m/z 400.0 [M+H]+; Method 2 minLC_v003. SFC Retention Time 5.07 min.
Enantiomer 2: LC-MS Rt 1.23 min; MS m/z 400.0 [M+H]+; Method 2 minLC_v003. SFC Retention Time 5.13 min.

Example 18

3-Amino-6-methoxy-N-(3,3,3-trifluoro-2-(4-methoxybenzylamino)-2-methylpropyl)-5-(trifluoromethyl)picolinamide

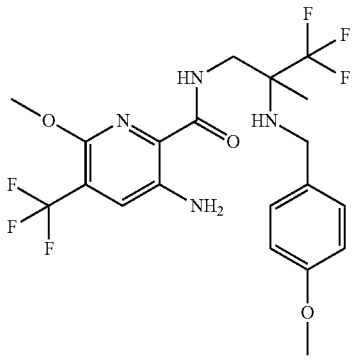

The title compound was prepared analogously to Example 1 from 3-amino-6-methoxy-5-trifluoromethyl-pyridine-2-carboxylic acid (Intermediate D) and 3,3,3-trifluoro-N2-(4-methoxybenzyl)-2-methylpropane-1,2-diamine (Intermediate N). DIPEA was used in this reaction. 1H NMR (400 MHz, DMSO-d6) δ 8.27 (1H, m), 7.68 (1H, s), 7.25 (2H, d), 6.83 (2H, d), 6.70 (2H, s), 3.85 (3H, s), 3.75 (2H, m), 3.72 (3H, s), 3.70 (1H, m), 3.47 (1H, m), 2.80 (1H, t), 1.24 (3H, s)

Example 19

3-Amino-N-(2-amino-3,3,3-trifluoro-2-methylpropyl)-6-methoxy-5-(trifluoromethyl)

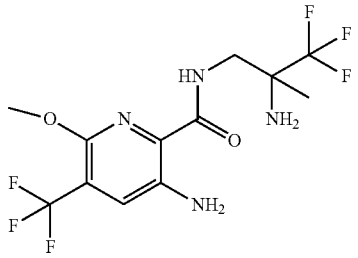

A mixture comprising 3-amino-6-methoxy-N-(3,3,3-trifluoro-2-(4-methoxybenzylamino)-2-methylpropyl)-5-(trifluoromethyl)picolinamide (Ex. 18) (0.9 g, 1.873 mmo) in TFA (50 ml) was heated to 50° C. for 2 h. After cooling to RT, the pH was adjusted to pH 12 using 2M NaOH. The product was extracted with DCM and the organic extract was washed with water, dried over $MgSO_4$ and concentrated in vacuo. The crude product was loaded onto a SCX-2 cartridge eluting with MeOH followed by 2M NH3 in MeOH. The methanolic ammonia fractions were concentrated in vacuo and dried under vacuum to afford the title compound. 1H NMR (400 MHz, DMSO-d6) δ 8.35 (1H, m), 7.67 (1H, s), 6.67 (2H, s), 3.93 (3H, s), 3.58 (1H, m), 3.40 (1H, m), 2.22 (2H, s), 1.14 (3H, s). LC-MS Rt 0.94 min; MS m/z 361.2 [M+H]+; Method 2 minLC_v003.

Example 20

3-Amino-6-(pyrrolidin-1-yl)-N-(3,3,3-trifluoro-2-hydroxy-2-methylpropyl)-5-(trifluoromethyl)picolinamide

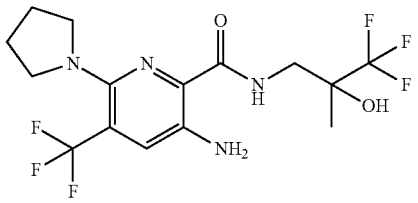

Step 1: 3-(2,5-Dimethyl-1H-pyrrol-1-yl)-6-(pyrrolidin-1-yl)-N-(3,3,3-trifluoro-2-hydroxy-2-methylpropyl)-5-(trifluoromethyl)picolinamide The title compound was prepared from Intermediate DA analogously to Example 1; LC-MS Rt 1.42 min; MS m/z 479.3 [M+H]+; Method 2 minLC_v003.

Step 2: 3-Amino-6-(pyrrolidin-1-yl)-N-(3,3,3-trifluoro-2-hydroxy-2-methylpropyl)-5-(trifluoromethyl)picolinamide This compound was prepared from 3-(2,5-dimethyl-1H-pyrrol-1-yl)-6-(pyrrolidin-1-yl)-N-(3,3,3-trifluoro-2-hydroxy-2-methylpropyl)-5-(trifluoromethyl)picolinamide analogously to Intermediate D (final step). The resulting racemate was separated by SFC to afford the title compound; First eluted peak:

1H NMR (400 MHz, DMSO-d6) δ 8.24 (1H, m), 7.6 (1H, s), 6.4 (2H, br s), 6.32 (1H, s), 3.64 (1H, m), 3.48 (1H, m), 3.35 (4H), 1.88 (4H, m), 1.25 (3H, s); LC-MS Rt 3.87 min; MS m/z 401.3 [M+H]+; Method 10 minLC_v003.

Example 21

(S)-3-amino-6-ethoxy-N-(3,3,3-trifluoro-2-hydroxy-2-methylpropyl)-5-(trifluoro methyl)picolinamide

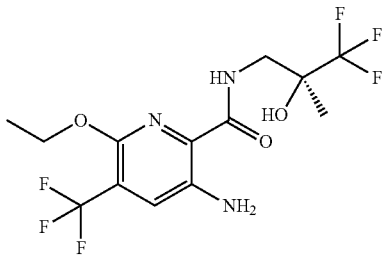

The title compound was prepared from Intermediate DB and Intermediate R analogously to Example 20; 1H NMR (400 MHz, DMSO-d6) δ 8.3 (1H, t), 7.7 (1H, s), 6.6 (2H, broad), 6.3 (1H, s), 4.4 (2H, q), 3.6 (1H, mult), 3.5 (1H, mult), 1.3 (3H, t), 1.2 (3H, s).

LC-MS Rt 1.20 min; MS m/z 376.2 [M+H]+; Method 2 minLC_v003.

Example 22

3-Amino-6-bromo-N-(2-morpholinoethyl)-5-(trifluoromethyl)pyrazine-2

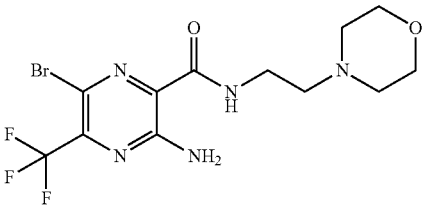

To a stirred solution of 3-amino-6-bromo-5-trifluoromethyl-pyrazine-2-carboxylic acid (Intermediate C) (250 mg, 0.874 mmol) in NMP (8 ml) was added 4-(2-aminoethyl) morphonline (138 ul, 1.049 mmol) followed by DIPEA (763 ul, 4.37 mmol). To this solution was then added HATU (499 mg, 1.311 mmol) in portions and the reaction mixture was left to stir at RT for 1 hour. A further 1 equiv. of 4-(2-aminoethyl)morphonline was added. After a further 1.5 hr, 0.5 equiv. HATU (166 mg, 0.425 mmol) was added and the RM was left to stir for a further 30 min. The mixture was added to EtOAc (50 ml) and washed with 0.1M NaOH (50 ml). The aqueous layer was back extracted with EtOAc (50 ml). The combined organics were washed with water (50 ml), brine (50 ml), dried over magnesium sulfate and evaporated under reduced pressure to give a brown oil (418 mg). The crude product was purified by chromatography (Biotage-silica 20 g/70 ml column, 3:1 EtOAc/iso-hexane). The resulting yellow residue was loaded onto an SCX-2 cartridge (10 g) that had been pre-wetted with MeOH. The cartridge was washed with MeOH (140 ml) and eluted with 3.5M ammonia in methanol solution (70 ml). The appropriate fractions were evaporated under reduced pressure to give a solid. This solid was dissolved in EtOAc and filtered under vacuum. The filtrate was evaporated under reduced pressure and then dried in vacuo to afford the title compound as a yellow solid;

LC-MS: Rt 2.61 min; MS m/z 398.2 [M+H]+; Method 10 minLC_v002

1H NMR (400 MHz, DMSO-d6) δ 8.70 (1H, s), 8.10 (2H, s), 3.58 (4H, t), 3.40 (2H, q), 2.45 (2H, m), 2.40 (4H, s).

Example 23

N-(2-(1H-imidazol-2-yl)propyl)-3-amino-6-bromo-5-(trifluoromethyl)pyrazine-2-carboxamide

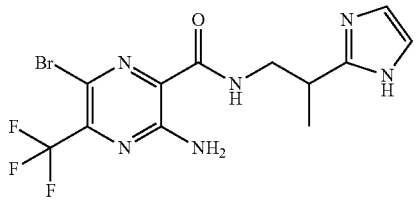

The title compound was prepared from 3-amino-6-bromo-5-trifluoromethyl-pyrazine-2-carboxylic acid (Intermediate C) and 2-(1H-imidazol-2-yl)propan-1-amine (prepared according to the procedure of Steffens, Robert; Schunack, Walter. Histamine analogs, XXVI. Racemic histamine H1-agonists. Archiv der Pharmazie (Weinheim, Germany) (1984), 317(9), 771-6; 1H NMR (400 MHz, DMSO-d6) δ 11.8 (1H, s), 9.0 (1H, t), 8.1 (2H, s), 7.0 (1H, s), 6.8 (1H, s), 3.55 (2H, m), 3.15 (1H, m), 1.2 (3H, d). LC-MS [M+H]+ 393.0/395.1

Example 24a and 24b

Enantiomers of 3-amino-N-(3,3,3-trifluoro-2-hydroxy-2-methylpropyl)-5,6-bis(trifluoromethyl)pyrazine-2-carboxamide

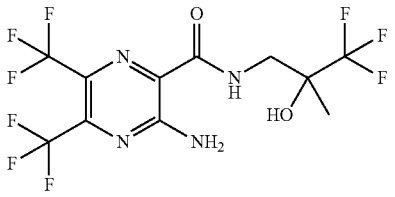

The title compound was prepared from Intermediate BA and 3-amino-1,1,1-trifluoro-2-methylpropan-2-ol analogously to Example 4. Chiral separation of the racemate by Supercritical Fluid Chromatography afforded the title compound;

Example 24a

First eluted peak: Enantiomer 1 of 3-amino-N-(3,3,3-trifluoro-2-hydroxy-2-methylpropyl)-5,6-bis(trifluoromethyl)pyrazine-2-carboxamide;

1H NMR (400 MHz, DMSO-d6) δ 8.61-8.74 (1H, broad hump), 8.5-8.61 (1H, broad hump), 8.46 (1H, t), 6.3 (1H, s), 3.69 (1H, m), 3.5 (1H, m), 1.29 (3H, s)

LC-MS: Rt 4.23 min; MS m/z 401.2 [M+H]+; Method 10 minLC_v003.

Example 24b

Second eluted peak: Enantiomer 2 of 3-amino-N-(3,3,3-trifluoro-2-hydroxy-2-methylpropyl)-5,6-bis(trifluoromethyl)pyrazine-2-carboxamide;

1H NMR (400 MHz, DMSO-d6) δ 8.61-8.76 (1H, broad hump), 8.5-8.60 (1H, broad hump), 8.46 (1H, t), 6.3 (1H, s), 3.69 (1H, m), 3.5 (1H, m), 1.29 (3H, s)

LC-MS: Rt 4.24 min; MS m/z 401.2 [M+H]+; Method 10 minLC_v003. Optical rotation $[\alpha]^{21}{}_{D}$ at 589 nm+22.0° (c=0.517, MeOH).

Example 25

3-Amino-6-(1-methyl-1H-pyrazol-4-yl)-N-(3,3,3-trifluoro-2-hydroxy-2-methylpropyl)-5-(trifluoromethyl)picolinamide

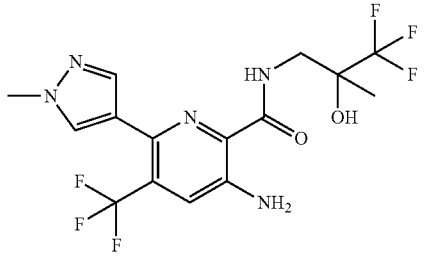

Step 1: 3-Amino-6-(1-methyl-1H-pyrazol-4-yl)-5-(trifluoromethyl)picolinic acid

3-Amino-6-bromo-5-trifluoromethyl-pyridine-2-carboxylic acid methyl ester (Intermediate A4) (500 mg, 1.672 mmol), $PdCl_2$(dppf).$CH_2Cl_2$ adduct (205 mg, 0.251 mmol), 1-methyl-4-(4,4,5,5-tetramethyl-1,3,2-dioxaborolan-2-yl)-1H-pyrazole (383 mg, 1.839 mmol) and $Cs_2CO_3$ (6.69 ml, 6.69 mmol) in THF (12 ml) under $N_2$, was heated using microwave radiation at 150° C. for 10 minutes. 2M NaOH (5 ml) was added and the mixture was stirred at RT overnight. The mixture was filtered through Celite® (filter material) and the organic solvent was removed. The resulting aqueous layer was washed with EtOAc and acidified to pH1. The product was extracted with DCM and concentrated in vacuo to afford the title compound;

Step 2; 3-Amino-6-(1-methyl-1H-pyrazol-4-yl)-N-(3,3,3 -trifluoro-2-hydroxy-2-methylpropyl)-5-(trifluoromethyl)picolinamide The title compound was prepared from 3-amino-6-(1-methyl-1H-pyrazol-4-yl)-5-(trifluoro methyl)picolinic acid and 3-amino-1,1,1-trifluoro-2-methylpropan-2-ol analogously to Example 4 1H NMR (400 MHz, Methanol-d4) δ 7.97 (1H, s), 7.85 (1H, s), 7.60 (1H, s), 3.97 (3H, s), 3.77 (1H, m), 3.56 (1H, m), 1.37 (3H, s)

LC-MS: Rt 3.22 min; MS m/z 412.3 [M+H]+; Method 10 minLC_v003.

Example 26

3-Amino-6-furan-2-yl-5-trifluoromethyl-pyrazine-2-carboxylic acid [2-(2-methoxy-phenyl)-ethyl]-amide

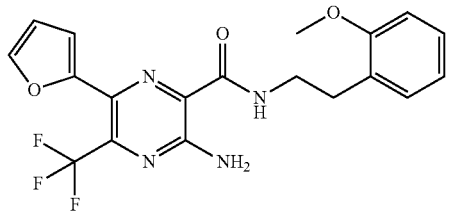

The title compound was prepared from 3-amino-6-furan-2-yl-5-trifluoromethyl-pyrazine-2-carboxylic acid (Intermediate PA) and the appropriate amine; MS m/z 406.93 [M+H]+

Preparation of Intermediates

Intermediate A

3-Amino-6-bromo-5-trifluoromethyl-pyridine-2-carboxylic acid

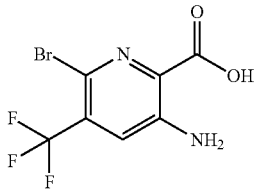

Intermediate A1:
2-Bromo-3-nitro-5-trifluoromethyl-pyridine

3-Nitro-5-(trifluoromethyl)pyridin-2-ol (31.00 g, 149 mmol) was dissolved in acetonitrile (250 ml) to give a dark brown solution. Phosphorus(V) oxybromide (85 g, 298 mmol) was added and the mixture was heated at reflux for 4.5 hours and then stirred at RT overnight. The reaction mixture was quenched by pouring into vigorously stirring water (600 ml) containing sodium hydrogencarbonate (110 g). The dark brown mixture was extracted with DCM (3×200 ml) and the organic phase was washed with water (200 ml) and brine (100 ml), dried ($MgSO_4$) and concentrated in vacuo to afford the title product as a brown oil. $^1$H-NMR: [400 MHz, $CDCl_3$, $\delta_H$, 8.87 (1H, d, J=1.4 Hz, ArH), 8.39 (1H, d, J=1.9 Hz, ArH).

Intermediate A2:
3-Nitro-5-trifluoromethyl-pyridine-2-carbonitrile

2-Bromo-3-nitro-5-trifluoromethyl-pyridine (10.00 g, 36.87 mmol) was dissolved in toluene (250 ml) with stirring to give a pale yellow solution. Tetrabutylammonium bromide (11.90 g, 36.9 mmol) was added followed by copper(I) cyanide (9.92 g, 111 mmol) and the mixture was heated at reflux for 10 h. After cooling to RT, the reaction mixture was partitioned between water (750 ml) and EtOAc (750 ml). The organic fractions were combined, washed with water (2×250 ml) and brine (100 ml), dried ($MgSO_4$) and concentrated in vacuo to afford the title product. $^1$H-NMR: [400 MHz, DMSO-$d_6$ $\delta_H$ 9.55 (1H, m, ArH), 9.24 (1H, m, ArH)

Intermediate A3:
3-Amino-5-trifluoromethyl-pyridine-2-carboxylic acid methyl ester 3-Nitro-5-trifluoromethyl-pyridine-2-carbonitrile (6.5 g, 29.9 mmol) was dissolved in EtOAc (150 ml) to give a pale yellow solution and placed under an atmosphere of nitrogen. 10% Palladium on activated carbon (3.19 g, 2.99 mmol) was added and the reaction mixture stirred under an atmosphere of hydrogen for 18 hours. The reaction mixture was filtered and concentrated in vacuo. The crude residue was dissolved in HCl conc. (45 ml) and heated to reflux for 24 hours. The reaction mixture was allowed to cool to RT and concentrated in vacuo. The solid was dissolved in MeOH (300 ml) and sulfuric acid (14.4 ml) was added. The resulting solution was heated at reflux for 48 hours. The reaction was allowed to cool to RT, then neutralised by addition of 10% $NaHCO_{3(aq)}$ (600 ml). The product was extracted into DCM (3×200 ml) and the combined organic phases were washed with water (200 ml), brine (50 ml), ($MgSO_4$) and concentrated in vacuo. The resulting solid was purified by chromatography on silica: Eluant gradient: isohexane (500 ml), 10% EtOAc in isohexane (1000 ml), 20% EtOAc in isohexane (1500 ml) to afford the titled compound as a pale yellow solid $^1$H-NMR: [400 MHz, DMSO-$d_6$, $\delta_H$ 8.13 (1H, d, J=1.7 Hz, ArH), 7.60 (1H, d, J=1.3 Hz, ArH), 7.01 (2H, br, $NH_2$), 3.85 (3H, s, $ArOCH_3$), m/z 221.1 $[M+H]^+$ Intermediate A4: 3-Amino-6-bromo-5-trifluorom-ethyl-pyridine-2-carboxylic acid methyl ester 3-Amino-5-trifluoromethyl-pyridine-2-carboxylic acid methyl ester (9.49 g, 43.16 mmol) was suspended in water (300 ml). Sulfuric acid (4.60 ml, 86 mmol) was added followed by dropwise addition over 30 minutes of a solution of bromine (2.222 ml, 43.1 mmol) in acetic acid (29.6 ml, 517 mmol). The reaction mixture was stirred at RT for 18 hours. A further 100 ml of water was added, followed by a further 0.25 equivalents of the bromine/AcOH mixture (550 μL bromine in 7.4 ml AcOH) and the reaction mixture stirred at RT for an additional 90 minutes. The reaction mixture was diluted with 500 ml water and neutralised by addition of solid $NaHCO_3$ (~85 g). The suspension was extracted with DCM (3×300 ml) and the combined organic phases washed with sat.NaH $CO_{3(aq)}$ (250 ml), water (250 ml) and brine (100 ml), dried ($MgSO_4$) and concentrated in vacuo. The crude material was recrystallised from boiling MeOH (~300 ml) to give the title product as a pale orange solid m/z 301.0 $[M+H]^{+1}$H-NMR: [400 MHz, DMSO-$d_6$ $\delta_H$ 7.77 (1H, s, ArH), 7.17 (2H, s, $NH_2$), 3.86 (3H, s, $ArCO_2CH_3$).

Intermediate A: 3-Amino-6-bromo-5-trifluorom-ethyl-pyridine-2-carboxylic acid

3-Amino-6-bromo-5-trifluoromethyl-pyridine-2-carboxylic acid methyl ester (1.40 g, 4.68 mmol) was suspended in MeOH (15 ml); Sodium hydroxide (2.0 M aqueous solution) (14.04 ml, 28.1 mmol) was added and the suspension was stirred at RT overnight. The mixture was concentrated in vacuo and the resulting residue was dissolved in water (100 ml) and then acidifed by the addition of 5.0M HCl(aq). The product was extracted into ethyl acetate (2×75 ml) and the combined organic extracts were washed with water (50 ml), brine (25 ml), dried ($MgSO_4$) and concentrated in vacuo to afford the title product as a yellow solid. $^1$H-NMR: [400 MHz, DMSO-$d_6$, $\delta_H$ 13.24 (1H, br s, $CO_2H$), 7.74 (1H, s, ArH), 7.17 92H, br s ArN $H_2$). m/z 285.1, 287.1 $[M+H]^+$ Intermediate B 3-Amino-5-trifluoromethyl-pyrazine-2-carboxylic acid ethyl ester

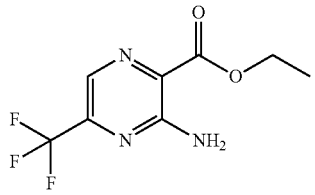

Intermediate B1: Carbamimidoyl-nitroso-acetic acid ethyl ester

To a solution of 2M ammonia in Ethanol (152 ml, 0.304 mmol) at 0° C. to 5° C., ethyl ethoxycarbonylacetimidate HCl (25 g, 0.127 mmol) was added over 30 minutes. The reaction was stirred vigorously at this temperature for 3 hours, after which a solution of sodium nitrite in water (9.63 g, 0.139 mmol) was added in a single portion. The pH of the mixture was adjusted to pH6 with the addition of 5N HCl. The reaction mixture was left to stir at RT overnight. The yellow precipitate formed was filtered under vacuum, washed with water and dried to give the title compound;

$^1$H NMR (400 MHz, DMSO-d6) δ 10.1 (2H, br s), 7.6 (2H, br s), 4.3 (2H, $_q$), 1.3 (3H, t).

Intermediate B2: Amino-carbamimidoyl-acetic acid ethyl ester

To a solution of carbamimidoyl-nitroso-acetic acid ethyl ester (5.5 g, 31.4 mmol) in ethanol/5M HCl (1:1 ratio, 250 ml) was added 10% Pd/C (1.3 g). The reaction mixture was hydrogenated ($H_{2(g)}$) at low pressure over 2 nights. The Pd/C was filtered through Celite® (filter material) and the filtrate reduced in vacuo to give the title compound as a white solid. This was taken through to the next step as crude.

Intermediate B:
3-Amino-5-trifluoromethyl-pyrazine-2-carboxylic acid ethyl ester To a mixture of amino-carbamimidoyl-acetic acid ethyl ester (2 g, 9.22 mmol) and water (50 ml), a 20% aqueous solution of trifluoropyruvic aldehyde (2.32 g, 18.43 mmol) was added. To this mixture, sodium acetate (5.29 g, 64.52 mmol) was added (pH of the reaction mixture was pH5). The reaction mixture was left to stir at RT overnight. The resultant precipitate was filtered under vacuum purification by chromatography on silica eluting with iso-hexane: EtOAc (gradient of 0 to 10% EtOAc) afforded the title compound $^1$H NMR (400 MHz, DMSO-d6) δ 8.4 (1H, s), 7.8 (2H, br s), 4.4 (2H, q), 1.4 (3H, t).

Intermediate BA

3-Amino-5,6-bis(trifluoromethyl)pyrazine-2-carboxylic acid

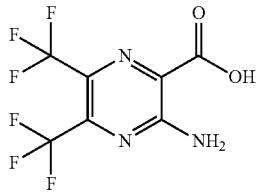

Step 1: Ethyl 3-amino-5,6-bis(trifluoromethyl)pyrazine-2-carboxylate

The title compound was prepared from amino-carbamimidoyl-acetic acid ethyl ester (Intermediate B2) and 1,1,1,4,4,4-hexafluorobutane-2,3-dione analogously to Intermediate B; 10 LCMS Rt=4.72 minutes, [M+H]+ 304.2/326.1 Method 10 minLC_v002.

Step 2: 3-Amino-5,6-bis(trifluoromethyl)pyrazine-2-carboxylic acid

To a stirring solution of ethyl 3-amino-5,6-bis(trifluoromethyl)pyrazine-2-carboxylate (300 mg, 0.990 mmol) in EtOH (10 ml), 2M NaOH (0.495 ml, 0.990 mmol) was added dropwise over 1 minute. After stirring at RT for 30 minutes the reaction mixture was poured into water (30 ml) and the pH was adjusted to pH 4 by addition of 1M HCl. The mixture was extracted with EtOAc (2×50 ml) and the combined organic extracts were washed with brine (30 ml), dried over $MgSO_4$ (5 g), filtered and concentrated in vacuo to afford the title compound as an off white crystalline solid; $^1$H NMR (400 MHz, DMSO-d6) δ 8.6-9.2 (2H, broad hump), 7.8-8.3 (2H, broad hump), 4.4 (2H, q), 1.32 (3H, t).

Intermediate C

3-Amino-6-bromo-5-trifluoromethyl-pyrazine-2-carboxylic acid

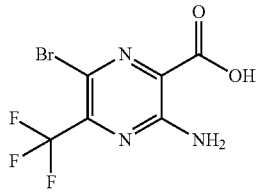

Intermediate C1: 3-Amino-6-bromo-5-trifluoromethyl-pyrazine-2-carboxylic acid ethyl ester To a solution of 3-amino-5-trifluoromethyl-pyrazine-2-carboxylic acid ethyl ester (Intermediate B) (30 mg, 0.13 mmol) in acetic acid (5 ml), sodium carbonate (15 mg, 0.14 mmol) was added. To this mixture, half the contents of a solution of bromine (7 μL, 0.13 mmol) in acetic acid (5 ml) were added, followed by the addition of sodium carbonate ((15 mg, 0.14 mmol). The remaining solution of bromine in acetic acid was added and the reaction mixture was left to stir at RT for 2 hours. The mixture was diluted with water and the resulting yellow precipitate was filtered under vacuum to afford the title compound.

Intermediate C: 3-Amino-6-bromo-5-trifluoromethyl-pyrazine-2-carboxylic acid

To a stirring solution of 3-amino-5-trifluoromethyl-pyrazine-2-carboxylic acid ethyl ester (10 g, 31.8 mmol) in ethanol (20 ml), 2M NaOH (20 ml, 31.8 mmol) was added. The resulting solution was stirred at RT for 5 minutes and poured into water (50 ml). The pH was adjusted to pH6 with the addition of 1M HCl. The resulting suspension was filtered under vacuum, washed with water (20 ml) and dried to afford the title compound; MS m/z 287 $[M+H]^+$. $^1$H NMR (400 MHz, DMSO-d6) δ 7.98 (2H, s).

Intermediate D

3-Amino-6-methoxy-5-trifluoromethyl-pyridine-2-carboxylic acid

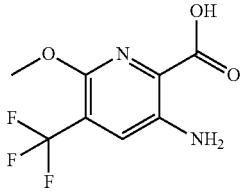

Intermediate D1: 6-Bromo-3-(2,5-dimethyl-pyrrol-1-yl)-5-trifluoromethyl-pyridine-2-carboxylic acid methyl ester

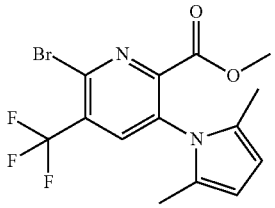

3-Amino-6-bromo-5-trifluoromethyl-pyridine-2-carboxylic acid methyl ester (Intermediate A4) (2 g, 6.69 mmol) was suspended in toluene (8 ml), and treated with p-toluenesulfonic acid (TsOH) (0.115 g, 0.669 mmol) and acetonylacetone (0.941 ml, 8.03 mmol). The reaction mixture was heated at reflux for 2 hours (using Dean-Stark apparatus) and allowed to cool to RT overnight. The resulting dark red/black solution was concentrated in vacuo to remove toluene and the crude residue diluted with EtOAc (200 ml), washed with $NaHCO_3$ (50 ml), dried ($MgSO_4$) and concentrated in vacuo to give a brown solid. Purification of the solid by chromatography on silica eluting with EtOAc/iso-hexane afforded the title compound; LC-MS Rt=5.58 min [M+H]+ 377/379 (Method 10 minLC_v002).

1H NMR (400 MHz, DMSO-d6) δ 8.50 (1H, s), 7.77 (2H, s), 5.83 (3H, s), 1.90 (6H, s); 19F NMR (400 MHz, DMSO-d6) δ −62.26 (CF3, s).

Intermediate D2: 3-(2,5-Dimethyl-pyrrol-1-yl)-6-methoxy-5-trifluoromethyl-pyridine-2

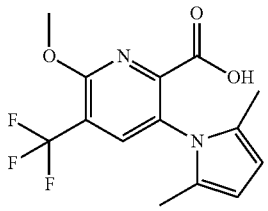

6-Bromo-3-(2,5-dimethyl-pyrrol-1-yl)-5-trifluoromethyl-pyridine-2-carboxylic acid methyl ester (2 g, 5.30 mmol) was dissolved in MeOH (40 ml) and treated with 2M NaOH (20 ml) to give a suspension which was stirred at RT for 1 h to afford a clear solution. The solvent was removed in vacuo and the resulting residue was acidified to pH1 with 5M HCl. The mixture was extracted with EtOAc (200 ml) and the organic extract was dried ($MgSO_4$) and concentrated in vacuo to afford the title compound as a dark brown solid which was used in the next step without further purification; LC-MS Rt=1.50 min [M+H]+ 315.2.1/316.2 (Method 2 minLC_v002); 1H NMR (400 MHz, DMSO-d6) δ14.42-12.61 (COOH, b), 8.25 (1H, s), 5.84 (2H, s), 4.13 (3H, s), 1.97 (6H, s); 19F NMR (400 MHz, DMSO-d6) δ −62.43 (CF3, s).

Intermediate D: 3-Amino-6-methoxy-5-trifluoromethyl-pyridine-2-carboxylic acid 3-(2,5-Dimethyl-pyrrol-1-yl)-6-methoxy-5-trifluoromethyl-pyridine-2-carboxylic acid (2.1 g, 6.68 mmol) was dissolved in EtOH (40 ml) and water (20 ml). To this mixture was added TEA (2.79 ml, 20.05 mmol) followed by hydroxylamine hydrochloride (4.64 g, 66.8 mmol). The resulting mixture was heated at reflux for 5 hours. After cooling to RT, the mixture was diluted with EtOAc (100 ml) and washed with aqueous HCl (1M, 100 ml). The aqueous phase was back extracted with EtOAc (100 ml) and the combined organic phases washed with brine (100 ml), dried (MgSO4) and concentrated in vacuo to afford the product as an orange solid. The material can be used crude or recrystallised from isohexane-EtOAc (10:1) LC-MS Rt=1.0 min [M+H]+ 237 (Method 2 minLC_v003)

1H NMR (400 MHz, DMSO-d6) δ 8.5 (NH2, b), 7.70 (1H, s), 3.89 (3H, s).

Intermediate DA 3-(2,5-Dimethyl-1H-pyrrol-1-yl)-6-(pyrrolidin-1-yl)-5-(trifluoromethyl)picolinic acid

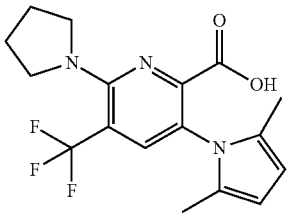

Step 1: 6-Bromo-3-(2,5-dimethyl-1H-pyrrol-1-yl)-5-(trifluoromethyl)picolinic acid 6-Bromo-3-(2,5-dimethyl-pyrrol-1-yl)-5-trifluoromethyl-pyridine-2-carboxylic acid methyl ester (1.9 g, 5.04 mmol) and 2M NaOH (2.52 ml, 5.04 mmol) in THF (10 ml) was stirred at RT for 1 hour. The reaction mixture was poured into water (50 ml) and the pH was adjusted to pH 4 by addition of 1M HCl. The mixture was extracted with EtOAc (2×50 ml) and the organic portion was washed with brine (30 ml), dried over $MgSO_4$ (5 g), filtered and concentrated to give the title compound as a crystalline orange solid; LC_MS Rt=1.21 min [M+H]+ 363.1 (Method 2 min-LC_v003).

Step 2: 3-(2,5-Dimethyl-1H-pyrrol-1-yl)-6-(pyrrolidin-1-yl)-5-(trifluoromethyl)picolinic acid To a stirring solution of 6-bromo-3-(2,5-dimethyl-1H-pyrrol-1-yl)-5-(trifluoromethyl) picolinic acid (300 mg, 0.826 mmol) in THF (1 ml), pyrrolidine (0.136 ml, 1.652 mmol) was added. The orange solution was stirred at RT overnight. The reaction mixture was partitioned between 0.5M HCl (30 ml) and EtOAc (30 ml) and shaken. The organic portion was separated and washed with brine (30 ml), dried over $MgSO_4$, filtered and concentrated in vacuo to give a red oil. The crude product was purified on silica eluting with 0-40% EtOAc in iso-hexane to afford the title product;

1H NMR (400 MHz, DMSO d6) δ 13.45 (1H, br s), 7.88 (1H, s), 5.74 (2H, s), 3.58 (5H, br s), 1.88-2.0 (11H, unresolved peaks).

Intermediate DB 3-(2,5-Dimethyl-1H-pyrrol-1-yl)-6-ethoxy-5-(trifluoromethyl)picolinic acid

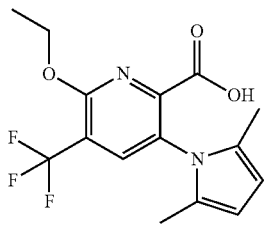

Step 1: Methyl 3-(2,5-dimethyl-1H-pyrrol-1-yl)-6-methoxy-5-(trifluoromethyl)picolinate 3-(2,5-Dimethyl-pyrrol-1-yl)-6-methoxy-5-trifluoromethyl-pyridine-2-carboxylic acid (Intermediate D2)(500 mg, 1.591 mmol) in methanol (15.91 ml) was treated with $H_2SO_4$ (0.0424 ml, 0.795 mmol) and the solution was heated at reflux for overnight. The solvent removed was removed in vacuo and the resulting brown oil was neutralised to pH 7 using saturated sodium bicarbonate. The mixture was extracted with EtOAc (20 ml) and the combined organic extracts were washed with water (20 ml), brine (20 ml), passed though a phase separator and concentrated in vacuo. Purification of the crude product by chromatography on silica eluting with isohexane: EtOAc (gradient of 0 to 10% EtOAc) afforded the title compound as an off-white powder.

1H NMR (400 MHz, DMSO-d6) δ 8.3 (1H, s), 5.8 (2H, s), 4.1 (3H, s), 3.6 (3H, s), 1.9 (6H, s).

Step 2: Methyl 3-(2,5-dimethyl-1H-pyrrol-1-yl)-6-hydroxy-5-(trifluoromethyl)picolinate Methyl 3-(2,5-dimethyl-1H-pyrrol-1-yl)-6-methoxy-5-(trifluoromethyl)picolinate (100 mg, 0.305 mmol) in acetonitrile (3.05 ml) was treated with KI (202 mg, 1.218 mmol) and TMS-Chloride (0.156 ml, 1.221 mmol) and heated at reflux for 6 hours. The solvent removed was in vacuo and the crude product was dissolved in EtOAc (20 ml) and washed with water (2×10 ml) and brine (10 ml), dried over a phase separator and concentrated in vacuo. Purification of the crude product by chromatography on silica eluting with iso-hexane: EtOAc (gradient of 0 to 30% EtOAc) afforded the title compound as an yellow powder. LC-MS Rt=1.11 mins [M+H]+ 315.4 (Method 2 min-LC_v003).

Step 3: Methyl 3-(2,5-dimethyl-1H-pyrrol-1-yl)-6-ethoxy-5-(trifluoromethyl)picolinate Methyl 3-(2,5-dimethyl-1H-pyrrol-1-yl)-6-hydroxy-5-(trifluoromethyl)picolinate (62 mg, 0.168 mmol) in 1,4-dioxane (1.5 ml) (dry) was treated with EtOH (0.020 ml, 0.335 mmol) and triphenylphosphine (88 mg, 0.335 mmol) and the solution stirred. DEAD (0.053 ml, 0.335 mmol) was added dropwise and the reaction mixture stirred at room temperature for 2 hours. The solvent was removed in vacuo and purification of the crude product by chromatography on silica eluting with iso-hexane: EtOAc (gradient of 0 to 10% EtOAc) afforded the title compound;

1H NMR (400 MHz, DMSO-d6) δ 8.3 (1H, s), 5.8 (2H, s), 4.5 (2H, q), 3.6 (3H, s), 1.9 (6H, s), 1.4 (3H, t).

Step 4: 3-(2,5-Dimethyl-1H-pyrrol-1-yl)-6-ethoxy-5-(trifluoromethyl)picolinic acid Methyl 3-(2,5-dimethyl-1H-pyrrol-1-yl)-6-ethoxy-5-(trifluoromethyl)picolinate (140 mg, 0.409 mmol) was dissolved in THF (2.045 ml). NaOH (0.613 ml, 1.226 mmol) was added and heated at reflux for 6 hours. The solvent was removed in vacuo and the resulting mixture was diluted with EtOAc (25 ml) was acidified to pH 1 using HCl (5M). The organic portion washed with brine, dried using a phase separator and concentrated in vacuo to afford the title compound as a yellow oil.

LC-MS Rt=1.26 mins [M+H]+ 329.2 Method 2 min-LC_v003.

Intermediate E

3 -Amino-5-trifluoromethyl-pyridine-2-carboxylic acid

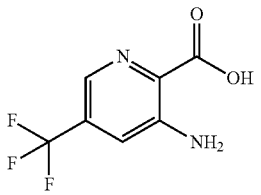

To a stirring solution of 3-Amino-5-trifluoromethyl-pyridine-2-carboxylic acid methyl ester (Intermediate A3) (1 g, 4.54 mmol) in MeOH (20 ml) was added 2M NaOH (0.182 g, 4.54 mmol). The orange solution was stirred at RT for 1 minute and then into water (10 ml). The solution was acidified to pH1 with the addition of 1M HCl and the product was extracted with EtOAc (150 ml). The organic portions were combined, washed with brine (50 ml), dried over $MgSO_4$ and concentrated in vacuo to afford the title compound as an orange solid; LC-MS Rt=0.82 mins [M+H]+ 207.1 (Method 2 minLC_v002); 1H NMR (400 MHz, DMSO-d6) δ 13.9 (1H, broad hump), 8.11 (1H, s), 7.59 (1H, s), 7.08 (2H, broad hump) (trace of EtOAc present but correlates to proposed structure).

Intermediate G

3-Amino-6-(4-fluoro-phenyl)-5-trifluoromethyl-pyridine-2-carboxylic acid

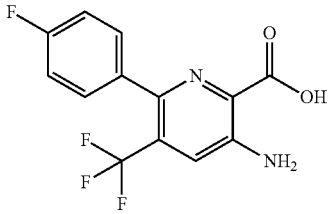

A mixture comprising 3-amino-6-bromo-5-trifluoromethyl-pyridine-2-carboxylic acid (Intermediate A) (1 g, 3.51 mmol), 4-fluorophenylboronic acid (0.736 g, 5.26 mmol) and 1,1'Bis(diphenylphosphoshio)ferrocene palladium dichloride (0.286 g, 0.351 mmol) and 1.0M $Cs_2CO_3$ (3.3 ml) in THF (10 ml) was heated to reflux for 10 hours. After cooling to RT, the mixture was partitioned between DCM (100 ml) and 1 M NaOH (2×100 ml). The aqueous phase was acidified with 5M HCl and the resulting milky solution was extracted into DCM (2×100 ml). The organic portion was separated, dried ($MgSO_4$) and concentrated in vacuo to afford the product as a crude oil. The crude material was purified by flash chromatography on silica cartridge eluting with a gradient of DCM: MeOH from 0% to 10% MeOH to afford the title product as a pale yellow solid;

1H NMR (DMSO-d6, 400 MHz) δ 12.9 (1H, br s, COOH), 7.7 (1H, s, CH, Ar—H), 7.4 (2H, m, Ar—H), 7.25 (2H, m, Ar—H), 7.1 (2H, br s, NH2).

Intermediate GA

3-Amino-6-cyclopropyl-5-(trifluoromethyl)picolinic acid

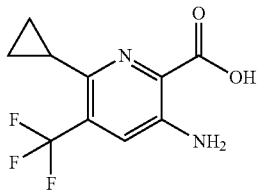

Step 1: 3-Amino-6-cyclopropyl-5-(trifluoromethyl) picolinic acid

A microwave vial was charged with amino-6-bromo-5-trifluoromethyl-pyridine-2-carboxylic acid methyl ester (Intermediate A4) (0.5 g, 1.754 mmol), cyclopropylboronic acid (0.753 g, 8.77 mmol), and 1,1'Bis(diphenylphosphosphino)ferrocene palladium dichloride (0.143 g, 0.175 mmol). The mixture was taken up as a solution in THF (6 ml) and flushed with $N_2$, sealed and heated using microwave radiation at 150° C. for 20 minutes. The reaction mixture was filtered through Celite® (filter material) and washed through with EtOAc (20 ml). The filtrate was partitioned between EtOAc (30 ml) and water (50 ml). The phases were separated and the organic portion was washed with brine (30 ml), dried over $MgSO_4$, filtered and concentrated under vacuum. The crude material was taken up in EtOAc (20 ml) and dry loaded onto silica (2-3 g). Material then purified on the Combiflash Rf Teledyne ISCO System 100% Isohexane to 60% EtOAc:Isohexane to afford semi pure material which was used without further purification.

Step 2: 3-Amino-6-cyclopropyl-5-(trifluoromethyl) picolinic acid

To a stirring solution of 3-amino-6-cyclopropyl-5-(trifluoromethyl)picolinic acid (472 mg, 1.814 mmol) in THF (10 ml), 2M NaOH (10 ml, 20.00 mmol) was added. The orange solution was stirred at RT for 2 days. The reaction mixture was poured into water (30 ml) and the pH adjusted to pH6 with the addition of 1M HCl. The product was extracted with EtOAc (50 ml) and the organic portion was dried over $MgSO_4$, filtered and concentrated in vacuo to give the title compound as a red/orange oil. LC-MS Rt=1.10 mins [M+H]+ 247.1 (Method 2 minLC_v003);

Intermediate H

3-Amino-6-(2,4-dichloro-phenyl)-5-trifluoromethyl-pyridine-2-carboxylic acid

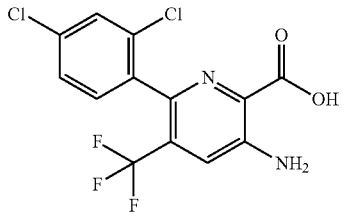

Intermediate H1: 3-Amino-6-(2,4-dichloro-phenyl)-5-trifluoromethyl-pyridine-2-carboxylic acid methyl ester 3-Amino-6-bromo-5-trifluoromethyl-pyridine-2-carboxylic acid methyl ester (Intermediate A4) (3 g, 10.03 mmol), 2,4-dichlorophenylboronic acid (2.297 g, 12.04 mmol), potassium phosphate (4.26 g, 20.06 mmol) and Fibre-cat® 1034A (Johnson Matthey, polymer supported palladium complex) (500 mg, 10.03 mmol) were suspended in toluene (50 ml) and water (15 ml). The reaction mixture was heated to 110° C. under vigorous stirring for 3 hours. The mixture was allowed to cool to RT and EtOAc (100 ml) was added. The organic layer was separated and washed with brine (15 ml). MP-TMT (macroporous polystyrene-bound trimercaptotriazine, 3 g, Polymern labs) was added and stirred for 1 hour at RT. $MgSO_4$ was added and the suspension filtered off. The filtrate was concentrated in vacuo and purification of the residue by reverse phase chromatography (130 g C18 column) eluting with water/MeOH afforded the title compound as a white solid; LS-MS Rt=1.55 mins [M+H]+ 365 (Method 2 minLC_v002).

Intermediate H: 3-Amino-6-(2,4-dichloro-phenyl)-5-trifluoromethyl-pyridine-2-carboxylic acid 3-Amino-6-(2,4-dichloro-phenyl)-5-trifluoromethyl-pyridine-2-carboxylic acid methyl ester (0.9 g, 2.465 mmol) was suspended in MeOH (15 ml) and NaOH 2M (2.465 ml, 4.93 mmol) was added under stirring. 1,4-Dioxane (15.00 ml) was added and the solution was left standing at RT over night. The solvent was removed in vacuo and the resulting residue was dissolved in water (10 ml) and carefully acidified to pH4 with slow addition of 2M HCl (2 ml) whilst stirring. The mixture was extracted with EtOAc (20 ml) and the organic portion was washed with brine and concentrated in vacuo. The residue was purified by reverse phase chromatography (130 g C18 column) eluting with water/MeOH to afford the title compound; LS-MS Rt=1.57 mins [M+H]+ 351.0 (Method 2 min LC_v002).

Intermediate I

3-Amino-6-(4-chloro-2-methyl-phenyl)-5-trifluoromethyl-pyridine-2-carboxylic acid

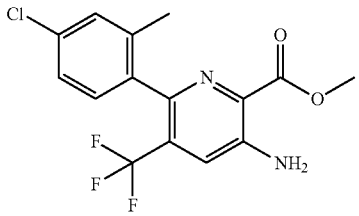

This compound was prepared from 3-Amino-6-bromo-5-trifluoromethyl-pyridine-2-carboxylic acid methyl ester (Intermediate A4) and 4-chloro-2-methylphenylboronic acid analogously to Intermediate H; LC-MS Rt=1.53 mins, [M+H]+ 331 (Method 2 min LC_v002).

Intermediate J

2-Aminomethyl-1,1,1,3,3,3-hexafluoro-propan-2-ol

To a stirred mixture of 35% ammonium solution (1 ml) and diethyl ether (1 ml) was added 3,3,3-trifluoro-2-(trifluoromethyl)-1,2-propenoxide (500 mg, 2.78 mmol) dropwise and the reaction mixture was left to stir at RT for 3 hours. The reaction mixture was separated and the aqueous layer was extracted with diethyl ether (2×3 ml). The combined organic portions were dried ($MgSO_4$) and concentrated in vacuo to give a white crystalline solid; 1H NMR (400 MHz, DMSO-d6) δ 4.20 (broad), 3.30 (broad), 3.15 (s), 3.02 (s), 2.50 (s, DMSO). $^{19}F$ NMR (400 MHz, DMSO-d6) δ −85 (CF3), −84.5 (CF3).

Intermediate K

5-Amino-6'-methyl-3-(trifluoromethyl)-2,3'-bipyridine-6-carboxylic acid

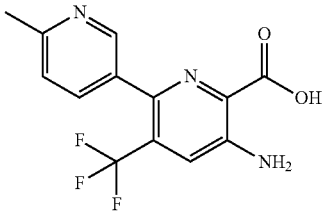

Intermediate K1: 5-Amino-6'-methyl-3-trifluoromethyl-[2,3']bipyridinyl-6-carboxylic acid methyl ester This compound was prepared from 3-Amino-6-bromo-5-trifluoromethyl-pyridine-2-carboxylic acid methyl ester (Intermediate A4) and 2-methylpyridine-5-boronic acid analogously to 3-amino-6-(4-fluoro-phenyl)-5-trifluoromethyl-pyridine-2-carboxylic acid (Intermediate G); LC-MS Rt 0.96 min [M+H]+ 312 (Method 2 minLC_v002); 1H NMR (400 MHz, DMSO-d6) δ 8.41 (1H, s), 7.79 (1H, s), 7.69 (1H, dd), 7.32 (1H, d), 7.10 (2H, s), 3.82 (3H, s), 2.52 (3H, s).

Intermediate K: 5-Amino-6'-methyl-3-(trifluoromethyl)-2,3'-bipyridine-6-carboxylic acid This compound was prepared from: 5-Amino-6'-methyl-3-trifluoromethyl-[2,3']bipyridinyl-6-carboxylic acid methyl ester analogously to 3-amino-6-(4-chloro-2-methyl-phenyl)-5-trifluoromethyl-pyridine-2-carboxylic acid methyl ester (Intermediate I); LC-MS Rt 0.90 min; [M+H]+ 298 (Method 2 minLC_v002); 1H NMR (400 MHz, DMSO-d6) δ 12.90 (1H, broad), 8.45 (1H, s), 7.72 (2H), 7.32 (1H, d), 7.12 (2H, broad), 2.51 (3H).

Intermediate KA

5-Amino-3-(trifluoromethyl)-2,4'-bipyridine-6-carboxylic acid

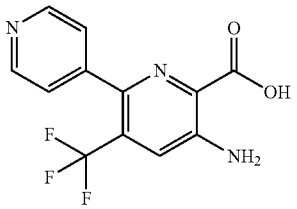

The title compound was prepared analogously to Intermediate K using the appropriate boronic acid in step 1; 1H NMR (400 MHz, DMSO-d6) δ 13.00 (1H, broad), 8.65 (2H, d), 7.65 (1H, s), 7.43 (2H, d), 7.18 (2H, broad).

Intermediate M 3-(2,5-Dimethyl-pyrrol-1-yl)-5,6-bis-trifluoromethyl-pyridine-2-carboxylic acid

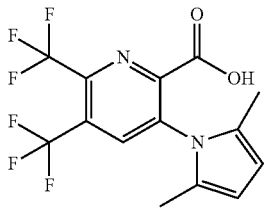

Intermediate M1: 3-(2,5-Dimethyl-pyrrol-1-yl)-5,6-bis-trifluoromethyl-pyridine-2-carboxylic acid methyl ester A stirred mixture of KF (2.12 g, 5.62 mmol) and CuI (0.490 g, 8.43 mmol) was heated in a sealed 10.0-20.0 ml microwave vial under vacuum until a slight greenish colour began to appear. The vial was then placed under nitrogen to cool. A solution 6-bromo-3-(2,5-dimethyl-pyrrol-1-yl)-5-trifluoromethyl-pyridine-2-carboxylic acid methyl ester (Intermediate D) (2.64 ml, 16.86 mmol) in 1:1 dry DMF/dry NMP (14 ml) was then added, followed by TMS-$CF_3$ (2.64 ml, 16.86 mmol). A new septum was then used to seal the vial and the reaction mixture was heated using microwave radiation with stirring at 100° C. for 3 h and allowed to cool. The mixture was added to 5M NH3 solution (50 ml) and then extracted with diethyl ether (4×50 ml). The combined organic extracts were washed with 5M $NH_3$ solution (3×20 ml), 1M HCl (50 ml), sat. sodium bicarbonate solution (2×50 ml), brine (50 ml), dried ($MgSO_4$) and concentrated in vacuo to give a brown oil. The crude material was purified by chromatography on silica eluting with Iso-hexane/EtOAc, 0-10% to afford the title compound as an orange solid; LC-MS Rt 1.37 min; MS m/z 367.1 [M+H]+; Method 2 minLC_v003.

Intermediate M: 3-(2,5-Dimethyl-pyrrol-1-yl)-5,6-bis-trifluoromethyl-pyridine-2-carboxylic acid To a stirred solution 3-(2,5-dimethyl-pyrrol-1-yl)-5,6-bis-trifluoromethyl-pyridine-2-carboxylic acid methyl ester (1.28 g, 3.49 mmol) in methanol (25 ml) was added 1M NaOH (7 ml, 6.99 mmol) and the reaction mixture was left to stir at RT for 30 min. The solvent was removed in vacuo and water (20 ml) was added to the remaining residue. The pH was adjusted to pH 4/5 by the addition of 1M HCl. The mixture was extracted with EtOAc (3×20 ml) and the combined organic extracts were washed with brine (30 ml), dried ($MgSO_4$) and concentrated in vacuo and dried in a vacuum oven (50° C.) overnight to give the crude title product as an orange solid which was used without further purification; LC-MS: Rt 1.23 min; MS m/z 353.1 [M+H]+; Method 2 minLC_v003.

Intermediate N 3,3,3-Trifluoro-N2-(4-methoxybenzyl)-2-methylpropane-1,2-diamine

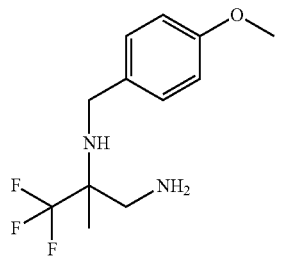

Step 1: 1-(4-methoxyphenyl)-N-(1,1,1-trifluoropropan-2-ylidene)methanamine

To a stirring solution of trifluoroacetone (7.75 g, 69.2 mmol) in diethyl ether (60 ml) at −40° C. was added 4-methoxybenzyl amine (9.49 g, 69.2 mmol) and triethylamine (14 g, 138 mmol) in diethyl ether (40 ml). A cooled (0° C.) mixture of $TiCl_4$ (6.56 g, 34.6 mmol) in hexane (40 ml) at was added dropwise over 10 minutes and the resulting mixture was allowed to warm up to ambient temperature over 20 mins and stirred at 50° C. for 2.5 h. The inorganic precipitate was removed by filtration and washed with diethyl ether. The filtrate was concentrated in vacuo to afford a yellow oil. Purification of the crude product by chromatography on silica eluting with 0% to 25% EtOAc in iso-hexane afforded the title product.

Step 2: 3,3,3-trifluoro-2-(4-methoxybenzylamino)-2-methyl propanenitrile

To a cooled (0° C.) solution of 1-(4-methoxyphenyl)-N-(1,1,1-trifluoropropan-2-ylidene)methanamine (4.41 g, 19.07 mmol) in DCM (100 ml) was added cyanotrimethylsilane (2.84 g, 28.6 mmol) and magnesium bromide. The mixture was stirred at RT for 90 h and then diluted with sat. $NaHCO_3$ (200 ml). After stirring at RT for 1 h, the organic phase was separated, washed with a further portion of sat. $NaHCO_3$ (100 ml), dried over $MgSO_4$ and concentrated in vacuo to afford the title compound.

Step 3: 3,3,3-trifluoro-N2-(4-methoxybenzyl)-2-methylpropane-1,2-diamine

To a cooled (0° C.) solution of 3,3,3-trifluoro-2-(4-methoxybenzylamino)-2-methyl propanenitrile (1.5 g, 5.81 mmol) in dry diether ether (50 ml) was added LiAlH4 (11.62 ml of a 2M solution in THF) and the resulting mixture was stirred at RT overnight. The reaction mixture was hydrolyzed by successive addition of water 15% KOH, and water. The resulting precipitate was filtered on Celite® (filter material) and the organic portion was washed with water, dried over $MgSO_4$ and concentrated under reduced pressure to afford the title product; 1H NMR (400 MHz, Methanol-d4) δ 7.97 (1H, s), 7.85 (1H, s), 7.60 (1H, s), 3.97 (3H, s), 3.77 (1H, m), 3.56 (1H, m), 1.37 (3H, s)

LC-MS: Rt 3.22 min; MS m/z 412.3 [M+H]+; Method 10 minLC_v003.

Intermediate O

Benzo[d]isoxazol-3-ylmethanamine

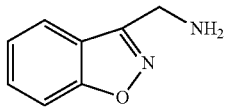

The title compound was prepared according to the procedure of Pigini, Maria; Giannella, Mario; Gualtieri, Fulvio; Melchiorre, Carlo; Bolle, Paola; Angelucci, Luciano. Analogs with a 1,2-benzisoxazole nucleus of biologically active indole derivatives. Ill. Tryptamine and gramine isosteres. European Journal of Medicinal Chemistry (1975), 10(1), 29-32 (Compound 11 page 31-32).

Intermediate P

Methyl 3-amino-6-(oxazol-2-yl)-5-(trifluoromethyl) picolinate

A solution of 3-amino-6-bromo-5-trifluoromethyl-pyridine-2-carboxylic acid methyl ester (Intermediate A4) (500 mg, 1.672 mmol), 2-(tributylstannyl)oxazole (0.704 ml, 3.34 mmol) and tetrakis(triphenylphosphine)palladium(0) (193 mg, 0.167 mmol) in dioxane (10 ml) was heated at reflux for 13 hours. After cooling to room temperature over 8 hours, the solvent was evaporated and the resulting residue triturated with hot methanol to remove a yellow solid impurity. The remaining crude material was used without further purification. LC-MS: Rt 0.95 min; MS m/z 288 [M+H]+; Method 2 minLC_v003.

Intermediate PA

3-Amino-6-furan-2-yl-5-trifluoromethyl-pyrazine-2-carboxylic acid

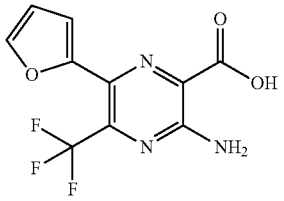

Step 1: 3-Amino-6-furan-2-yl-5-trifluoromethyl-pyrazine-2-carboxylic acid

The title compound was prepared from 3-amino-6-bromo-5-trifluoromethyl-pyrazine-2-carboxylic acid ethyl ester (Intermediate C1) and tributyltin-2-furylstannane analogously to methyl 3-amino-6-(oxazol-2-yl)-5-(trifluoromethyl)picolinate (Intermediate P)

Step 2: 3-Amino-6-furan-2-yl-5-trifluoromethyl-pyrazine-2-carboxylic acid

The title compound was prepared from 3-amino-6-furan-2-yl-5-trifluoromethyl-pyrazine-2-carboxylic acid and 6M NaOH analogously to 3-amino-6-bromo-5-trifluoromethyl-pyrazine-2-carboxylic acid (Intermediate C, final step).

Intermediate Q

2-Hydroxy-3-methyl-2-(trifluoromethyl)butan-1-aminium chloride

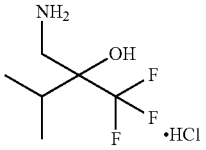

Step 1: 1,1,1-Trifluoro-3-methyl-2-(nitromethyl) butan-2-ol

A cooled (0° C.) solution of lithium hydroxide (0.048 g, 2.015 mmol) in water (20 ml) was stirred and treated with nitromethane (1.23 g, 20.15 mmol), 1,1,1-trifluoro-3-methylbutan-2-one (3.11 g, 22.17 mmol), cetyltrimethylammonium Chloride (0.871 g, 2.72 mmol) and $MgSO_4$ (0.485 g, 4.03 mmol). The white suspension was stirred at 0° C. for 1 hr, then at RT for 2 days. The resulting biphasic mixture was separated and the more dense lower layer was collected and dissolved in diethyl ether (30 ml). The mixture was dried over $MgSO_4$, filtered and concentrated in vacuo to give a pale yellow oil. The oil was taken up in diethyl ether (10 ml) and passed through a pre-packed SCX-2 cartridge eluting with 100% diethyl ether. The filtrate was concentrated in vacuo to afford the title compound as a colourless oil. $^1$H NMR (400 MHz, $CDCl_3$): δ 4.74 (1H, d), 4.59 (1H, d), 4.29 (1H, s), 2.29 (1H, m), 1.1 (6H, two sets of unresolved doublets)

Step 2: 2-Hydroxy-3-methyl-2-(trifluoromethyl) butan-1-aminium chloride

To a solution of 1,1,1-trifluoro-3-methyl-2-(nitromethyl) butan-2-ol (753 mg, 3.74 mmol) in EtOH (10 ml) in a 25 ml medium pressure glass hydrogenation vessel under $N_2$, 10% Pd on carbon (39.8 mg, 0.374 mmol) was added. The vessel was flushed with $N_2$, followed by $H_2$ (22.64 mg, 11.23 mmol) at 5 bar pressure and stirred at RT for 6 days. The mixture was filtered through Celite® and washed through with EtOH (30 ml), followed by DCM (10 ml). The filtrate was concentrated under vacuum to give a colourless oil. The crude product was taken up in methanol (20 ml) and treated with a 1.25M HCl in methanol solution. The resulting colourless solution was stirred at RT for 1 hour and concentrated under vacuum to afford the title compound;

1H NMR (400 MHz, DMSO-d6) δ 8.04 (3H, broad peak), 6.74 (1H, s), 3.58 (broad peak), 3.6 (2H, m), 2.12 (1H, m), 0.99 (6H).

Intermediate R

3-Amino-1,1,1-trifluoro-2-methylpropan-2-ol hydrochloride

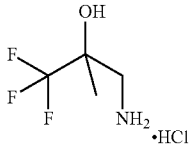

Step 1: 1,1,1-trifluoro-2-methyl-3-nitropropan-2-ol

To LiOH (0.193 g, 8.06 mmol) in a 3-neck roundbottom flask was added water (25 ml), nitromethane (3.76 ml, 81 mmol) and trifluoroacetone (7.95 ml, 89 mmol). Cetyltrimethylammonium chloride (3.8 g, 10.88 mmol) and $MgSO_4$ (1.9 g, 16.12 mmol) were added and the resulting yellow solution stirred at 20-25° C. for 2 days. The reaction mixture was poured into diethyl ether (120 ml) and washed with water (3×200 ml) and brine (1×100 ml). The organic portion was dried over $MgSO_4$ and concentrated in vacuo to afford the title compound as a yellow liquid. 1H NMR ($CDCl_3$, 400 MHz): δ 4.7 (1H d), δ 4.5 (1H, d), δ 3.7 (1H, broad), δ 1.6 (3H, s).

Step 2: 3-Amino-1,1,1-trifluoro-2-methylpropan-2-ol hydrochloride

Pd/C was added (1 g) to a 200 ml glass vessel. Ethanol (50 ml, dry) was added cautiously under an atmosphere of $CO_2$. 1,1,1-Trifluoro-2-methyl-3-nitropropan-2-ol (10 g, 57.8 mmol) was dissolved in ethanol (50 ml, dry) and added to the glass vessel. The reaction mixture was put under a positive pressure of hydrogen (5 bar) at room temperature and hydrogenated for 2 days. The reaction mixture was filtered through Celite® (filter material) and washed with excess ethanol. The solvent was removed in vacuo to yield a colourless oil. The oil was dissolved in MeOH (50 ml) and treated dropwise with HCl (1M) in MeOH (30 ml). The solution was left to stir for 30 minutes and concentrated in vacuo azeotroping with MeCN to afford the title compound as a waxy white solid; 1H NMR (DMSO-d6, 400 MHz) δ 8.3 (3H, broad s), 6.9 (1H, broad), 3.0 (2H, q), 1.4 (3H, s).

Intermediate RA (S)-3-Amino-1,1,1-trifluoro-2-methylpropan-2-ol hydrochloride

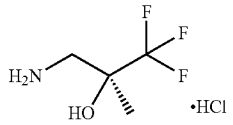

Step 1: Benzyl 3,3,3-trifluoro-2-hydroxy-2-methylpropylcarbamate

To a stirring suspension of amino-1,1,1-trifluoro-2-methylpropan-2-ol hydrochloride (Intermediate R) (1.5 g, 8.35 mmol) in DCM (50 ml) was added TEA 93.54 g, 35.0 mmol) followed by benzyl 2,5-dioxopyrrolidin-1-yl carbonate (1.983 g, 7.96 mmol). The mixture was stirred at RT for 6 hours and then diluted with water. The organic portion was separated using a phase separator and concentrated in vacuo. Purification by chromatography on silica eluting with 0-70% EtOAc in iso-hexane afforded the title product; 1H NMR (400 MHz, DMSO-d6) δ 7.34 (6H, m), 5.98 (1H, s), 5.05 (2H, s), 3.31 (1H, m), 3.18 (1H, m), 1.21 (3H, s) LC-MS: Rt 1.05 min; MS m/z 278.1 [M+H]+; Method 2 minLC_v003.

Step 2: Separation of Enantiomers of benzyl 3,3,3-trifluoro-2-hydroxy-2-methyl propylcarbamate Benzyl 3,3,3-trifluoro-2-hydroxy-2-methylpropylcarbamate (1.7 g) was dissolved in 2-propanol (10 ml) and purified using the following chromatographic conditions:

Mobile Phase: 10% 2-propanol/90% $CO_2$

Column: 2× Chiralcel OJ-H, 250×10 mm id, 5 μm (columns coupled in series)

Detection: UV@ 220 nm

Flow rate: 10 ml/min

Sample concentration: 1.7 g in 10 ml 2-propanol

Injection volume: 75 μl

First Eluted Peak:

Rt=6.94 minutes (R)-benzyl 3,3,3-trifluoro-2-hydroxy-2-methyl propylcarbamate

Second Eluted Peak:

Rt=8.04 minutes (S)-benzyl 3,3,3-trifluoro-2-hydroxy-2-methyl propylcarbamate (Stereochemistry confirmed by analysis of final compound prepared by subsequent steps)

Step 3: (S)-3-Amino-1,1,1-trifluoro-2-methylpropan-2-ol hydrochloride

A mixture comprising (S)-benzyl 3,3,3-trifluoro-2-hydroxy-2-methyl propylcarbamate in EtOH (165 ml) was pumped through a H-Cube (hydrogenation reactor, 1-2 ml/min, 1 bar pressure, RT) for 8 hours using a 10% palladium on carbon catalyst cartridge. 1.25 M HCl in methanol (130 ml) was added to the mixture was stirred for 30 mins. The solvent was removed in vacuo azeotroping with MeCN to afford the title product as a white powder; 1H NMR (400 MHz, DMSO-d6) δ 8.3 (3H, broad), 6.8 (1H, s), 3.0 (2H, s), 1.5 (3H, s).

Alternatively, racemic 3-Amino-1,1,1-trifluoro-2-methylpropan-2-ol can be resolved into separate enantiomers by recrystallistion with either (S)-Mandelic acid or L-tartaric acid in isopropanol or ethanol.

Intermediate S

2-Aminomethyl-1,1,1,3,3,3-hexafluoro-propan-2-ol 3,3,3-Trifluoro-2-(trifluoromethyl)-1,2-propenoxide (1 g, 5.55 mmol) was added to a stirred solution of aqueous ammonia solution (0.88 g/ml, 3 ml) and diethyl ether (3 ml). The resulting colourless solution was stirred at room temperature for 3 hours. The biphasic mixture was separated and the aqueous portion was further extracted with diethyl ether (2×5 ml). The combined organic layers were dried over $MgSO_4$ and concentrated in vacuo (no heating) to afford the title compound as a white crystalline solid which was used without further purification; 1H NMR (400 MHz, DMSO-d6) signals unassigned δ 4.20 (broad), 3.15 (s).

Intermediate T 3,3,3-Trifluoro-2-methoxy-2-methylpropan-1-amine

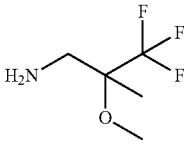

Step 1: 2-(3,3,3-Trifluoro-2-hydroxy-2-methylpropyl)isoindoline-1,3-dione

A mixture comprising 3,3,3-trifluoro-2-hydroxy-2-methyl-propyl-ammonium (0.9 g), phthalic anhydride (1.039 g) and DIPEA (2.188 ml) in chloroform (30 ml) was heated at 70° C. for 5 hours. After cooling to RT, the mixture was washed with water and passed through a phase separator. The organic phase was reduced to dryness. The crude product was purified by chromatography on silica, eluting in a 0% to 30% iso-hexane:EtOAc removed to give the title product; 1H NMR (400 MHz, Methanol-d4) δ 7.92 (2H, m), 7.85 (2H, m), 3.95 (2H, m), 1.36 (3H, s).

Step 2: 2-(3,3,3-Trifluoro-2-methoxy-2-methylpropyl)isoindoline-1,3-dione

To a stirring solution of 2-(3,3,3-trifluoro-2-hydroxy-2-methylpropyl)isoindoline-1,3-dione (250 mg, 0.915 mmol)) at 0° C. in THF (8 ml), NaH (80 mg, 2 mmol) was added. After 30 minutes methyl iodide (1.299, 9.15 mmol) was added. The reaction mixture was left stirring in a ice-bath and allowed to warm to 25° C. over 3.5 hours. The reaction was quenched with sat. $NH_4Cl$ and the mixture extracted with DCM. The organic extract was separated using a phase separator and purification by chromatography on silica, eluting in a 0% to 30% iso-hexane:EtOAc afforded the title product; 1H NMR (400 MHz, Methanol-d4) δ 7.91 (2H, m), 7.85 (2H, m). 3.97 (2H, m), 3.44 (3H, s), 1.42 (3H, s);

LC-MS: Rt 1.17 min; MS m/z 288.10 [M+H]+; Method 2 minLC_v003.

Step 3: 3,3,3-Trifluoro-2-methoxy-2-methylpropan-1-amine

A mixture comprising 2-(3,3,3-trifluoro-2-methoxy-2-methylpropyl)isoindoline-1,3-dione (272 mg, 0.95 mmol) and hydrazine (0.033 ml, 1.045 mmol) was stirred at 75° C. for 4 hours. After cooling to RT, the mixture was filtered and the filtrate was concentrated in vacuo to afford the title product which was used without further purification (no characterisation data available).

From the foregoing it will be appreciated that, although specific embodiments of the invention have been described herein for purposes of illustration, various modifications may be made without deviating from the spirit and scope of the invention. Accordingly, the invention is not limited except as by the appended claims.

EMBODIMENTS

Consistory Clauses

Embodiment 1

A compounds according to Formula I:

I

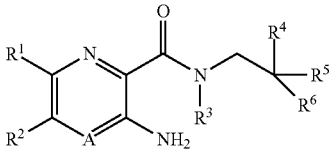

or pharmaceutically acceptable salts thereof, wherein:

A is N or $CR^{4a}$;

$R^1$ is H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; halogen; $SO_2NR^8R^9$; $SO_2R^{10}$; S—$C_1$-$C_8$alkyl optionally substituted by one or more halogen atoms; S—$C_6$-$C_{14}$ aryl; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; CN; $NR^{11}R^{12}$; $CONR^{13}R^{14}$; $NR^{13}SO_2R^{15}$; $NR^{13}C(O)R^{15}$ and $CO_2R^{15}$, wherein the cycloalkyl, cycloalkenyl, aryl and heterocyclyl groups are each optionally substituted by one or more Z substituents;

$R^2$ is $C_1$-$C_4$ haloalkyl;

$R^3$, $R^4$ and $R^{4a}$ are each independently H or $C_1$-$C_8$ alkyl optionally substituted by one or more halogen atoms;

$R^5$ and $R^6$ are each independently H; $C_1$-$C_8$ alkyl optionally substituted by one or more halogen atoms; $C_2$-$C_8$ alkenyl; $C_2$-$C_9$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; OH; CN; halogen; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; or —($C_0$-$C_4$ alkyl)-$CO_2R^{15}$, wherein the cycloalkyl, cycloalkenyl, —($C_0$-$C_4$ alkyl)-$C_6$-$C_{14}$ aryl and —($C_0$-$C_4$ alkyl)-3 to 14 membered heterocyclic group groups are each optionally substituted by one or more Z substituents; or $R^5$ and $R^6$ are each independently a group of the formula:

$$—(CH_2)_m—NR^{17}R^{18}; \text{ or}$$

$R^5$ and $R^6$ are each independently a group of the formula:

$$—(CH_2)_m—OR^4; \text{ or}$$

$R^4$ and $R^5$ together with the carbon atoms to which they are bound form a 3 to 8 membered carbocyclic ring system; or $R^5$ and $R^6$ together with the carbon atoms to which they are bound form a 5 to 8 membered carbocyclic ring system or a 5 to 8 membered heterocyclic ring system containing one or more heteroatoms selected from N, O and S, wherein the ring system is optionally substituted by one or more Z substituents;

$R^4$, $R^5$ and $R^6$ cannot all be the same;

m is 0, 1, 2 or 3;

$R^8$, $R^{11}$, $R^{13}$ and $R^{17}$ are each independently H, $C_1$-$C_8$ alkyl optionally substituted by one or more halogen atoms, $C_3$-$C_{10}$ cycloalkyl or —($C_1$-$C_4$ alkyl)-$C_3$-$C_8$ cycloalkyl;

$R^9$, $R^{10}$, $R^{12}$, $R^{14}$, $R^{15}$, $R^{16}$ and $R^{18}$ are each independently H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; —($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S, wherein the cycloalkyl, cycloalkenyl, aryl and heterocyclyl groups are each optionally substituted by one or more Z substituents; or $R^8$ and $R^9$, $R^{11}$ and $R^{12}$, $R^{13}$ and $R^{14}$, and $R^{17}$ and $R^{18}$ together with the nitrogen atom to which they are attached may form a 4 to 14 membered heterocyclic group optionally substituted by one or more Z substituents;

Z is independently OH, aryl, O-aryl, benzyl, O-benzyl, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups or $C_1$-$C_4$ alkoxy, $NR^{18}(SO_2)R^{21}$, $(SO_2)NR^{19}R^{21}$, $(SO_2)R^{21}$, $NR^{18}C(O)R^{21}$, $C(O)NR^{19}R^{21}$, $NR^{18}C(O)NR^{19}R^{21}$, $NR^{18}C(O)OR^{19}$, $NR^{19}R^{21}$, $C(O)OR^{19}$, $C(O)R^{19}$, $SR^{19}$, $OR^{19}$, oxo, CN, $NO_2$, halogen or a 3 to 14 membered heterocyclic group, wherein the heterocyclic group contains at least one heteroatom selected from N, O and S;

$R^{19}$ and $R^{21}$ are each independently H; $C_1$-$C_8$ alkyl; $C_3$-$C_8$ cycloalkyl; $C_1$-$C_4$alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclic group, the heterocyclic group including one or more heteroatoms selected from N, O and S, optionally substituted by one or more groups selected from halogen, oxo, $C_1$-$C_6$ alkyl and $C(O)C_1$-$C_6$ alkyl; ($C_0$-$C_4$ alkyl)-O-aryl optionally substituted by one or more groups selected from $C_1$-$C_6$ alkyl, $C_1$-$C_8$ alkoxy and halogen; and ($C_0$-$C_4$ alkyl)-O-3- to 14-membered heterocyclic group, the heterocyclic group including one or more heteroatoms selected from N, O and S, optionally substituted by one or more groups selected from halogen, $C_1$-$C_6$ alkyl or $C(O)C_1$-$C_6$ alkyl; wherein the alkyl groups are optionally substituted by one or more halogen atoms, $C_1$-$C_4$ alkoxy, $C(O)NH_2$, $C(O)NHC_1$-$C_6$ alkyl or $C(O)N(C_1$-$C_6$ alkyl$)_2$; or $R^{19}$ and $R^{21}$ together with the nitrogen atom to which they attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy.

Embodiment 2

The compound of Formula I

I

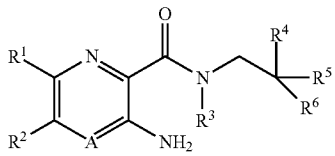

or pharmaceutically acceptable salts thereof, wherein:

A is N or $CR^{4a}$;

$R^1$ is H; $C_1$-$C_8$ alkyl optionally substituted by one or more halogen atoms; $C_2$-$C_6$ alkenyl; $C_2$-$C_6$ alkynyl; $C_3$-$C_{10}$ cycloalkyl; $C_5$-$C_{10}$ cycloalkenyl; $C_1$-$C_4$ alkyl-$C_3$-$C_8$ cycloalkyl; $C_1$-$C_8$ alkoxy optionally substituted by one or more halogen atoms; halogen; $SO_2NR^8R^9$; $SO_2R^{10}$; S—$C_1$-$C_8$alkyl optionally substituted by one or more halogen atoms; S—$C_6$-$C_{14}$ aryl; CN; $NR^{11}R^{12}$; $C(O)NR^{13}R^{14}$; $NR^{13}SO_2R^{15}$; $NR^{13}C(O)R^{15}$, $CO_2R^{15}$, —($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S; wherein the cycloalkyl, cycloalkenyl, aryl and heterocyclyl groups are each optionally substituted by one or more Z substituents;

$R^2$ is $C_1$-$C_4$ haloalkyl;

$R^3$ and $R^{4a}$ are each independently H or $C_1$-$C_8$ alkyl optionally substituted by one or more halogen atoms;

$R^4$ is H, or $C_1$-$C_8$ alkyl optional substituted with one or more halogen;

$R^5$ is —($CH_2$), —$NR^{17}R^{18}$, —$(CH_2)_m$—OR'; $C_1$-$C_8$ alkoxy optionally substituted by one or more halogen atoms; —($C_0$-$C_4$ alkyl)-$CO_2R^{15}$; —($C_0$-$C_4$ alkyl)-$C_6$-$C_{14}$ aryl or -3 to 14 membered heterocyclic group, wherein the heterocyclic group contains at least one heteroatom selected from N, O and S; wherein the —($C_0$-$C_4$ alkyl)-$C_6$-$C_{14}$ aryl and —($C_0$-$C_4$ alkyl)-3 to 14 membered heterocyclic group are each optionally substituted by one or more Z substituents;

$R^6$ is $C_1C_8$ alkyl optionally substituted by one or more halogen atoms; $C_3$-$C_{10}$ cycloalkyl; —$C_1$-$C_4$ alkyl-$C_3$-$C_8$ cycloalkyl; $C_1$-$C_8$ alkoxy optionally substituted by one or more halogen atoms; OH; CN; halogen; —($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S; wherein the cycloalkyl, cycloalkenyl, —($C_0$-$C_4$ alkyl)-$C_6$-$C_{14}$ aryl and —($C_0$-$C_4$ alkyl)-3 to 14 membered heterocyclic group are each optionally substituted by one or more Z substituents; or $R^6$ is H, and $R^5$ is —$(CH_2)_m$—$NR^{17}R^{18}$, —$(CH_2)_m$—OR', $C_1$-$C_8$ alkoxy optionally substituted by one or more halogen atoms; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; or —($C_0$-$C_4$ alkyl)-$CO_2R^{15}$, wherein —($C_0$-$C_4$ alkyl)-$C_8$-$C_{14}$ aryl and —($C_0$-$C_4$ alkyl)-3 to 14 membered heterocyclic group groups are each optionally substituted by one or more Z substituents; or $R^4$ and $R^6$ together with the carbon atoms to which they are bound form a 3 to 8 membered carbocyclic ring system; or $R^4$ and $R^5$ together form an oxo group (C—O) and $R^6$ is $C_1$-$C_4$ alkyl optionally substituted by one or more halogen atoms; $C_1$-$C_4$ alkoxy optionally substituted by one or more halogen atoms; ($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S, wherein the aryl and heterocyclyl groups are each optionally substituted by one or more Z substituents; or $R^5$ and $R^6$ together with the carbon atoms to which they are bound a 5 to 8 membered heterocyclic ring system containing one or more heteroatoms selected from N, O and S, wherein the ring system is optionally substituted by one or more Z substituents; or $R^4$ and $R^5$ and $R^6$ together with the carbon atoms to which they are bound form a 5 to 8 membered heterocyclic ring system containing one or more heteroatoms selected from N, O and S, wherein the ring system is optionally substituted by one or more Z substituents;

R' is H, or $C_1$-$C_8$ alkyl optional substituted with one or more halogen;

m is 0, 1, 2 or 3;

$R^8$, $R^{11}$, $R^{13}$ and $R^{17}$ are each independently H, $C_1$-$C_8$ alkyl optionally substituted by one or more halogen atoms, $C_3$-$C_{10}$ cycloalkyl or —($C_1$-$C_4$ alkyl)-$C_3$-$C_8$ cycloalkyl;

$R^9$, $R^{10}$, $R^{12}$, $R^{14}$, $R^{15}$, $R^{16}$ and $R^{18}$ are each independently H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; —($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S, wherein the cycloalkyl, cycloalkenyl, aryl and heterocyclyl groups are each optionally substituted by one or more Z substituents; or $R^8$ and $R^9$, $R^{11}$ and $R^{12}$, $R^{13}$ and $R^{14}$, and $R^{17}$ and $R^{18}$ together with the nitrogen atom to which they are attached may form a 4 to 14 membered heterocyclic group optionally substituted by one or more Z substituents;

Z is independently OH, aryl, O-aryl, benzyl, O-benzyl, $C_1$-$C_6$ alkyl optionally substituted by one or more OH groups or NH, groups, $C_1$-$C_6$ alkyl optionally substituted by one or more halogen atoms, $C_1$-$C_6$ alkoxy optionally substituted by one or more OH groups or $C_1$-$C_4$ alkoxy, $NR^{18}(SO_2)R^{21}$, $(SO_2)NR^{19}R^{21}$, $(SO_2)R^{21}$, $NR^{18}C(O)R^{21}$, $C(O)NR^{19}R^{21}$, $NR^{18}C(O)NR^{19}R^{21}$, $NR^{18}C(O)OR^{19}$, $NR^{19}R^{21}$, $C(O)OR^{19}$, $C(O)R^{19}$, $SR^{19}$, $OR^{19}$, oxo, CN, $NO_2$, halogen or a 3 to 14 membered heterocyclic group, wherein the heterocyclic group contains at least one heteroatom selected from N, O and S;

$R^{19}$ and $R^{21}$ are each independently H; $C_1$-$C_8$ alkyl; $C_3$-$C_8$ cycloalkyl: $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclic group, the heterocyclic group including one or more heteroatoms selected from N, O and S, optionally substituted by one or more groups selected from halogen, oxo, $C_1$-$C_6$ alkyl and $C(O)C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclic group, the heterocyclic group including one or more heteroatoms selected from N, O and S, optionally substituted by one or more groups selected from halogen, $C_1$-$C_6$ alkyl or $C(O)C_1$-$C_6$ alkyl; wherein the alkyl groups are optionally substituted by one or more halogen atoms, $C_1$-$C_4$ alkoxy, $C(O)NH_2$, $C(O)NHC_1$-$C_6$ alkyl or $C(O)N(C_1$-$C_6$ alkyl$)_2$; or $R^{19}$ and $R^{21}$ together with the nitrogen atom to which they attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; $S(O)_2$-aryl; $S(O)_2$—$C_1$-$C_6$alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy.

Embodiment 3

The compound according to embodiment 1 or 2, wherein $R^1$ is H; $C_1$-$C_4$ alkyl optionally substituted by one or more halogen atoms; $C_1$-$C_4$ alkoxy optionally substituted by one or more halogen atoms; halogen; $C_6$-$C_{14}$ aryl; —($C_0$-$C_4$ alkyl)-3 to 14 membered heterocyclic group, wherein the heterocyclic group contains at least one heteroatom selected from N, O and S; or —$NR^{11}R^{12}$, wherein the aryl and heterocyclic groups are each optionally substituted by one or more Z substituents.

Embodiment 4

The compound according to embodiment 1 to 3, wherein
$R^1$ is $C_1$-$C_4$ alkyl optional substituted by one or more halogen atoms.

Embodiment 5

The compound according to embodiment 1 to 4, wherein
$R^1$ is —$CH_3$ or $CF_3$.

Embodiment 6

The compound according to embodiment 1, 2 or 3, wherein
$R^1$ is $C_1$-$C_4$ alkoxy optional substituted by one or more halogen atoms.

Embodiment 7

The compound according to embodiment 1, 2, 3 or 6, wherein
$R^1$ is —$OCH_3$, —$OCH_2CH_3$ or —$OCF_3$.

Embodiment 8

The compound according to embodiments 1, 2 or 3, wherein $R^1$ is aryl, wherein aryl is phenyl optionally substituted by one or more Z substituents, Embodiment 9

The compound according to embodiment 1, 2, 3 or 8, wherein $R^1$ is 4-fluorophenyl, 4-chloro-2-methylphenyl, or 2,4-dichlorophenyl.

Embodiment 10

The compound according to embodiment 1, 2 or 3, wherein $R^1$ is pyridyl, oxazole, pyrrolidine or pyrazole and is optionally substituted by one or more Z substituents.

Embodiment 11

The compound according to embodiment 1, 2, 3 or 10, wherein $R^1$ is 1-methyl-4-pyridyl, oxzaoyl-2-yl, 1-methyl-1H-pyrazole-4-yl or pyrrolidin- 1yl.

Embodiment 12

The compound according to embodiment 1 to 11, wherein $R^1$ is Br, —$CH_3$, —$CF_3$, —$OCH_3$, —$OCH_2CH_3$, —$OCF_3$, 4-fluorophenyl, 4-chloro-2-methylphenyl, 2,4-dichlorophenyl, 1-methyl-4-pyridyl, 1-methyl-1H-pyrazole-4-yl, oxzaoyl-2-yl, or pyrrolidin-1-yl.

Embodiment 13

The compound according to embodiment 1 to 12, wherein $R^5$ provides a heteroatom two carbons from the amide nitrogen, wherein the heteroatom is oxygen or nitrogen.

Embodiment 14

The compound according to embodiment 1 to 13, wherein
$R^4$ is H or $C_1$-$C_4$ alkyl optionally substituted by one or more halogen atoms;
$R^5$ is $C_1$-$C_4$ alkoxy optionally substituted by one or more halogen atoms; —$(CH_2)_m$—$NR^{17}R^{18}$; —$(CH_2)_m$—OR', or OH;
R' is H, or $C_1$-$C_4$ alkyl optional substituted with one or more halogen;
m is 0, 1 or 2;
$R^6$ is $C_1$-$C_4$ alkyl optionally substituted by one or more halogen atoms; $C_1$-$C_4$ alkoxy optionally substituted by one or more halogen atoms; OH; CN; halogen; —($C_0$-$C_4$ alkyl)-$C_6$ aryl; or —($C_0$-$C_4$ alkyl)-5 to 6 membered heterocyclic group, wherein the heterocyclic group contains at least one heteroatom selected from N, O and S, wherein the aryl and heterocyclyl groups are each optionally substituted by one or more Z substituents; or
$R^4$ and $R^6$ together with the carbon atoms to which they are bound form a 3 to 8 membered carbocyclic ring system; or
$R^5$ and $R^6$ together with the carbon atoms to which they are bound a 5 to 8 membered heterocyclic ring system containing one or more heteroatoms selected from N, O and S, wherein the ring system is optionally substituted by one or more Z substituents;
$R^{17}$ and $R^{18}$ are each independently H; or $C_1$-$C_4$ alkyl optionally substituted by one or more halogen atoms.

Embodiment 15

The compound according to any proceeding embodiment, wherein
$R^3$ is H;
$R^4$ is H or Me;
$R^{4a}$ is H;
$R^5$ is —$(CH_2)_m$—$NR^{17}R^{18}$; —$(CH_2)_m$—OR'; or OH;
m is 0, or 1;
R' is H;
$R^6$ is $C_1$-$C_4$ alkyl optionally substituted by one or more halogen atoms; or
$R^5$ and $R^6$ together with the carbon atoms to which they are bound form a 5 to 6 membered heterocyclic ring system containing one or more heteroatoms selected from N, O and S, wherein the ring system is optionally substituted by one or more Z substituents; and
$R^{17}$ and $R^{18}$ are each independently H; or $C_1$-$C_4$ alkyl optionally substituted by one or more halogen atoms.

Embodiment 16

The compound according to any proceeding embodiment, wherein
$R^3$ is H;
$R^4$ is H or Me;
$R^{4a}$ is H;
$R^5$ is —$NR^{17}R^{18}$; or OH;
$R^6$ is $C_1$-$C_4$ alkyl optionally substituted by one or more halogen atoms; or
$R^5$ and $R^6$ together with the carbon atoms to which they are bound form a 5 to 6 membered heterocyclic ring system containing one or more heteroatoms selected from N, O and S, wherein the ring system is optionally substituted by one or more Z substituents; and
$R^{17}$ and $R^{18}$ are each independently H; or $C_1$-$C_4$ alkyl optionally substituted by one or more halogen atoms.

Embodiment 17

The compound according to any proceeding claim, wherein
$R^3$ is H;
$R^4$ is H or Me;
$R^{4a}$ is H;
$R^5$ is —$NR^{17}R^{18}$, or OH;

$R^6$ is $C_1$-$C_4$ alkyl optionally substituted by one or more halogen atoms; and $R^{17}$ and $R^{18}$ are each independently H; or $C_1$-$C_4$ alkyl optionally substituted by one or more halogen atoms.

Embodiment 18

The compound according to embodiment 1 to 13, wherein $R^3$ is H;

$R^{4a}$ is H;

$R^4$ and $R^5$ form an oxo group;

$R^6$ is $C_1$-$C_4$ alkyl optionally substituted by one or more halogen atoms; $C_1$-$C_4$ alkoxy optionally substituted by one or more halogen atoms; phenyl; or 5 to 6 membered heterocyclic group, wherein the heterocyclic group contains at least one heteroatom selected from N, O and S, wherein the phenyl and heterocyclyl groups are each optionally substituted by one or more Z substituents.

Embodiment 19

The compound according to embodiment 1 to 13 or 18, wherein $R^3$ is H;

$R^{4a}$ is H;

$R^4$ and $R^5$ form an oxo group;

$R^6$ is $C_1$-$C_4$ alkyl optionally substituted by one or more halogen atoms; or phenyl, wherein the phenyl is optionally substituted by one or more Z substituents;

Z is independently OH, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $C(O)OR^{19}$, $C(O)R^{19}$, $OR^{19}$, CN, or halogen;

$R^{19}$ is H; $C_1$-$C_4$ alkyl; $C_3$-$C_6$ cycloalkyl; or $C_1$-$C_4$ alkoxy-$C_1$-$C_4$ alkyl, wherein all alkyl are optionally substituted with halogens.

Embodiment 20

The compound according to embodiment 1 to 13 or 18 to 19, wherein $R^3$ is H;

$R^{4a}$ is H;

$R^4$ and $R^5$ form an oxo group;

$R^6$ is $C_1$-$C_4$ alkyl optionally substituted by one or more halogen atoms; or phenyl, wherein the phenyl is optionally substituted by one or more Z substituents;

Z is independently, $C_1$-$C_4$ alkyl optionally substituted by one or more halogen atoms, $C_1$-$C_4$ alkoxy or halogen.

Embodiment 21

The compound according to embodiment 1 to 13, wherein the compound is represented by formula II,

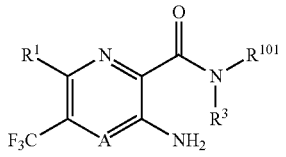

II or a pharmaceutically acceptable salt thereof, wherein, $R^{101}$ is selected from the following:

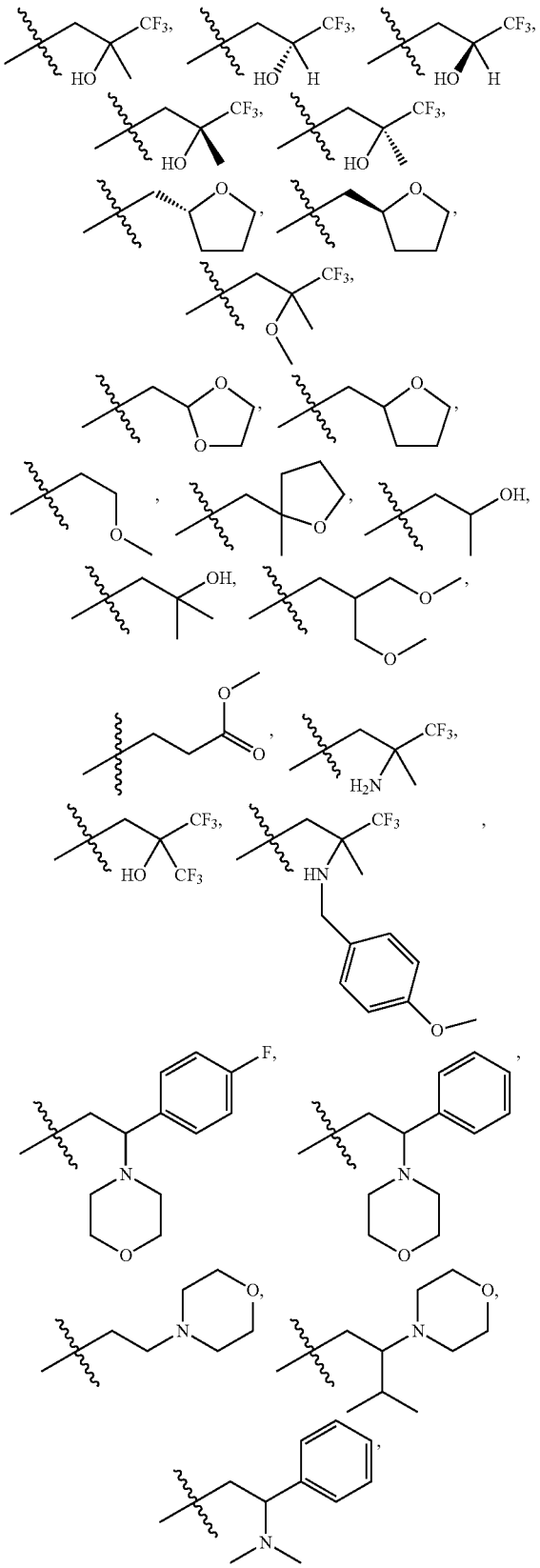

-continued
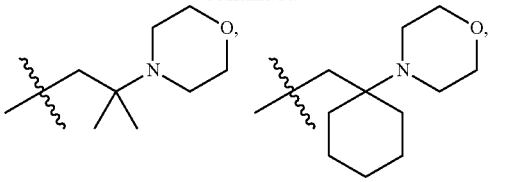
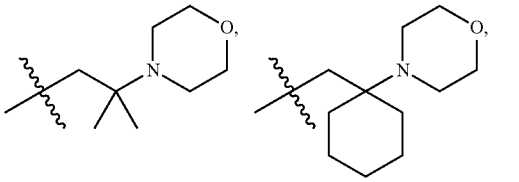
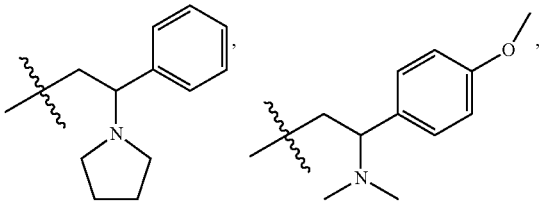
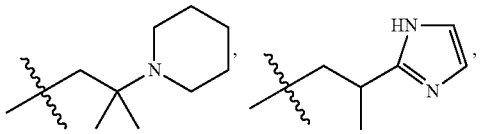
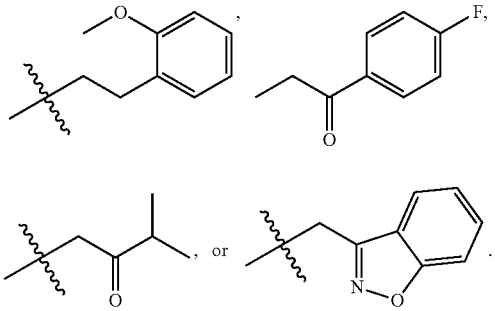
Embodiment 22
The compound according to embodiment 21, wherein
$R^3$ is H;
$R^{101}$ is
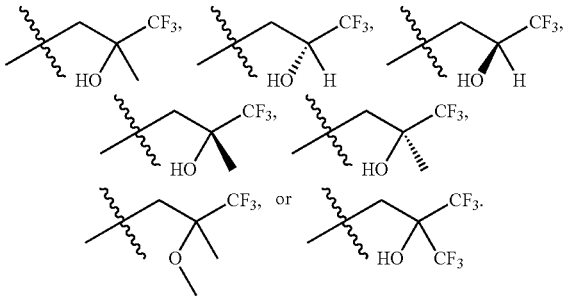
Embodiment 23
The compound according to embodiment 21, wherein
$R^3$ is H;
$R^{101}$ is
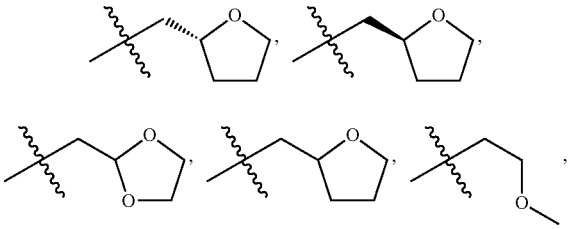
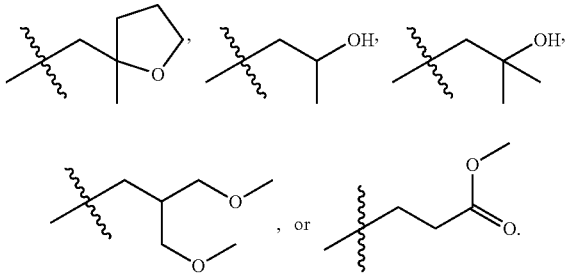
Embodiment 24
The compound according to embodiment 21, wherein
$R^3$ is H;
$R^{101}$ is
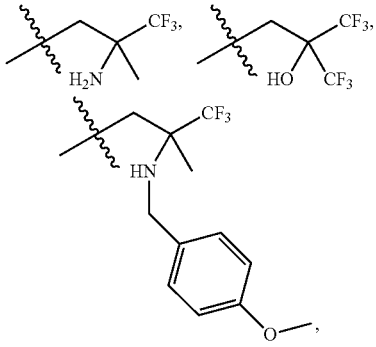
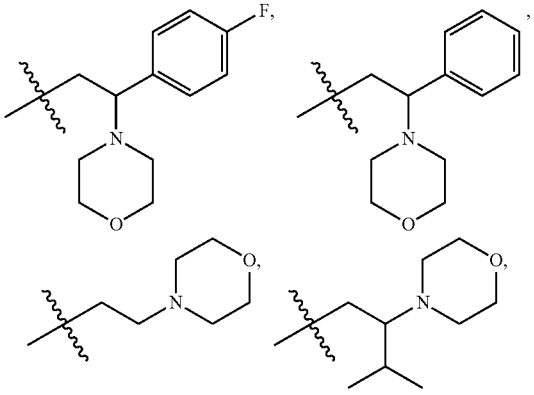

-continued

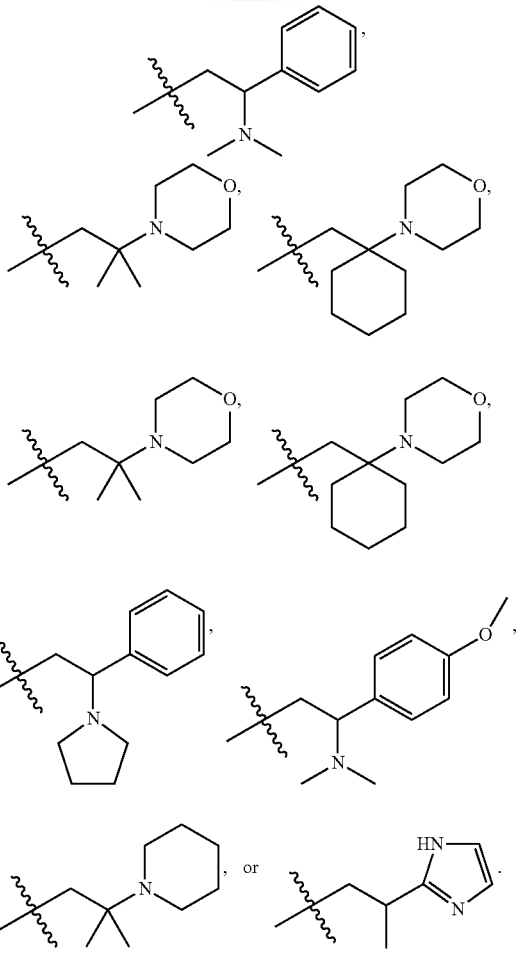

Embodiment 25

The compound according to embodiment 21, wherein
$R^3$ is H;
$R^{101}$ is

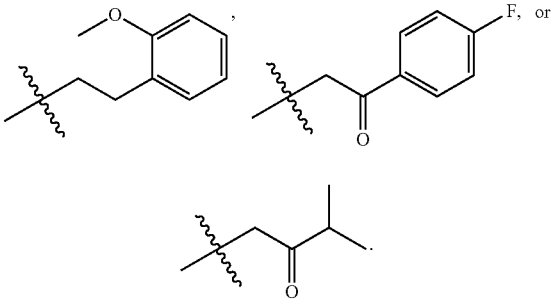

Embodiment 26

The compound according to embodiment 1 to 13, wherein
$R^3$ is H;
$R^{101}$ is —($C_1$-$C_2$ ($C_1$-$C_2$ alkyl)-5 to 10 membered heterocyclic group, wherein the heterocyclic group contains at least one heteroatom selected from N, O and S, wherein the aryl and heterocyclyl groups are each optionally substituted by one or more Z substituents.

Embodiment 27

The compound according to embodiment 21 or 26, wherein
$R^3$ is H;
$R^{101}$ is

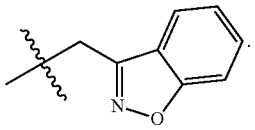

Embodiment 28

The compound of formula III

III

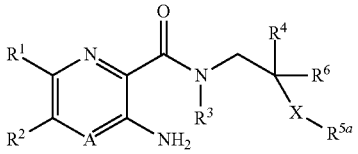

or pharmaceutically acceptable salts thereof, wherein:
A is N or $CR^{4a}$;
X is $NR_y$ or O;
$R^1$ is $C_1$-$C_8$ alkyl optionally substituted by one or more halogen atoms; $C_3$-$C_{10}$ cycloalkyl; —$C_1$-$C_4$ alkyl-$C_3$-$C_8$ cycloalkyl; $C_1$-$C_8$ alkoxy optionally substituted by one or more halogen atoms; halogen; CN; $NR^{11}R^{12}$; $C(O)NR^{13}R^{14}$; $NR^{13}C(O)R^{15}$, $CO_2R^{15}$, —($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S; wherein the cycloalkyl, aryl and heterocyclyl groups are each optionally substituted by one or more Z substituents;
$R^2$ is $C_1$-$C_4$ haloalkyl;
$R^3$ and $R^{4a}$ are each independently H or $C_1$-$C_8$ alkyl optionally substituted by one or more halogen atoms;
$R^4$ is H, or $C_1$-$C_8$ alkyl optional substituted with one or more halogen;
$R^{5a}$ is H, $C_1$-$C_8$ alkyl optional substituted with one or more halogen, —($C_0$-$C_4$ alkyl)-$C_6$-$C_{14}$ aryl or -3 to 14 membered heterocyclic group, wherein the heterocyclic group contains at least one heteroatom selected from N, O and S; wherein the —($C_0$-$C_4$ alkyl)-$C_6$-$C_{14}$ aryl and —($C_0$-$C_4$ alkyl)-3 to 14 membered heterocyclic group are each optionally substituted by one or more Z substituents;
$R^y$ is H, $C_1$-$C_8$ alkyl optional substituted with one or more halogen, —($C_0$-$C_4$ alkyl)-$C_6$-$C_{14}$ aryl or -3 to 14 membered heterocyclic group, wherein the heterocyclic group contains at least one heteroatom selected from N, O and S; wherein the —($C_0$-$C_4$ alkyl)-$C_6$-$C_{14}$ aryl and —($C_0$-$C_4$ alkyl)-3 to 14 membered heterocyclic group are each optionally substituted by one or more Z substituents;
$R^6$ is $C_1$-$C_8$ alkyl optionally substituted by one or more halogen atoms; $C_3$-$C_{10}$ cycloalkyl; —$C_1$-$C_4$ alkyl-$C_3$-$C_8$ cycloalkyl; $C_1$-$C_8$ alkoxy optionally substituted by one or more halogen atoms; OH; CN; halogen; —($C_0$-$C_4$ alkyl)-

$C_6$-$C_{14}$ aryl; or —($C_0$-$C_4$ alkyl)-3 to 14 membered heterocyclic group, wherein the heterocyclic group contains at least one heteroatom selected from N, O and S; wherein the cycloalkyl, cycloalkenyl, —($C_0$-$C_4$ alkyl)-$C_6$-$C_{14}$ aryl and —($C_0$-$C_4$ alkyl)-3 to 14 membered heterocyclic group are each optionally substituted by one or more Z substituents; or $R^4$ and $R^6$ together with the carbon atoms to which they are bound form a 3 to 8 membered carbocyclic ring system; or $R^{5a}$ and $R^6$ together with the atoms to which they are bound a 5 to 8 membered heterocyclic ring system containing one or more heteroatoms selected from N, O and S, wherein the ring system is optionally substituted by one or more Z substituents; or $R^{5a}$ and $R^y$ together with the atoms to which they are bound a 5 to 8 membered heterocyclic ring system containing one or more heteroatoms selected from N, O and S, wherein the ring system is optionally substituted by one or more Z substituents;

$R^{11}$ and $R^{13}$ are each independently H, $C_1$-$C_8$ alkyl optionally substituted by one or more halogen atoms, $C_3$-$C_{10}$ cycloalkyl or —($C_1$-$C_4$ alkyl)-$C_3$-$C_8$ cycloalkyl;

$R^{12}$, $R^{14}$, and $R^{15}$ are each independently H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; —($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S, wherein the cycloalkyl, cycloalkenyl, aryl and heterocyclyl groups are each optionally substituted by one or more Z substituents; or $R^{11}$ and $R^{12}$, and $R^{13}$ and $R^{14}$ together with the nitrogen atom to which they are attached may form a 4 to 14 membered heterocyclic group optionally substituted by one or more Z substituents;

Z is independently OH, aryl, O-aryl, benzyl, O-benzyl, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups or $C_1$-$C_4$ alkoxy, $NR^{18}(SO_2)R^{21}$, $(SO_2)NR^{19}R^{21}$, $(SO_2)R^{21}$, $NR^{18}C(O)R^{21}$, $C(O)NR^{19}R^{21}$, $NR^{18}C(O)NR^{19}R^{21}$, $NR^{18}C(O)OR^{19}$, $NR^{19}R^{21}$, $C(O)OR^{19}$, $C(O)R^{19}$, $SR^{19}$, $OR^{19}$, oxo, CN, $NO_2$, halogen or a 3 to 14 membered heterocyclic group, wherein the heterocyclic group contains at least one heteroatom selected from N, O and S;

$R^{19}$ and $R^{21}$ are each independently H; $C_1$-$C_8$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclic group, the heterocyclic group including one or more heteroatoms selected from N, O and S, optionally substituted by one or more groups selected from halogen, oxo, $C_1$-$C_6$ alkyl and $C(O)C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclic group, the heterocyclic group including one or more heteroatoms selected from N, O and S, optionally substituted by one or more groups selected from halogen, $C_1$-$C_6$ alkyl or $C(O)C_1$-$C_6$ alkyl; wherein the alkyl groups are optionally substituted by one or more halogen atoms, $C_1$-$C_4$ alkoxy, C(O)N $C(O)NHC_1$-$C_6$ alkyl or $C(O)N(C_1$-$C_6$ alkyl$)_2$; or $R^{19}$ and $R^{21}$ together with the nitrogen atom to which they attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy.

Embodiment 29

The compound according to embodiment 28, wherein

A is N or $CR^{4a}$;

X is $NR_y$ or O;

$R^1$ is alkyl optionally substituted by one or more halogen atoms; $C_1$-$C_4$ alkoxy optionally substituted by one or more halogen atoms; halogen; —($C_0$-$C_4$ alkyl)-$C_6$ aryl; or —($C_0$-$C_4$ alkyl)-5 to 6 membered heterocyclic group, wherein the heterocyclic group contains at least one heteroatom selected from N, O and S; wherein the cycloalkyl, aryl and heterocyclyl groups are each optionally substituted by one or more Z substituents;

$R^2$ is $C_1$-$C_4$ haloalkyl;

$R^3$ and $R^{4a}$ are H;

$R^4$ is H, or $C_1$-$C_4$ alkyl optional substituted with one or more halogen;

$R^{5a}$ is H, $C_1$-$C_4$ alkyl optional substituted with one or more halogen, —($C_0$-$C_4$ alkyl)-$C_6$ aryl or -5 to 8 membered heterocyclic group, wherein the heterocyclic group contains at least one heteroatom selected from N, O and S; wherein the —($C_0$-$C_4$ alkyl)-$C_6$ aryl and -5 to 8 membered heterocyclic group are each optionally substituted by one or more Z substituents;

$R^y$ is H, $C_1$-$C_4$ alkyl optional substituted with one or more halogen, —($C_0$-$C_4$ alkyl)-$C_6$ aryl or -5 to 8 membered heterocyclic group, wherein the heterocyclic group contains at least one heteroatom selected from N, O and S; wherein the —($C_0$-$C_4$ alkyl)-$C_6$ aryl and -5 to 8 membered heterocyclic group are each optionally substituted by one or more Z substituents;

$R^6$ is $C_1$-$C_4$ alkyl optionally substituted by one or more halogen atoms; $C_1$-$C_4$ alkoxy optionally substituted by one or more halogen atoms; OH; CN; —($C_0$-$C_4$ alkyl)-$C_6$ aryl; or -5 to 8 membered heterocyclic group, wherein the heterocyclic group contains at least one heteroatom selected from N, O and S; wherein the —$C_6$ aryl and -5 to 8 membered heterocyclic group are each optionally substituted by one or more Z substituents; or $R^4$ and $R^6$ together with the carbon atoms to which they are bound form a 3 to 8 membered carbocyclic ring system; or $R^{5a}$ and $R^6$ together with the atoms to which they are bound a 5 to 8 membered heterocyclic group containing one or more heteroatoms selected from N, O and S, wherein the heterocyclic group is optionally substituted by one or more Z substituents; or $R^{5a}$ and $R^y$ together with the atoms to which they are bound a 5 to 8 membered heterocyclic ring system containing one or more heteroatoms selected from N, O and S, wherein the ring system is optionally substituted by one or more Z substituents;

Z is independently OH, aryl, O-aryl, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups or $C_1$-$C_4$ alkoxy, $NR^{18}C(O)R^{21}$, $C(O)NR^{19}R^{21}$, $NR^{19}R^{21}$, $C(O)OR^{19}$, $C(O)R^{19}$, $SR^{19}$, $OR^{19}$, oxo, CN, $NO_2$, halogen or a 5 to 8 membered heterocyclic group, wherein the heterocyclic group contains at least one heteroatom selected from N, O and S; wherein the heterocyclic group is option substituted by halogen, $C_1$-$C_4$ alkyl optionally substituted by halogen, $C_1$-$C_4$ alkoxy or —CN;

$R^{18}$ is H or $C_1$-$C_4$ alkyl;

$R^{19}$ and $R^{21}$ are each independently H; $C_1$-$C_8$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclic group, the heterocyclic group including one or more heteroatoms selected from N, O and S, optionally substituted by one or more groups selected from halogen, oxo, $C_1$-$C_6$ alkyl and C(O)$C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclic group, the heterocyclic group including one or more heteroatoms selected from N, O and S, optionally substituted by one or more groups selected from halogen, $C_1$-$C_6$ alkyl or C(O)$C_1$-$C_6$ alkyl; wherein the alkyl groups are optionally substituted by one or more halogen atoms, $C_1$-$C_4$ alkoxy, C(O)N C(O)NH$C_1$-$C_6$ alkyl or C(O)N($C_1$-$C_6$ alkyl)$_2$; or $R^{19}$ and $R^{21}$ together with the nitrogen atom to which they attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; S(O)$_2$-aryl; S(O)$_2$—$C_1$-$C_6$ alkyl: $C_1$-$C_6$ alkyl optionally substituted by one or more halogen atoms; $C_1$-$C_6$ alkoxy optionally substituted by one or more OH groups or $C_1$-$C_4$ alkoxy; and C(O)O$C_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy.

Embodiment 30

The compound according to embodiment 28 or 29, wherein

A is N or $CR^{4a}$;

X is $NR^y$ or O;

$R^1$ is $C_1$-$C_4$ alkyl optionally substituted by one or more halogen atoms; $C_1$-$C_4$ alkoxy optionally substituted by one or more halogen atoms; or halogen;

$R^2$ is $CF_3$;

$R^3$ and $R^{4a}$ are H;

$R^4$ is H, or $C_1$-$C_4$ alkyl optional substituted with one or more halogen;

$R^{5a}$ is H, $C_1$-$C_4$ alkyl optional substituted with one or more halogen, $R^y$ is H, $C_1$-$C_4$ alkyl optional substituted with one or more halogen, $R^6$ is $C_1$-$C_4$ alkyl optionally substituted by one or more halogen atoms; $C_1$-$C_4$ alkoxy optionally substituted by one or more halogen atoms; OH; CN; or $R^4$ and $R^6$ together with the carbon atoms to which they are bound form a 3 to 6 membered carbocyclic ring system; or $R^{5a}$ and $R^6$ together with the atoms to which they are bound a 5 to 8 membered heterocyclic group containing one or more heteroatoms selected from N, O and S, wherein the heterocyclic group is optionally substituted by one or more Z substituents; or $R^{5a}$ and $R^y$ together with the atoms to which they are bound a 5 to 8 membered heterocyclic ring system containing one or more heteroatoms selected from N, O and S, wherein the ring system is optionally substituted by one or more Z substituents;

Z is independently OH, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups or $C_1$-$C_4$ alkoxy, $NR^{19}R^{21}$, C(O)O$R^{19}$, C(O)$R^{19}$, S$R^{19}$, O$R^{19}$, oxo, CN, $NO_2$, or halogen;

$R^{19}$ is H: $C_1$-$C_8$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclic group, the heterocyclic group including one or more heteroatoms selected from N, O and S, optionally substituted by one or more groups selected from halogen, oxo, $C_1$-$C_6$ alkyl and C(O)$C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclic group, the heterocyclic group including one or more heteroatoms selected from N, O and S, optionally substituted by one or more groups selected from halogen, $C_1$-$C_6$ alkyl or C(O)$C_1$-$C_6$ alkyl; wherein the alkyl groups are optionally substituted by one or more halogen atoms, $C_1$-$C_4$ alkoxy, C(O)$NH_2$, C(O)NH$C_1$-$C_6$ alkyl or C(O)N($C_1$-$C_6$ alkyl)$_2$; or $R^{19}$ and $R^{21}$ together with the nitrogen atom to which they attached form a 5- to 6-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; S(O)$_2$-aryl; S(O)$_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and C(O)O$C_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy.

Embodiment 31

The compound according to embodiment 28 to 30, wherein

A is N or $CR^{4a}$;

X is $NR^y$ or O;

$R^1$ is $C_1$-$C_4$ alkyl optionally substituted by one or more halogen atoms; $C_1$-$C_4$ alkoxy optionally substituted by one or more halogen atoms; or halogen;

$R^2$ is $CF_3$;

$R^3$ and $R^{4a}$ are H;

$R^4$ is H, or $C_1$-$C_4$ alkyl optional substituted with one or more halogen;

$R^{5a}$ is H, $C_1$-$C_4$ alkyl optional substituted with one or more halogen, $R^y$ is H, $C_1$-$C_4$ alkyl optional substituted with one or more halogen, $R^6$ is $C_1$-$C_4$ alkyl optionally substituted by one or more halogen atoms; $C_1$-$C_4$ alkoxy optionally substituted by one or more halogen atoms; OH; CN; or $R^{5a}$ and $R^6$ together with the atoms to which they are bound a 5 to 8 membered heterocyclic group containing one or more heteroatoms selected from N, O and S, wherein the heterocyclic group is optionally substituted by one or more Z substituents; or $R^{5a}$ and $R^y$ together with the atoms to which they are bound a 5 to 8 membered heterocyclic ring system containing one or more heteroatoms selected from N, O and S, wherein the ring system is optionally substituted by one or more Z substituents;

Z is independently OH, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups or $C_1$-$C_4$ alkoxy, oxo, CN, $NO_2$, or halogen;

Embodiment 32

The compound according to any of the proceeding embodiments, A is N.

Embodiment 33

The compound to embodiments 1 to 31, wherein A is $CR^{4a}$.

Embodiment 34

The compound according to embodiment 33, wherein A is $CR^{4a}$ and $R^{4a}$ is H.

Embodiment 35

The compound according to any proceeding embodiment, wherein $R^2$ is $CF_3CF_2$—, $(CF_3)_2CH$—, $CH_3$—$CF_2$—, $CF_3CF_2$—, $CF_3$, $CF_2H$—, $CH_3$—$CCl_2$—, $CF_3CFCClH$—, $CBr_3$, $CBr_2H$—$CF_3CF_2CHCF_3$ or $CF_3CF_2CF_2CF_2$—.

Embodiment 36

The compound according to any proceeding embodiment, wherein $R^2$ is $CF_3$.

Embodiment 37

The compound according to any proceeding embodiment, wherein the compound is a substantially pure enantiomer with the S configuration.

Embodiment 38

The compound according to embodiment 1 to 36, wherein the compound is a substantially pure enantiomer with the R configuration.

Embodiment 39

The compound according to embodiment 2, 21 or 28, wherein the compound is represented by:

3-Amino-6-bromo-5-trifluoromethyl-pyridine-2-carboxylic acid (3,3,3-trifluoro-2-hydroxy-2-methyl-propyl)-amide;
3-Amino-6-bromo-5-trifluoromethyl-pyridine-2-carboxylic acid (3,3,3-trifluoro-2-hydroxy-propyl)-amide;
3-Amino-6-bromo-5-trifluoromethyl-pyridine-2-carboxylic acid ((S)-3,3,3-trifluoro-2-hydroxy-propyl)-amide;
3-Amino-6-bromo-5 -trifluoromethyl-pyridine-2-carboxylic acid [(R)-1-(tetrahydro-furan-2-yl)methyl]-amide;
3-Amino-6-bromo-5-trifluoromethyl-pyridine-2-carboxylic acid ([1,3]dioxolan-2-ylmethyl)-amide;
3-Amino-6-bromo-5-trifluoromethyl-pyridine-2-carboxylic acid [(S)-1-(tetrahydro-furan-2-yl)methyl]amide;
3-Amino-6-bromo-5-trifluoromethyl-pyridine-2-carboxylic acid (tetrahydro-furan-2-ylmethyl)-amide;
3-Amino-6-bromo-5-trifluommethyl-pyridine-2-carboxylic acid (2-methyl-2-piperidin-1-yl-propyl)-amide;
3-Amino-6-bromo-5-trifluoromethyl-pyridine-2-carboxylic acid (2-hydroxy-propyl)-amide;
3-Amino-6-bromo-5-trifluoromethyl-pyridine-2-carboxylic acid (2-hydroxy-2-methyl-propyl)-amide;
3-Amino-6-bromo-5-trifluoromethyl-pyridine-2-carboxylic acid (2-methyl-tetrahydro-furan-2-yl-methyl)-amide;
3-Amino-6-bromo-5-trifluoromethyl-pyridine-2-carboxylic acid (2-methoxy-ethyl)-amide;
3-Amino-6-bromo-5-trifluoromethyl-pyridine-2-carboxylic acid [2-(4-fluoro-phenyl)-2-morpholin-4-yl-ethyl]-amide;
3-Amino-6-bromo-5-trifluoromethyl-pyridine-2-carboxylic acid (2-morpholin-4-yl-2-phenyl-ethyl)-amide;
3-Amino-6-bromo-5-trifluoromethyl-pyridine-2-carboxylic acid (2-dimethylamino-2-phenyl-ethyl)-amide;
3-Amino-6-(4-fluoro-phenyl)-5-trifluoromethyl-pyridine-2-carboxylic acid (3,3,3-trifluoro-2-hydroxy-2-methyl-propyl)-amide;
3-Amino-5-trifluoromethyl-pyridine-2-carboxylic acid (3,3,3-trifluoro-2-hydroxy-2-methyl-propyl)-amide;
3-Amino-6-(4-chloro-2-methyl-phenyl)-5-trifluoromethyl-pyridine-2-carboxylic acid ((R)-3,3,3-trifluoro-2-hydroxy-propyl)-amide;
3-Amino-6-bromo-5-trifluoromethyl-pyridine-2-carboxylic acid (3,3,3-trifluoro-2-hydroxy-2-trifluoromethyl-propyl)-amide;
5-Amino-6'-methyl-3-trifluoromethyl-[2,3']bipyridinyl-6-carboxylic acid (3,3,3-trifluoro-2-hydroxy-2-methyl-propyl)-amide;
3-Amino-6-bromo-5-trifluoromethyl-pyridine-2-carboxylic acid ((R)-3,3,3-trifluoro-2-hydroxy-2-methyl-propyl)-amide;
3-Amino-6-bromo-5-trifluoromethyl-pyridine-2-carboxylic acid ((S)-3,3,3-trifluoro-2-hydroxy-2-methyl-propyl)-amide;
3-Amino-6-methoxy-5-trifluoromethyl-pyridine-2-carboxylic acid (3,3,3-trifluoro-2-hydroxy-2-methyl-propyl)-amide;
3-Amino-6-(4-fluoro-phenyl)-5-trifluoromethyl-pyridine-2-carboxylic acid ((S)-3,3,3-trifluoro-2-hydroxy-2-methyl-propyl)-amide;
3-Amino-6-(4-fluoro-phenyl)-5-trifluoromethyl-pyridine-2-carboxylic acid ((R)-3,3,3-trifluoro-2-hydroxy-2-methyl-propyl)-amide;
3-amino-6-(2,4-dichloro-phenyl)-5-trifluoromethyl-pyridine-2-carboxylic acid (3,3,3-trifluoro-2-hydroxy-2-methyl-propyl)-amide;
3-Amino-6-(4-fluoro-phenyl)-5-trifluoromethyl-pyridine-2-carboxylic acid (2-hydroxy-2-methyl-propyl)-amide;
3-Amino-6-methoxy-5-trifluoromethyl-pyridine-2-carboxylic acid (3,3,3-trifluoro-2-hydroxy-propyl)-amide;
5-Amino-6'-methyl-3-trifluoromethyl-[2,3']bipyridinyl-6-carboxylic acid (3,3,3-trifluoro-2-hydroxy-2-trifluoromethyl-propyl)-amide;
5-Amino-6'-methyl-3-trifluoromethyl-[2,3']bipyridinyl-6-carboxylic acid (3,3,3-trifluoro-2-hydroxy-2-methyl-propyl)-amide;
3-Amino-5,6-bis-trifluoromethyl-pyridine-2-carboxylic acid ((S)-3,3,3-trifluoro-2-hydroxy-2-methyl-propyl)-amide;
3-Amino-5,6-bis-trifluoromethyl-pyridine-2-carboxylic acid ((R)-3,3,3-trifluoro-2-hydroxy-2-methyl-propyl)-amide;
3-Amino-6-methoxy-5-trifluoromethyl-pyridine-2-carboxylic acid ((S)-3,3,3-trifluoro-2-hydroxy-2-methyl-propyl)-amide;

3-Amino-6-methoxy-5-trifluoromethyl-pyridine-2-carboxylic acid ((R)-3,3,3-trifluoro-2-hydroxy-2-methyl-propyl)-amide;

Methyl 3-(3-amino-6-bromo-5-(trifluoromethyl)picolinamido)propanoate;

3-Amino-N-(benzo[d]isoxazol-3-ylmethyl)-6-bromo-5-(trifluoromethyl) picolinamide;

3-Amino-6-(oxazol-2-yl)-N-(3,3,3-trifluoro-2-hydroxy-2-methylpropyl)-5-(trifluoromethyl)picolinamide;

3-Amino-6-bromo-N-(3,3,3-trifluoro-2-methoxy-2-methylpropyl)-5-(trifluoromethyl)picolinamide;

3-amino-N-(2-hydroxy-3-methyl-2-(trifluoromethyl)butyl)-6-methoxy-5-(trifluoromethyl)picolinamide;

3-Amino-6-cyclopropyl-N-(3,3,3-trifluoro-2-hydroxy-2-methylpropyl)-5-(trifluoromethyl)picolinamide;

3-Amino-6-methoxy-N-(3,3,3-trifluoro-2-hydroxy-2-(trifluoromethyl)propyl)-5-(trifluoro methyl)picolinamide;

5-amino-N-(3,3,3-trifluoro-2-hydroxy-2-methylpropyl)-3-(trifluoromethyl)-2,4'-bipyridine-6-carboxamide;

3-Amino-6-bromo-5-trifluoromethyl-pyridine-2-carboxylic acid (3-methyl-2-oxo-butyl)-amide;

3-Amino-6-(1-methyl-1H-pyrazol-4-yl)-N-(3,3,3-trifluoro-2-hydroxy-2-methylpropyl)-5-(trifluoromethyl)picolinamide;

(S)-3-amino-6-ethoxy-N-(3,3,3-trifluoro-2-hydroxy-2-methylpropyl)-5-(trifluoro methyl)picolinamide;

3-Amino-6-(pyrrolidin-1-yl)-N-(3,3,3-trifluoro-2-hydroxy-2-methylpropyl)-5-(trifluoromethyl)picolinamide;

3-Amino-N-(2-amino-3,3,3-trifluoro-2-methylpropyl)-6-methoxy-5-(trifluoromethyl) picolinamide; or 3-Amino-6-methoxy-N-(3,3,3-trifluoro-2-(4-methoxybenzylamino)-2-methylpropyl)-5-(trifluoromethyl)picolinamide.

Embodiment 40

The compound according to embodiment 39, wherein the compound is

3-Amino-6-bromo-5-trifluoromethyl-pyridine-2-carboxylic acid [(R)-1-(tetrahydro-furan-2-yl)methyl]-amide;

3-Amino-6-bromo-5-trifluoromethyl-pyridine-2-carboxylic acid ([1,3]dioxolan-2-ylmethyl)-amide;

3-Amino-6-bromo-5-trifluoromethyl-pyridine-2-carboxylic acid [(S)-1-(tetrahydro-furan-2-yl)methyl]-amide;

3-Amino-6-bromo-5-trifluoromethyl-pyridine-2-carboxylic acid (tetrahydro-furan-2-ylmethyl)-amide; or 3-Amino-6-bromo-5-trifluoromethyl-pyridine-2-carboxylic acid (2-methyl-tetrahydro-furan-2-yl-methyl)-amide.

Embodiment 41

The compound according to embodiment 2, 21 or 28, wherein the compound is

3-Amino-6-bromo-5-trifluoromethyl-pyrazine-2-carboxylic acid [2-(4-fluoro-phenyl)-2-morpholin-4-yl-ethyl]-amide;

3-Amino-6-bromo-5-trifluoromethyl-pyridine-2-carboxylic acid [2-(4-fluoro-phenyl)-2-morpholin-4-yl-ethyl]-amide;

3-Amino-6-bromo-5-trifluoromethyl-pyridine-2-carboxylic acid (2-morpholin-4-yl-2-phenyl-ethyl)-amide;

3-Amino-6-bromo-5-trifluoromethyl-pyridine-2-carboxylic acid (2-dimethylamino-2-phenyl-ethyl)-amide;

3-Amino-6-bromo-5-trifluoromethyl-pyrazine-2-carboxylic acid (3-methyl-2-morpholin-4-yl-butyl)-amide;

3-Amino-6-bromo-5-trifluoromethyl-pyrazine-2-carboxylic acid (2-methyl-2-morpholin-4-yl-propyl)-amide;

3-Amino-6-bromo-5-trifluoromethyl-pyrazine-2-carboxylic acid (1-morpholin-4-yl-cyclohexylmethyl)-amide;

3-Amino-6-bromo-5-trifluoromethyl-pyrazine-2-carboxylic acid (2-morpholin-4-yl-2-phenyl-ethyl)-amide;

3-Amino-6-bromo-5-trifluoromethyl-pyrazine-2-carboxylic acid (2-dimethylamino-2-phenyl-ethyl)-amide;

3-Amino-6-bromo-5-trifluoromethyl-pyrazine-2-carboxylic acid [2-(4-methoxy-phenyl)-2-pyrrolidin-1-yl-ethyl]-amide;

3-Amino-N-(2-amino-3,3,3-trifluoro-2-methylpropyl)-6-methoxy-5-(trifluoromethyl) picolinamide; or 3-Amino-6-bromo-5-trifluoromethyl-pyrazine-2-carboxylic acid [2-dimethylamino-2-(4-methoxy-phenyl)-ethyl]-amide.

Embodiment 42

The compound according to embodiment 2, 21 or 28, wherein the compound is

3-Amino-6-bromo-5-trifluoromethyl-pyrazine-2-carboxylic acid (2-methyl-tetrahydro-furan-2-yl-methyl)-amide;

3-Amino-6-bromo-5-trifluoromethyl-pyrazine-2-carboxylic acid [2-(4-fluoro-phenyl)-2-morpholin-4-yl-ethyl]-amide;

3-Amino-6-bromo-5-trifluoromethyl-pyrazine-2-carboxylic acid (3-methyl-2-morpholin-4-yl-butyl)-amide;

3-Amino-6-bromo-5-trifluoromethyl-pyrazine-2-carboxylic acid (2-methyl-2-morpholin-4-yl-propyl)-amide;

3-Amino-6-bromo-5-trifluoromethyl-pyrazine-2-carboxylic acid (1-morpholin-4-yl-cyclohexylmethyl)-amide;

3-Amino-6-bromo-5-trifluoromethyl-pyrazine-2-carboxylic acid (2-morpholin-4-yl-2-phenyl-ethyl)-amide;

3-Amino-6-bromo-5-trifluoromethyl-pyrazine-2-carboxylic acid (2-dimethylamino-2-phenyl-ethyl)-amide;

3-Amino-6-bromo-5-trifluoromethyl-pyrazine-2-carboxylic acid [2-(4-methoxy-phenyl)-2-pyrrolidin-1-yl-ethyl]-amide;

3-Amino-6-bromo-5-trifluoromethyl-pyrazine-2-carboxylic acid [2-dimethylamino-2-(4-methoxy-phenyl)-ethyl]-amide;

3-Amino-6-bromo-5-trifluoromethyl-pyrazine-2-carboxylic acid [2-(4-fluoro-phenyl)-2-oxo-ethyl]-amide;

3-Amino-6-furan-2-yl-5-trifluoromethyl-pyrazine-2-carboxylic acid [2-(2-methoxy-phenyl)-ethyl]-amide;

3-amino-N-(3,3,3-trifluoro-2-hydroxy-2-methylpropyl)-5,6-bis(trifluoromethyl)pyrazine-2-carboxamide;

N-(2-(1H-imidazol-2-yl)propyl)-3-amino-6-bromo-5-(trifluoromethyl)pyrazine-2-carboxamide;

3-Amino-6-bromo-N-(2-morpholinoethyl)-5-(trifluoromethyl)pyrazine-2-carboxamide; or 3-Amino-6-bromo-5-trifluoromethyl-pyrazine-2-carboxylic acid [2-(4-fluoro-phenyl)-2-oxo-ethyl]-amide.

Embodiment 43

The compound according to embodiment 39, wherein the compound is

3-Amino-6-bromo-5-trifluoromethyl-pyridine-2-carboxylic acid (3,3,3-trifluoro-2-hydroxy-2-methyl-propyl)-amide;

3-Amino-6-bromo-5 -trifluoromethyl-pyridine-2-carboxylic acid (3,3,3-trifluoro-2-hydroxy-propyl)-amide;

3-Amino-6-bromo-5-trifluoromethyl-pyridine-2-carboxylic acid ((S)-3,3,3-trifluoro-2-hydroxy-propyl)-amide;

3-Amino-5,6-bis-trifluoromethyl-pyridine-2-carboxylic acid ((S)-3,3,3-trifluoro-2-hydroxy-2-methyl-propyl)-amide;

3-Amino-5,6-bis-trifluoromethyl-pyridine-2-carboxylic acid ((R)-3,3,3-trifluoro-2-hydroxy-2-methyl-propyl)-amide;

3-Amino-6-methoxy-5-trifluoromethyl-pyridine-2-carboxylic acid ((S)-3,3,3-trifluoro-2-hydroxy-2-methyl-propyl)-amide;

3-Amino-6-(4-fluoro-phenyl)-5-trifluoromethyl-pyridine-2-carboxylic acid ((S)-3,3,3-trifluoro-2-hydroxy-2-methyl-propyl)-amide;

3-Amino-6-(4-fluoro-phenyl)-5-trifluoromethyl-pyridine-2-carboxylic acid ((R)-3,3,3-trifluoro-2-hydroxy-2-methyl-propyl)-amide;

3-amino-6-(2,4-dichloro-phenyl)-5-trifluoromethyl-pyridine-2-carboxylic acid (3,3,3-trifluoro-2-hydroxy-2-methyl-propyl)-amide;

3-Amino-6-(4-fluoro-phenyl)-5-trifluoromethyl-pyridine-2-carboxylic acid (2-hydroxy-2-methyl-propyl)-amide; or 3-Amino-6-methoxy-5-trifluoromethyl-pyridine-2-carboxylic acid ((R)-3,3,3-trifluoro-2-hydroxy-2-methyl-propyl)-amide.

Embodiment 44

Use of a compound according to embodiment 1 to 43 in the manufacture of a medicament for use in the treatment of an inflammatory or obstructive airways disease or mucosal hydration.

Embodiment 45

Use of a compound according to embodiment 1 to 43 in the manufacture of a medicament for use in the treatment of a disease mediated by CFTR.

Embodiment 46

Use of a compound according to embodiment 42 in the manufacture of a medicament for use in the treatment of a disease mediated by CFTR, wherein the disease is CF or COPD.

Embodiment 47

Use of a compound according to embodiment 1 to 43 in the manufacture of a medicament for use in the treatment of cystic fibrosis.

Embodiment 48

A pharmaceutical composition for treating a disease or disorder mediated by CFTR, comprising:

the compound according to embodiment 1 to 43 and one or more pharmaceutically acceptable excipients.

Embodiment 49

A pharmaceutical composition, according to embodiment 48, wherein the disease or disorder is cystic fibrosis or COPD.

Embodiment 49

A pharmaceutical composition, according to embodiment 49, wherein the disease or disorder is cystic fibrosis.

Embodiment 50

A pharmaceutical combination, comprising:

a first active comprising the compound according to embodiment 1 to 43 and a second active selected from osmotic agents, ENaC blockers, anti-inflammatory agents, bronchodilatory agents, antihistamine agents, anti-tussive agents, antibiotic agents and DNase drug substances, wherein the first and second actives may be in the same or different pharmaceutical composition.

Embodiment 51

A pharmaceutical combination according to embodiment 50, wherein the second active agent is an EnaC blocker.

Embodiment 52

A process for the preparation of compounds of formula (I), comprising:

I

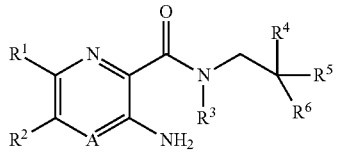

reacting a compound 1 with compound 2 in a peptide coupling reaction,

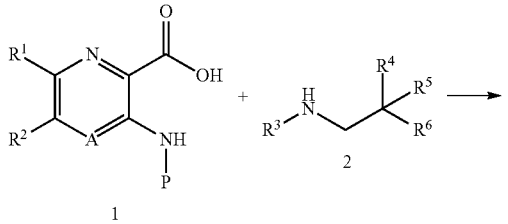

wherein $R^1$, $R^2$, $R^3$, $R^4$, $R^5$ and $R^6$ are as defined herein and P is a suitable amino protecting group;

removing protecting groups and isolating the compound of formula I.

Embodiment 53

The process according to embodiment 48, wherein the peptide coupling condition is HATU in an aprotic solvent.

We claim:

1. A compound of Formula I

I

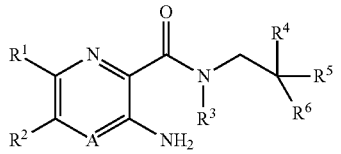

or a pharmaceutically acceptable salt thereof, wherein:

A is N or $CR^{4a}$;

$R^1$ is H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; $C_1$-$C_8$ alkoxy optionally substituted by one or more halogen atoms; halogen; $SO_2NR^8R^9$; $SO_2R^{10}$; S—$C_1$-$C_8$alkyl optionally substituted by one or more halogen atoms; S—$C_6$-$C_{14}$ aryl; CN; $NR^{11}R^{12}$; C(O)

$NR^{13}R^{14}$; $NR^{13}SO_2R^{15}$; $NR^{13}C(O)R^{15}$, $CO_2R^{15}$, —($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S; wherein the cycloalkyl, cycloalkenyl, aryl and heterocyclyl groups are each optionally substituted by one or more Z substituents;

$R^2$ is $C_1$-$C_4$ haloalkyl;

$R^3$ and $R^{4a}$ are each independently H or $C_1$-$C_8$ alkyl optionally substituted by one or more halogen atoms;

$R^4$ is H, or $C_1$-$C_8$ alkyl [optional] *optionally* substituted with one or more halogen *atoms*;

$R^5$ is —$(CH_2)_m$—$NR^{17}R^{18}$, —$(CH_2)_m$—OR', $C_1$-$C_8$ alkoxy optionally substituted by one or more halogen atoms; —($C_0$-$C_4$ alkyl)-$CO_2R^{15}$; —($C_0$-$C_4$ alkyl)-$C_6$-$C_{14}$ aryl or -3 to 14 membered heterocyclic group, wherein the heterocyclic group contains at least one heteroatom selected from N, O and S; wherein the —($C_0$-$C_4$ alkyl)-$C_6$-$C_{14}$ aryl and —($C_0$-$C_4$ alkyl)-3 to 14 membered heterocyclic group are each optionally substituted by one or more Z substituents;

$R^6$ is $C_1$-$C_8$ alkyl optionally substituted by one or more halogen atoms; $C_3$-$C_{10}$ cycloalkyl; —$C_1$-$C_4$ alkyl-$C_3$-$C_8$ cycloalkyl; $C_1$-$C_8$ alkoxy optionally substituted by one or more halogen atoms; OH; CN; halogen; —($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S; wherein the cycloalkyl, cycloalkenyl, —($C_0$-$C_4$ alkyl)-$C_6$-$C_{14}$ aryl and —($C_0$-$C_4$ alkyl)-3 to 14 membered heterocyclic group are each optionally substituted by one or more Z substituents; or $R^6$ is H, and $R^5$ is —$(CH_2)_m$—$NR^{17}R^{18}$, —$(CH_2)_m$—OR', $C_1$-$C_8$ alkoxy optionally substituted by one or more halogen atoms; —($C_0$-$C_4$ alkyl)-$C_6$-$C_{14}$ aryl; —($C_0$-$C_4$ alkyl)-3 to 14 membered heterocyclic group, wherein the heterocyclic group contains at least one heteroatom selected from N, O and S; or —($C_0$-$C_4$ alkyl)-$CO_2R^{15}$, wherein —($C_0$-$C_4$ alkyl)-$C_6$-$C_{14}$ aryl and —($C_0$-$C_4$ alkyl)-3 to 14 membered heterocyclic group groups are each optionally substituted by one or more Z substituents; or $R^4$ and $R^6$ together with the carbon atoms to which they are bound form a 3 to 8 membered carbocyclic ring system; or $R^4$ and $R^5$ together form an oxo group (C═O) and $R^6$ is $C_1$-$C_4$ alkyl optionally substituted by one or more halogen atoms; $C_1$-$C_4$ alkoxy optionally substituted by one or more halogen atoms; —($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S, wherein the aryl and heterocyclyl groups are each optionally substituted by one or more Z substituents; or $R^5$ and $R^6$ together with the carbon atoms to which they are bound *form* a 5 to 8 membered heterocyclic ring system containing one or more heteroatoms selected from N, O and S, wherein the ring system is optionally substituted by one or more Z substituents; or $R^4$ and $R^5$ and $R^6$ together with the carbon atoms to which they are bound form a 5 to 8 membered heterocyclic ring system containing one or more heteroatoms selected from N, O and S, wherein the ring system is optionally substituted by one or more Z substituents;

R' is H, or $C_1$-$C_8$ alkyl [optional] *optionally* substituted with one or more halogen *atoms*;

m is 0, 1, 2 or 3;

$R^8$, $R^{11}$, $R^{13}$ and $R^{17}$ are each independently H, $C_1$-$C_8$ alkyl optionally substituted by one or more halogen atoms, $C_3$-$C_{10}$ cycloalkyl or —($C_1$-$C_4$ alkyl)-$C_3$-$C_8$ cycloalkyl;

$R^9$, $R^{10}$, $R^{12}$, $R^{14}$, $R^{15}$[, $R^{16}$] and $R^{18}$ are each independently H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; —($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S, wherein the cycloalkyl, cycloalkenyl, aryl and heterocyclyl groups are each optionally substituted by one or more Z substituents; or $R^8$ and $R^9$, $R^{11}$ and $R^{12}$, $R^{13}$ and $R^{14}$, and $R^{17}$ and $R^{18}$ together with the nitrogen atom to which they are attached may form a 4 to 14 membered heterocyclic group optionally substituted by one or more Z substituents;

Z is independently OH, aryl, O-aryl, benzyl, O-benzyl, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups or $C_1$-$C_4$ alkoxy, $(SO_2)NR^{19}R^{21}$, $(SO_2)R^{21}$, $C(O)NR^{19}R^{21}$, $NR^{19}R^{21}$, $C(O)OR^{19}$, $C(O)R^{19}$, $SR^{19}$, $OR^{19}$, oxo, CN, $NO_2$, halogen or a 3 to 14 membered heterocyclic group, wherein the heterocyclic group contains at least one heteroatom selected from N, O and S;

$R^{19}$ and $R^{21}$ are each independently H; $C_1$-$C_8$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclic group, the heterocyclic group including one or more heteroatoms selected from N, O and S, optionally substituted by one or more groups selected from halogen, oxo, $C_1$-$C_6$ alkyl and $C(O)C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclic group, the heterocyclic group including one or more heteroatoms selected from N, O and S, optionally substituted by one or more groups selected from halogen, $C_1$-$C_6$ alkyl or $C(O)C_1$-$C_6$ alkyl; wherein the alkyl groups are optionally substituted by one or more halogen atoms, $C_1$-$C_4$alkoxy, $C(O)NH_2$, $C(O)NHC_1$-$C_6$ alkyl or $C(O)N(C_1$-$C_6$ alkyl$)_2$; or $R^{19}$ and $R^{21}$ together with the nitrogen atom to which they attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy.

2. The compound according to claim 1, or a pharmaceutically acceptable salt thereof, wherein A is $CR^{4a}$.

3. The compound according to claim 1, or a pharmaceutically acceptable salt thereof, wherein $R^1$ is $C_1$-$C_8$ alkyl optionally substituted by one or more halogen atoms; $C_1$-$C_8$ alkoxy optionally substituted by one or more halogen atoms; halogen; $NR^{11}R^{12}$, $C_6$-$C_{14}$ aryl; or —($C_0$-$C_4$ alkyl)-5 to 6 membered heterocyclic group, wherein the heterocyclic group contains at least one heteroatom selected from N, O and S, wherein the aryl and heterocyclic groups are each optionally substituted by one or more Z substituents.

4. The compound according to claim 3, or a pharmaceutically acceptable salt thereof, wherein $R^1$ is $C_1$-$C_4$ alkyl optionally substituted by one or more halogen atoms; $C_1$-$C_4$ alkoxy optionally substituted by one or more halogen atoms; or halogen.

5. The compound according to claim 3, or a pharmaceutically acceptable salt thereof, wherein $R^1$ is aryl, wherein aryl is phenyl optionally substituted by one or more Z substituents.

6. The compound according to claim 1, or a pharmaceutically acceptable salt thereof, wherein $R^2$ is $CF_3$.

7. The compound according to claim 1, or a pharmaceutically acceptable salt thereof, wherein $R^4$ is H or $C_1$-$C_4$ alkyl optionally substituted by one or more halogen atoms;

$R^5$ is $C_1$-$C_4$ alkoxy optionally substituted by one or more halogen atoms; —$(CH_2)_m$—$NR^{17}R^{18}$, [—$(CH_2)_m$—OR] —$(CH_2)_m$—$OR'$; or —($C_0$-$C_4$ alkyl)-3 to 14 membered heterocyclic group, wherein the heterocyclic group contains at least one heteroatom selected from N, O and S, wherein the aryl heterocyclyl groups is optionally substituted by one or more Z substituents;

$R^6$ is $C_1$-$C_4$ alkyl optionally substituted by one or more halogen atoms; $C_1$-$C_4$ alkoxy optionally substituted by one or more halogen atoms; or —($C_0$-$C_4$ alkyl)-$C_6$-$C_{14}$ aryl wherein the aryl is optionally substituted by one or more Z substituents; or $R^4$ and $R^6$ together with the carbon atoms to which they are bound form a 3 to 6 membered carbocyclic ring system; or $R^5$ and $R^6$ together with the carbon atoms to which they are bound form a 5 to 8 membered heterocyclic ring system containing one or more heteroatoms selected from N, O and S, wherein the ring system is optionally substituted by one or more Z substituents;

m is 0 or 1;

$R^{17}$ and $R^{18}$ are each independently H[;] *or* $C_1$-$C_8$ alkyl optionally substituted by one or more halogen atoms.

8. The compound according to claim 1, or a pharmaceutically acceptable salt thereof, wherein A is $CR^{4a}$;

$R^1$ is $C_1$-$C_4$ alkyl optionally substituted by one or more halogen atoms; or $C_1$-$C_4$ alkoxy optionally substituted by one or more halogen atoms;

$R^2$ is $CF_3$, $R^3$ is H, CH, or $CF_3$;

$R^4$ is H or Me;

$R^{4a}$ is H;

$R^5$ is —$NR^{17}R^{18}$ or OH, and $R^6$ is $C_1$-$C_4$ alkyl optionally substituted by one or more halogen atoms.

9. [The] *A* compound represented by formula II,

II

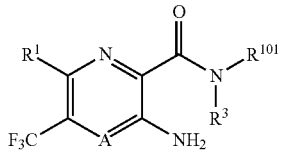

or a pharmaceutically acceptable salt *thereof*;

wherein

A is N or $CR^{4a}$;

[$R^a$] $R^{4a}$ is H or $C_1$-$C_4$ alkyl;

$R^1$ is $C_1$-$C_8$ alkyl optionally substituted by one or more halogen atoms; $C_1$-$C_8$ alkoxy optionally substituted by one or more halogen atoms; halogen; $NR^{11}R^{12}$[,]; $C_6$-$C_{14}$ aryl; or —($C_0$-$C_4$ alkyl)-5 to 6 membered heterocyclic group, wherein the heterocyclic group contains at least one heteroatom selected from N, O and S, wherein the aryl and heterocyclic groups are each optionally substituted by one or more Z substituents;

*$R^{11}$ is H, $C_1$-$C_8$ alkyl optionally substituted by one or more halogen atoms, $C_3$-$C_{10}$ cycloalkyl or —($C_1$-$C_4$ alkyl)-$C_3$-$C_8$ cycloalkyl;*

*$R^{12}$ is H; $C_1$-$C_8$ alkyl optionally substituted by one or more halogen atoms; $C_2$-$C_8$ alkenyl; $C_2$-$C_8$ alkynyl; $C_3$-$C_{10}$ cycloalkyl; $C_5$-$C_{10}$ cycloalkenyl; —$C_1$-$C_4$ alkyl-$C_3$-$C_8$ cycloalkyl; —($C_0$-$C_4$ alkyl)-$C_6$-$C_{14}$ aryl; or —($C_0$-$C_4$ alkyl)-3 to 14 membered heterocyclic group, wherein the heterocyclic group contains at least one heteroatom selected from N, O and S, wherein the cycloalkyl, cycloalkenyl, aryl and heterocyclyl groups are each optionally substituted by one or more Z substituents; or*

*$R^{11}$ and $R^{12}$ together with the nitrogen atom to which they are attached may form a 4 to 14 membered heterocyclic group optionally substituted by one or more Z substituents;*

*Z is independently OH, aryl, O-aryl, benzyl, O-benzyl, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups or $C_1$-$C_4$ alkoxy, $(SO_2)NR^{19}R^{21}$, $(SO_2)R^{21}$, $C(O)NR^{19}R^{21}$, $NR^{19}R^{21}$, $C(O)OR^{19}$, $C(O)R^{19}$, $SR^{19}$, $OR^{19}$, oxo, CN, $NO_2$, halogen or a 3 to 14 membered heterocyclic group, wherein the heterocyclic group contains at least one heteroatom selected from N, O and S;*

*$R^{19}$ and $R^{21}$ are each independently H; $C_1$-$C_8$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)- 3- to 14-membered heterocyclic group, the heterocyclic group including one or more heteroatoms selected from N, O and S, optionally substituted by one or more groups selected from halogen, oxo, $C_1$-$C_6$ alkyl and $C(O)C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclic group, the heterocyclic group including one or more heteroatoms selected from N, O and S, optionally substituted by one or more groups selected from halogen, $C_1$-$C_6$ alkyl or $C(O)C_1$-$C_6$ alkyl; wherein the alkyl groups are*

*optionally substituted by one or more halogen atoms, $C_1$-$C_4$ alkoxy, $C(O)NH_2$, $C(O)NHC_1$-$C_6$ alkyl or $C(O)N(C_1$-$C_6$ alkyl$)_2$; or*

*$R^{19}$ and $R^{21}$ together with the nitrogen atom to which they attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclic substituent groups are optionally substituted by $C_1$-$C_6$ alkyl, $C_1$-$C_6$ haloalkyl or $C_1$-$C_6$ alkoxy;*

[$R_3$] $R^3$ is H or $CH_3$;

$R^{101}$ is

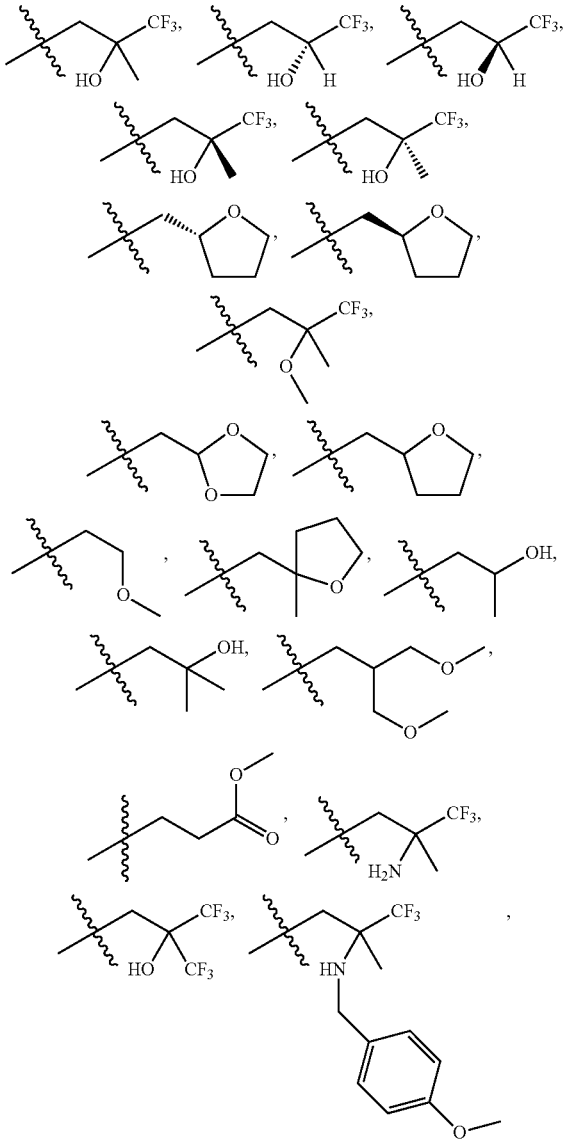

-continued

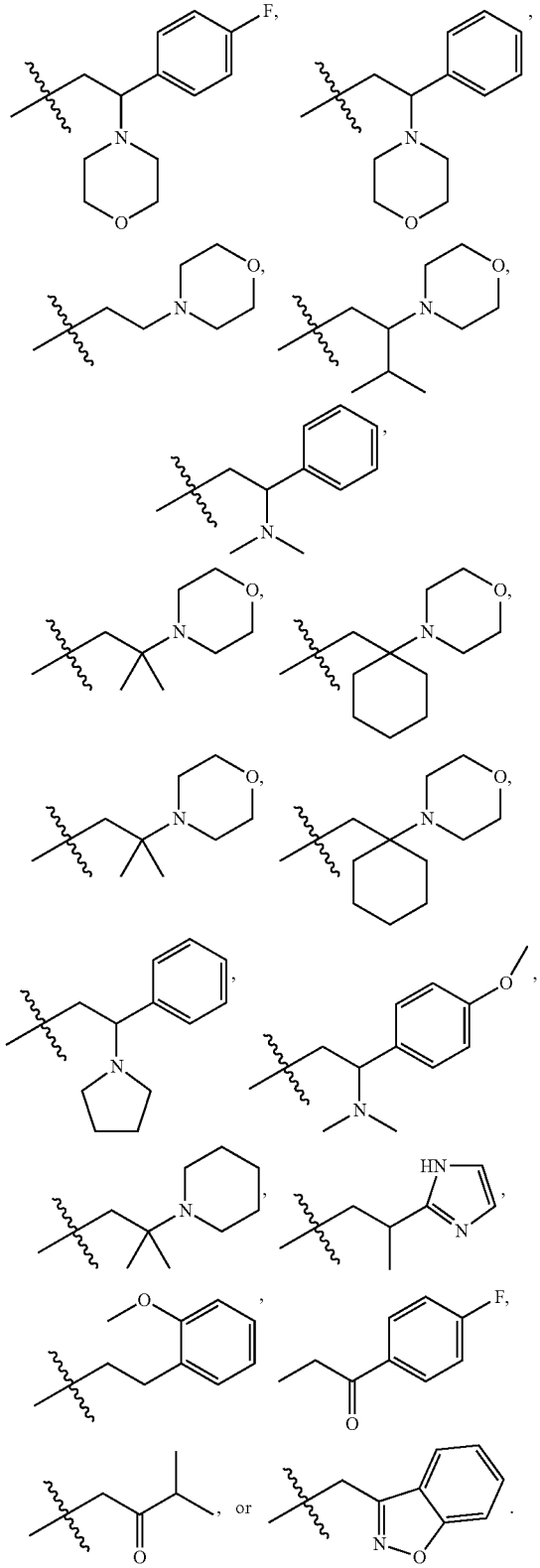

10. A pharmaceutical composition, comprising:

the compound according to claim 1, or a pharmaceutically acceptable salt thereof and one or more pharmaceutically acceptable excipients.

11. A pharmaceutical combination, comprising:

a first active comprising the compound according to claim 1, or a pharmaceutically acceptable salt thereof, and a second active selected from osmotic agents, ENaC blockers, anti-inflammatory agents, bronchodilatory agents, antihistamine agents, anti-tussive agents, antibiotic agents and DNase drug substances, wherein the first and second actives may be in the same or different pharmaceutical composition.

12. A method *for* the symptomatic treatment of cystic fibrosis, asthma, or COPD, comprising:

administering an effective amount of at least one compound according to claim 1, or a pharmaceutically acceptable salt thereof, to a subject in need of such treatment.

*13. A method for the symptomatic treatment of cystic fibrosis comprising administering to a subject in need of such treatment an effective amount of at least one compound selected from:*

*3-Amino-6-methoxy-5-trifluoromethyl-pyridine-2-carboxylic acid ((S)-3,3,3-trifluoro-2-hydroxy-2-methyl-propyl)-amide;*

*3-Amino-6-methoxy-5-trifluoromethyl-pyridine-2-carboxylic acid ((R)-3,3,3-trifluoro-2-hydroxy-2-methyl-propyl)-amide;*

*3-Amino-6-(4-fluoro-phenyl)-5-trifluoromethyl-pyridine-2-carboxylic acid (3,3,3-trifluoro-2-hydroxy-2-methyl-propyl)-amide;*

*3-Amino-5,6-bis-trifluoromethyl-pyridine-2-carboxylic acid ((S)-3,3,3-trifluoro-2-hydroxy-2-methyl-propyl)-amide; and*

*3-Amino-5,6-bis-trifluoromethyl-pyridine-2-carboxylic acid ((R)-3,3,3-trifluoro-2-hydroxy-2-methyl-propyl)-amide;*

*or a pharmaceutically acceptable salt thereof.*

*14. A method for the symptomatic treatment of asthma comprising administering to a subject in need of such treatment an effective amount of at least one compound selected from:*

*3-Amino-6-methoxy-5-trifluoromethyl-pyridine-2-carboxylic acid ((S)-3,3,3-trifluoro-2-hydroxy-2-methyl-propyl)-amide;*

*3-Amino-6-methoxy-5-trifluoromethyl-pyridine-2-carboxylic acid ((R)-3,3,3-trifluoro-2-hydroxy-2-methyl-propyl)-amide;*

*3-Amino-6-(4-fluoro-phenyl)-5-trifluoromethyl-pyridine-2-carboxylic acid (3,3,3-trifluoro-2-hydroxy-2-methyl-propyl)-amide;*

*3-Amino-5,6-bis-trifluoromethyl-pyridine-2-carboxylic acid ((S)-3,3,3-trifluoro-2-hydroxy-2-methyl-propyl)-amide; and*

*3-Amino-5,6-bis-trifluoromethyl-pyridine-2-carboxylic acid ((R)-3,3,3-trifluoro-2-hydroxy-2-methyl-propyl)-amide;*

*or a pharmaceutically acceptable salt thereof.*

*15. A method for the symptomatic treatment of COPD comprising administering to a subject in need of such treatment an effective amount of at least one compound selected from:*

*3-Amino-6-methoxy-5-trifluoromethyl-pyridine-2-carboxylic acid ((S)-3,3,3-trifluoro-2-hydroxy-2-methyl-propyl)-amide;*

*3-Amino-6-methoxy-5-trifluoromethyl-pyridine-2-carboxylic acid ((R)-3,3,3-trifluoro-2-hydroxy-2-methyl-propyl)-amide;*

*3-Amino-6-(4-fluoro-phenyl)-5-trifluoromethyl-pyridine-2-carboxylic acid (3,3,3-trifluoro-2-hydroxy-2-methyl-propyl)-amide;*

*3-Amino-5,6-bis-trifluoromethyl-pyridine-2-carboxylic acid ((S)-3,3,3-trifluoro-2-hydroxy-2-methyl-propyl)-amide; and*

*3-Amino-5,6-bis-trifluoromethyl-pyridine-2-carboxylic acid ((R)-3,3,3-trifluoro-2-hydroxy-2-methyl-propyl)-amide;*

*or a pharmaceutically acceptable salt thereof.*

*16. The method according to claim 13 wherein the compound is in free form.*

*17. The method according to claim 13 wherein the compound is a pharmaceutically acceptable salt.*

*18. The method according to claim 14 wherein the compound is in free form.*

*19. The method according to claim 14 wherein the compound is a pharmaceutically acceptable salt.*

*20. The method according to claim 15 wherein the compound is in free form.*

*21. A method according to claim 15 wherein the compound is a pharmaceutically acceptable salt.*

* * * * *